United States Patent [19]

Silverman et al.

[11] Patent Number: 5,569,664
[45] Date of Patent: Oct. 29, 1996

[54] INSECTICIDAL N-(SUBSTITUTED ARYLMETHYL)-4-[BIS(SUBSTITUTED PHENYL) METHYL]PIPERIDINES

[75] Inventors: Ian R. Silverman, Maple Shade; Daniel H. Cohen, Princeton; John W. Lyga, Basking Ridge, all of N.J.; Steven W. Szczepanski, Philadelphia, Pa.; Syed F. Ali, Yardville, N.J.

[73] Assignee: FMC Corporation, Philadelphia, Pa.

[21] Appl. No.: 445,315

[22] Filed: May 19, 1995

Related U.S. Application Data

[62] Division of Ser. No. 389,675, Feb. 16, 1995.

[51] Int. Cl.$^6$ .............. A61K 31/445; C07D 211/20
[52] U.S. Cl. .............. 514/317; 514/318; 514/319; 514/321; 514/326; 514/331; 546/193; 546/197; 546/205; 546/212; 546/214; 546/236; 424/405
[58] Field of Search ................. 546/193, 197, 546/205, 212, 214, 236; 514/317, 318, 319, 321, 326, 331; 424/405

[56] References Cited

U.S. PATENT DOCUMENTS

| | | | |
|---|---|---|---|
| 4,035,372 | 7/1977 | Deason | 546/229 |
| 4,628,095 | 12/1986 | Rorig | 546/234 |
| 5,340,831 | 8/1994 | Cross | 514/408 |
| 5,422,358 | 6/1995 | Cross | 514/320 |

FOREIGN PATENT DOCUMENTS

| | | |
|---|---|---|
| 183216 | 4/1986 | European Pat. Off. |
| 87129392 | 6/1986 | Saudi Arabia |

OTHER PUBLICATIONS

Wyngaarden et al. "Cecil textbook of medicine" p. 70 (1983).

Lecorronc et al. "Pharmacological properties of presynaptic muscarinic receptors in the 6th abdominal–ganglion of the cockroach" Pesticide Sci. v. 33, pp. 205–211 (1991) (abstract from SciSearch provided).

Primary Examiner—Ceila Chang
Attorney, Agent, or Firm—H. Robinson Ertelt; Robert M. Kennedy

[57] ABSTRACT

Compounds of the following structure, the corresponding N-oxides and agriculturally acceptable salts, are disclosed as effective insecticides:

$$R-U-N\underset{}{\underset{}{\bigcirc}}\underset{R^2}{\overset{R^1}{-C-Q}}$$

in which U is selected from $-(CH_2)_n-$, where n is 1, 2, or 3;   A

Q is selected from hydrogen, hydroxy, sulfhydryl, and fluorine; R is selected from a heterocycle having 5 or 6 ring atoms, optionally fused to a benzene ring, and

[benzene ring with substituents V, W, X, Y, Z]

wherein V, W, X, Y, Z are as defined in the specification.

31 Claims, No Drawings

INSECTICIDAL N-(SUBSTITUTED ARYLMETHYL)-4-[BIS(SUBSTITUTED PHENYL) METHYL]PIPERIDINES

This is a request for filling a divisional application under 37 CFR 1.60, of pending prior application Ser. No. 08/389, 675 filed on Feb. 16, 1995.

The present invention relates to methods for controlling insects. In particular, it relates to control by the application of certain N-(substituted arylmethyl)-4-[bis(substituted phenyl)methyl]piperidines to the locus where insect control is needed. While not all compounds of the class are novel, the insecticidal efficacy of these compounds is heretofore unknown.

Many derivatives of N-(substituted arylmethyl)-4-[bis-(substituted)phenylmethyl]piperidines have been disclosed as cardiovascular or antiallergy agents. South African Pat. No. 8604-552A discloses such use for compounds of the formula:

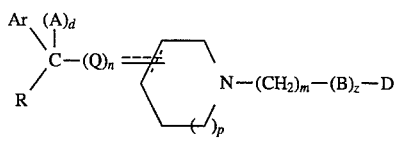

in which p is 0, 1, or 2;

A is, inter alia, hydrogen or hydroxy;

m is 0 to 6 inclusive;

Q is —CH—, —CH$_2$—, or —CH(OH)—;

d and n are 0 or 1, and the dotted lines represent optional double bonds consistent with the valence of carbon;

Ar, D, and R are selected, inter alia, from

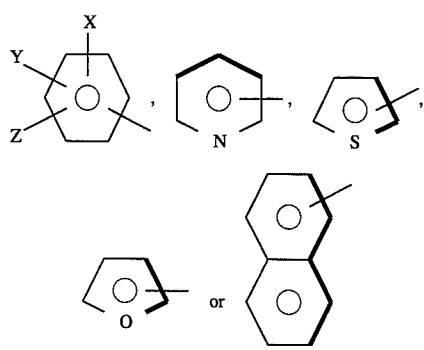

X, Y, and Z are selected from a variety of substituents, including hydrogen, lower alkyl, halogen, nitro, cyano, amino, alkoxy, thioalkyl, and carbonyl- or sulfonyl-containing groups;

B is, inter alia, sulfur or oxygen.

There are several provisos, and the pharmaceutically acceptable salts of these compounds are also disclosed as having the same utility.

U.S. Pat. No. 4,628,095 dicloses as cardiovascular agents compounds of the formula

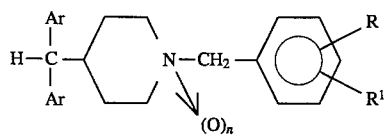

in which

Ar is phenyl, optionally substituted with halogen;

R is lower alkoxy or di(lower alkyl)amino;

R$_1$ is hydrogen, lower alkoxycarbonyl, carboxy, or lower alkyl aminocarbonyl; and n is 0 or 1, provided that when R$_1$ hydrogen, n is 1.

It has now been found that compounds of the following structure and their corresponding N-oxides, as well as their agriculturally acceptable salts, are active as insecticides:

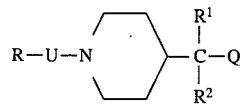

in which

U is selected from

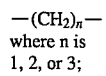     A
—(CH$_2$)$_n$—
where n is 1, 2, or 3;

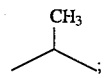     B

     C$^1$

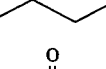     D

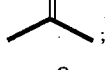     E$^2$ and

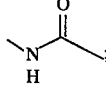     F $^1$The right side of the bridging group C is attached to the nitrogen atom of the piperidine ring.
$^2$The right side of the bridging group E is attached to the nitrogenatom of the piperidine ring.

Q is selected from hydrogen, hydroxy, sulfhydryl, and fluorine;

R is selected from a heterocycle having 5 or 6 ring atoms, optionally fused to a benzene ring, and

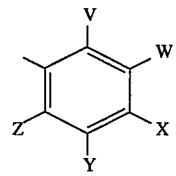

in which

V is hydrogen, halogen, alkyl, haloalkyl, alkoxy, alkylthio, alkylsulfinyl, alkylsilyloxy, dialkylamino, cyano, nitro, hydroxy, and phenyl;

W is hydrogen, halogen, alkyl, haloalkyl, alkoxy, nitro, amino, phenoxy, or phenylalkoxy;

X is hydrogen, hydroxy, halogen, alkyl, alkoxyalkyl, alkoxy, cycloalkylalkoxy, haloalkoxy, alkenyloxy, haloalkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkylcarbonyl, alkoxycarbonylamino, alkoxycarbonyl, alkylaminocarbonyl, aminocarbonyloxy, phenyl, phenylalkoxy, phenoxy, phenoxyalkyl, or a five- or six-membered heterocycle; each cycloalkyl moiety, heterocycle, or phenyl ring is optionally substituted with halogen, alkoxy, or haloalkoxy;

Y and Z are independently selected from hydrogen and alkoxy;

W and X taken together may be —OCH$_2$CH$_2$O—, —CH$_2$C(CH$_3$)$_2$O—, —OC(CH$_3$)$_2$O—, —N═C(C$_2$H$_5$)O—, or —CH═CHCH═CH—;

R$^1$ and R$^2$ are independently selected from a five- or six-membered heterocycle or phenyl, phenyl substituted with one or more halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and n is 1, 2, or 3;

with the proviso that each aliphatic moiety contains not more than 6 carbon atoms, halogen means bromine, chlorine or fluorine, each heterocycle contains from 1 to 4 nitrogen atoms, or 1 or 2 oxygen or sulfur atoms, or 1 or 2 nitrogen atoms and an oxygen atom, and each phenyl, heterocycle, or cycloalkyl moiety is optionally substituted with one or more halogen or alkyl or alkoxy of 1 to 3 carbon atoms, and each alkyl substituent on an amino nitrogen contains 1 to 4 carbon atoms.

Preferred are those compounds in which R is thien-2-yl, indol-3-yl, or

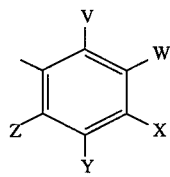

Q is selected from hydrogen, hydroxy, sulfhydryl, and fluorine;

U is selected from —(CH$_2$)$_n$— and ethylidene;

V is selected from hydrogen, halogen, and alkoxy;

Y and Z are each hydrogen;

W is selected from hydrogen, halogen, and alkoxy; and

X is selected from hydrogen, hydroxy, halogen, alkyl, haloalkyl, alkenyl, alkynyl, alkoxy, alkenyloxy, alkynyloxy, haloalkoxy, cycloalkylalkoxy, alkylthio, haloalkylthio, monoalkylamino, dialkylamino, alkoxyalkyl, alkoxyalkoxy, alkylcarbonyl, alkoxycarbonyl, alkylaminocarbonyl, alkylcarbonylamino, aminocarbonyloxy, alkoxycarbonylamino, cyano, phenyl, phenoxy, phenoxyalkyl, and a five-membered heterocycle;

W and X taken together may be —OCH$_2$CH$_2$O—, —CH$_2$C(CH$_3$)$_2$O—, or —OC(CH$_3$)$_2$O—;

R$^1$ and R$^2$ are independently selected from phenyl substituted with halogen, haloalkyl, or haloalkoxy; and n is 1, with the following provisos: one of R$^1$ and R$^2$ is phenyl substituted in the para position; each aliphatic moiety contains 1 to 4 carbon atoms, each cycloalkyl moiety contains 3 or 4 carbon atoms; halogen means chlorine or fluorine, each alkyl or alkoxy substituent on nitrogen contains 1 to 3 carbon atoms, each heterocycle contains from 1 to 4 nitrogen atoms, or 1 or 2 oxygen atoms, or 1 or 2 nitrogen atoms and an oxygen atom, and each phenyl, heterocycle, or cycloalkyl moiety is optionally substituted with one or more halogen or alkyl or alkoxy of 1 to 3 carbon atoms;

and the corresponding N-oxides and agriculturally acceptable salts.

Particularly preferred are those compounds in which

Q is —OH;

U is —(CH$_2$)$_n$—;

V is selected from hydrogen and methoxy;

Y and Z are each hydrogen;

W is selected from hydrogen, fluorine, methyl, methoxy and ethoxy; and

X is selected from hydrogen, halogen, methyl, methoxy, ethoxy, n-propoxy, i-propoxy, n-butoxy, 1-methylpropoxy, 2-methylpropoxy, cyclopropylmethoxy, 2-chloro-2-propenoxy, 3-chloro-2-propenoxy, 2-methyl-2-propenoxy, 3-methyl-2-butenoxy, 1-methylcyclopropylmethoxy, 2-methylcyclopropylmethoxy, cyclobutylmethoxy, cyclohexoxy, perfluoroethoxy, allyloxy, propargyloxy, 2-butynoxy, difluoromethoxy, perfluoroethylthio, cyanomethoxy, (methyl)cyanomethoxy, 2-methoxyethoxymethoxy, cyano, phenyl, phenoxy, 2-fluorophenoxy, 4-fluorophenoxy, phenylmethoxy, ethylcarbonyl, ethoxymethyl, methoxycarbonyl, ethoxycarbonyl, i-propoxycarbonyl, methoxymethoxycarbonyl, methylcarbonylmethoxy, dimethylamino, methylcarbonylamino, ethylcarbonylamino, methoxycarbonylamino, ethoxycarbonylamino, i-propoxycarbonylamino, butoxycarbonylamino, (N-methyl)methoxycarbonylamino, 2,2,2-trifluoroethoxycarbonylamino, (N-propyl)methoxycarbonylamino, cyclopentoxycarbonylamino, phenoxycarbonylamino, dimethylaminocarbonyloxy, methylaminocarbonyloxy, ethylaminocarbonyloxy, ethoxysulfonyl, N-methylpyrol-3-yl, 2-methyl-2H-tetrazol-5-yl, 2-(2-propyl)-2H-tetrazol-5-yl, and 1,2,4-oxadiazol-5-yl;

W and X taken together may be —CH$_2$C(CH$_3$)$_2$O—;

n is 1; and

R$^1$ and R$^2$ are independently selected from p-trifluoromethoxyphenyl and p-trifluoromethylphenyl;

and the corresponding N-oxides and agriculturally acceptable salts.

The compounds of the present invention were prepared by methods generally known to those skilled in the art. In the method shown in Schema 1, where R$^1$ and R$^2$ are the same, ethyl piperidin-4-ylcarboxylate was reacted with either an appropriately substituted alkyl halide, for example, 4-methoxyphenylmethyl bromide, or with an appropriately substituted aldehyde under reductive conditions, for example, 4-phenoxybenzaldehyde, affording the corresponding ethyl N-substituted alkylpiperidin-4-ylcarboxylate (A). Intermediate (A) was then treated with more than two molar equivalents of the Grignard reagent of an appropriately substituted halide, for example, 4-trifluoromethoxyphenyl magnesium bromide, yielding the desired N-(substituted alkyl)-4-[bis(substituted)hydroxymethyl]piperidine (I), for example, N-(4-methoxyphenylmethyl)-4-[bis(4-trifluoromethoxyphenyl)hydroxymethyl]piperidine (Compound 24). Examples 1–3, 5, 6, and 10 provide detailed descriptions of how these reactions are conducted.

Another method, shown in Schema 2, again for cases where R$^1$ and R$^2$ are the same, uses the method of D. A.

Walsh et al.(J. Med. Chem. 1989, 32, 105–118). In this method ethyl piperidin-4-ylcarboxylate was reacted with diethyl carbamoyl chloride, under basic conditions, affording the corresponding intermediate, ethyl N-diethylaminocarbonylpiperidin-4-yl-carboxylate (B). Intermediate (B) was treated with more than two molar equivalents of the Grignard reagent of an appropriately substituted halide, yielding the corresponding N-diethylaminocarbonyl-4-[bis(substituted)hydroxymethyl]piperidine (C). Intermediate (C) was then treated with lithium aluminum hydride, affording the 4-[bis(substituted)hydroxymethyl]piperidine (II), for example, 4-[bis(4-trifluoromethoxyphenyl)hydroxymethyl]piperidine. As depicted in Schema 2C, intermediate (II) was reacted with either an appropriately substituted alkyl halide or with an appropriately substituted aldehyde, as previously described, affording the desired N-(substituted alkyl)-4-[bis(substituted)hydroxymethyl]piperidine (I), for example, N-(4-ethoxycarbonylphenylmethyl)-4-[bis(4-trifluoromethoxyphenyl)hydroxymethyl]piperidine (Compound 57). Example 7 provides a detailed description of how this reaction is conducted.

The preparation of intermediate (II) using the method described above provided relatively low yields of (II). To obtain improved yields of (II), two other synthesis routes to this intermediate were used.

In the first alternative route to intermediate (II), shown in Schema 2A, the hydrochloride salt (D) of an N-phenylmethyl-4-[bis(substituted)hydroxymethyl]piperidine (I), for example, N-phenylmethyl-4-[bis(4-trifluoromethoxyphenyl)hydroxymethyl]piperidine, was treated with ammonium formate in the presence of 10% palladium on charcoal, readily affording intermediate (II). Again, intermediate (II) was reacted as shown in Schema 2C, affording the desired N-(substituted alkyl)-4-[bis(substituted)hydroxymethyl]piperidine (I), for example, N-[4-(methylcarbonylamino)phenylmethyl]-4-[bis(4-trifluoromethoxyphenyl)hydroxymethyl]piperidine (Compound 66). Example 12 provides a detailed description of how this reaction is conducted.

In the second alternative route to intermediate (II), shown in Schema 2B, ethyl pyridin-4-ylcarboxylate was reacted with more than two molar equivalents of the Grignard reagent of an appropriately substituted halide, affording the corresponding 4-[bis(substituted)hydroxymethyl]pyridine (E). The hydrochloride salt (F) of intermediate (E) was then prepared and was hydrogenated in the presence of platinum oxide, affording the corresponding 4-[bis(substituted)hydroxymethyl]piperidine hydrochloride salt (IIA). As shown in Schema 2C, intermediate (IIA) was in turn reacted under basic conditions, affording the desired N-(substituted alkyl)-4-[bis(substituted)hydroxymethyl]piperidine (I), for example, N-[4-(2-propyn-1-yloxy)phenylmethyl]-4-[bis(4-trifluoromethoxyphenyl)hydroxymethyl]piperidine (Compound 65). Example 11 provides a detailed description of how this reaction is conducted.

The intermediate 4-[bis(substituted)hydroxymethyl]piperidine (II) described above, was also reacted, as shown in Schema 2C, with an appropriately substituted acid chloride, for example, 3-chloro-4-methoxybenzoyl chloride, under basic conditions, yielding the corresponding N-(substituted carbonyl)-4-[bis-(substituted)hydroxymethyl]piperidine (G). Intermediate (G) was reduced with borane-methyl sulfide complex, affording the desired N-(substituted alkyl)-4-[bis(substituted)hydroxymethyl]piperidine (I), for example, N-(3-chloro-4-methoxy-phenylmethyl)-4-[bis(4-trifluoromethoxyphenyl)hydroxymethyl]piperidine (Compound 44). Example 8 provides a detailed description of how this reaction is conducted.

Schema 3 shows the method used when $R^1$ and $R^2$ are not the same. Here 4-aminocarbonylpiperidine was reacted with an appropriately substituted alkyl halide, for example, 4-propoxyphenylmethyl chloride, under basic conditions, affording the corresponding N-(substituted alkyl)-4-aminocarbonylpiperidine (H). Treatment of intermediate (H) with phosphorous oxychloride yielded the corresponding N-(substituted alkyl)-4-cyanopiperidine (J), which was in turn reacted with the Grignard reagent of an appropriately substituted halide, for example, 4-trifluoromethoxyphenylmagnesium bromide, yielding the corresponding N-(substituted alkyl)-4-(substituted carbonyl)piperidine (K). Intermediate (K) was reacted with a different Grignard reagent of an appropriately substituted halide, for example, 4-chlorophenylmagnesium bromide, yielding the desired N-(substituted alkyl)-4-[di(substituted)hydroxymethyl]piperidine (I), for example, N-(4-propoxyphenylmethyl)-4-[(4-trifluoromethoxyphenyl)(4-chlorophenyl)hydroxymethyl]piperidine. Example 4 provides a detailed description of how this reaction is conducted.

As depicted in Schema 4, the N-(substituted alkyl))-4-[bis(substituted)hydroxymethyl]piperidines (I) of the present invention may be further reacted by methods known in the art to prepare other insecticidally active compounds also within the scope of the present invention.

In a two-step route, (I), for example, N-(4-propoxyphenylmethyl)-4-[bis(4-trifluoromethoxyphenyl)hydroxymethyl]piperidine (prepared in Example 10), was treated with Lawesson's reagent in 1,2-dimethoxyethane, affording the corresponding N-(substituted alkyl))-4-[bis(substituted)mercaptomethyl]piperidine (L). Reduction of (L) with Raney® nickel in the presence of concentrated ammonium hydroxide and 1,3-cyclohexadiene in methanol yielded the targeted deshydroxy N-(substituted alkyl))-4-[bis(substituted)methyl]piperidine (IB). Example 13 provides a detailed description of how this reaction is conducted.

In an alternate one-step route, the dehydroxylated compounds (IB) were also prepared by the reduction of N-(substituted alkyl))-4-[bis(substituted)hydroxymethyl]piperidines (I) with trifluoroacetic acid and triethylsilane in methylene chloride. Example 14 provides a detailed description of how this reaction is conducted.

The N-(substituted alkyl))-4-[bis(substituted)hydroxymethyl]piperidines (I), for example, N-(4-propoxyphenylmethyl)-4-[bis(4-trifluoromethoxyphenyl)hydroxymethyl]piperidine, were also dehydroxylated and fluorinated with diethylaminosulfurtrifluoride (DAST) in methylene chloride, affording the corresponding N-(substituted alkyl))-4-[bis(substituted)fluoromethyl]piperidines (IC). Example 15 provides a detailed description of how this reaction is conducted.

In a preferred method to prepare the intermediate 4-[bis(substituted)hydroxymethyl]piperidine (II), ethyl piperidin-4-ylcarboxylate was reacted with chlorotrimethylsilane under basic conditions in diethyl ether, affording ethyl N-(trimethylsilyl)piperidin-4-ylcarboxylate. The so-prepared ethyl carboxylate was then reacted with more than two molar equivalents of the Grignard reagent of an appropriately substituted halide, a method previously described, affording intermediate (II) Both steps of this method provided product in good yield. Example 26 provides a detailed description of how this reaction is conducted. Schema 5 shows this method.

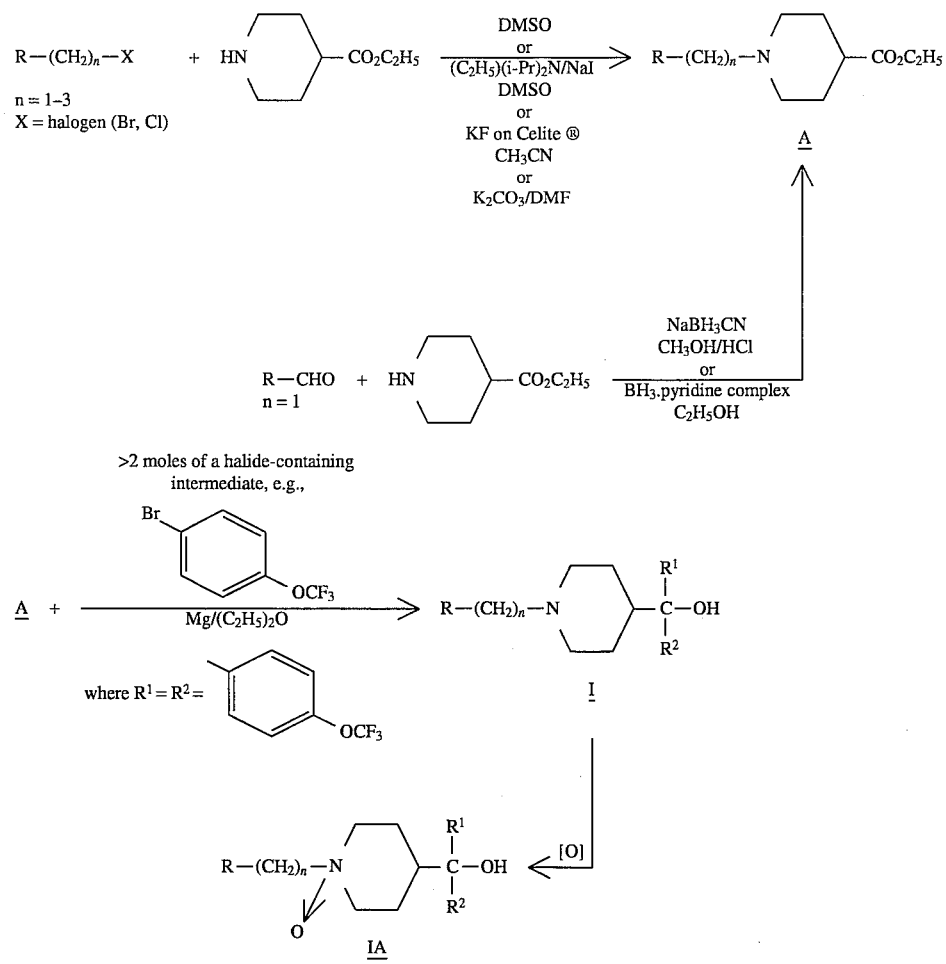
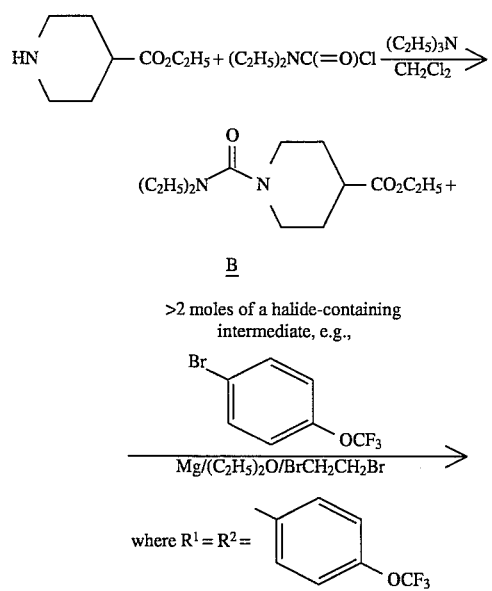
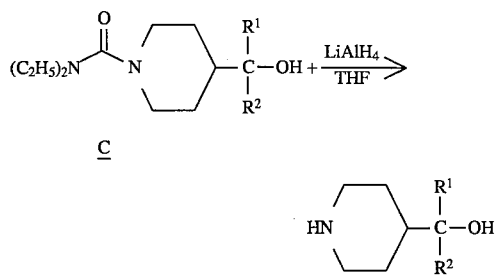
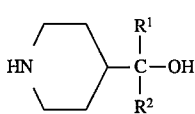

SCHEME 2A
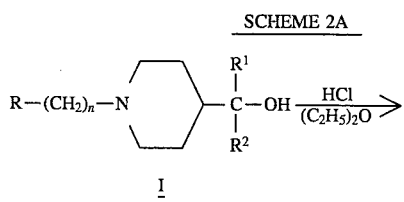
where R is phenyl, n is 1, and
$R^1 = R^2 =$ 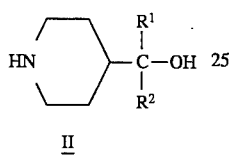
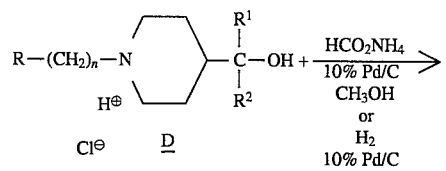
SCHEMA 2B
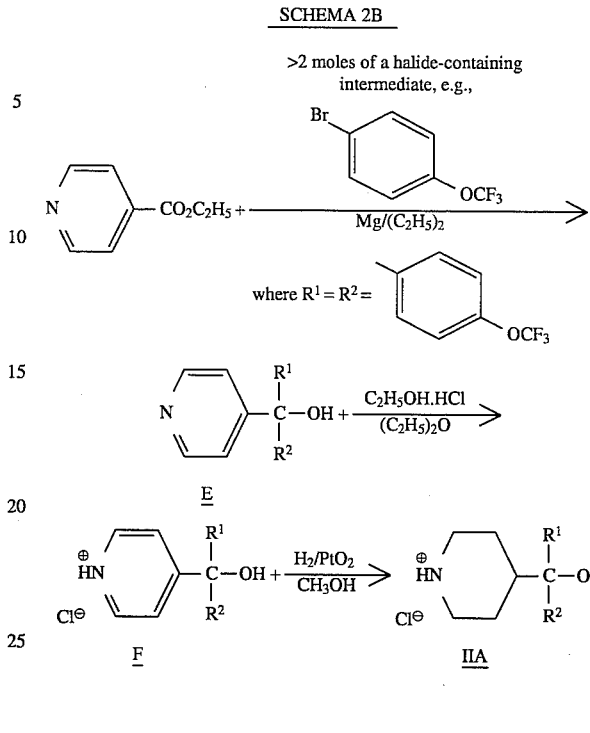
SCHEMA 2C
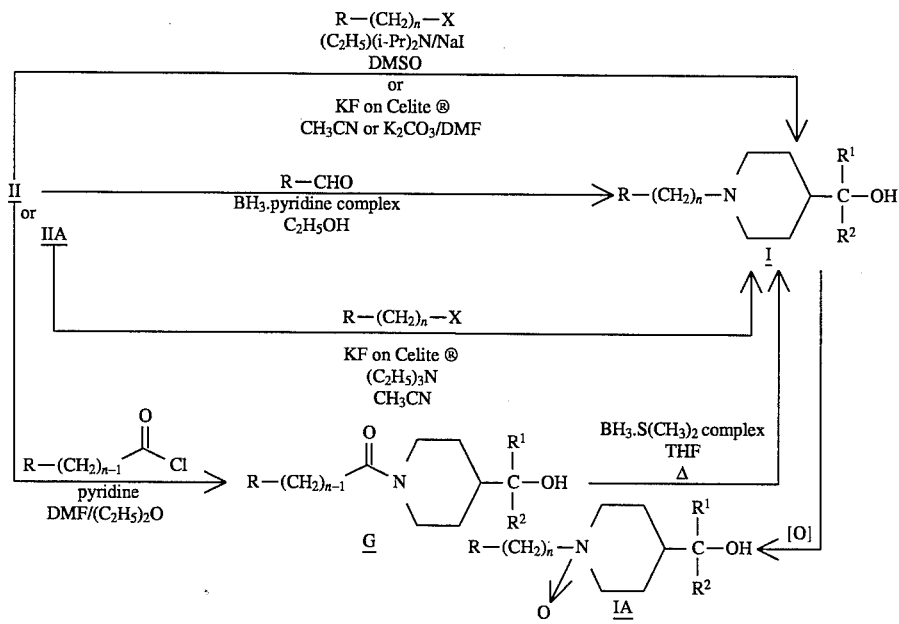

SCHEMA 3

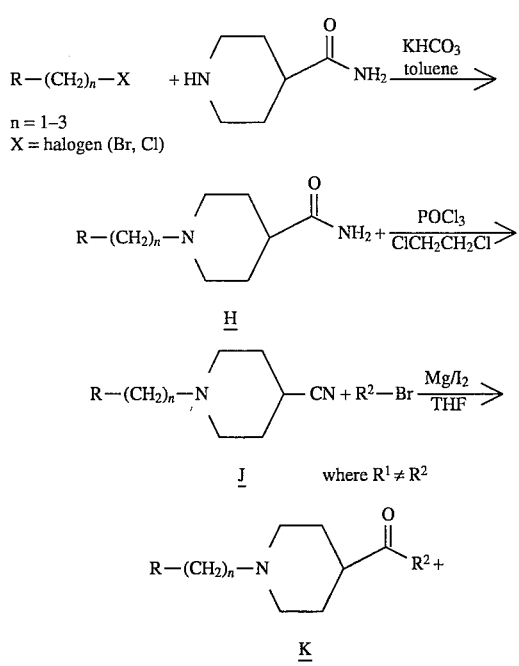

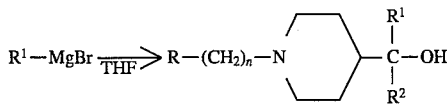

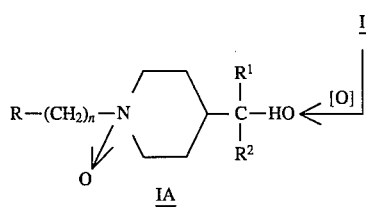

SCHEMA 5

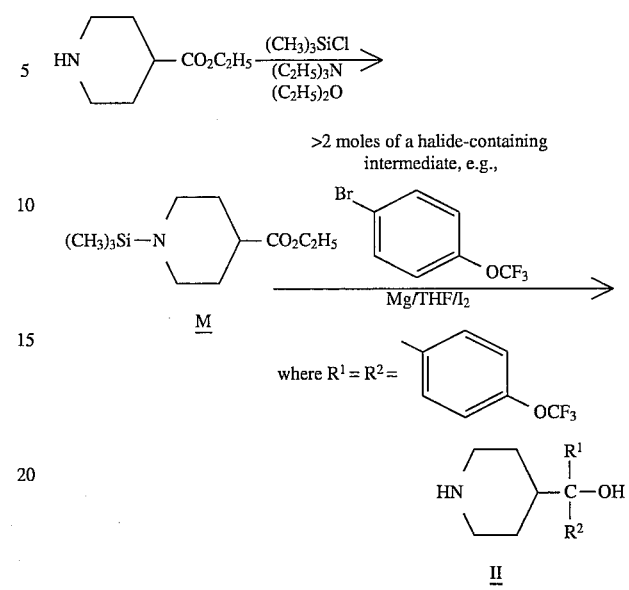

Included within the scope of the present invention are the N-oxides (IA) of the compounds prepared by methods discussed above. The N-oxides (IA) were prepared by treating these compounds, for example, N-[4-(2-propen-1-yloxy)phenylmethyl]-4-[bis(4-trifluoromethoxyphenyl)hydroxymethyl]piperidine (Compound 42) with an oxidizing agent, such as 3-chloroperoxybenzoic acid, yielding the corresponding N-oxide, for example, N-[4-(2-propen-1-yloxy)phenylmethyl]-4-[bis(4-trifluoromethoxyphenyl)hydroxymethyl]piperidine N-oxide (Compound 43). Example 9 provides a detailed description of how this reaction is conducted.

SCHEMA 4

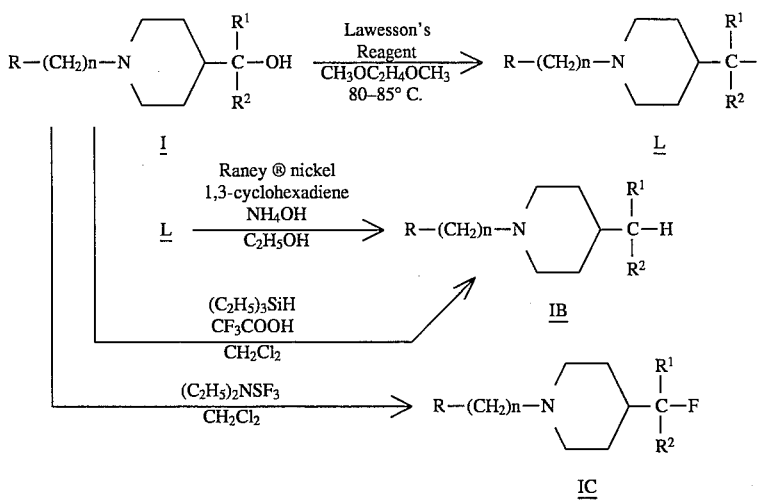

EXAMPLE 1

SYNTHESIS OF N-(4-METHOXYPHENYLMETHYL)-4-[BIS(4-TRIFLUOROMETHOXYPHENYL) HYDROXYMETHYL]PIPERIDINE (COMPOUND 24)

To a stirred mixture of 1.1 grams (0.045 gram-atom) of magnesium turnings in 30 mL of diethyl ether was added dropwise 15 mL of a solution of 11.0 grams (0.045 mole) of 4-trifluoromethoxyphenyl bromide in 30 mL of diethyl ether. Once the reaction had started, the remaining 15 mL of the bromide solution was added portionwise during a 45 minute period. When the reaction subsided, a solution of 5.0 grams (0.018 mole) of ethyl N-(4-methoxyphenylmethyl)piperidin-4-ylcarboxylate in 20 mL of diethyl ether was added dropwise during a five minute period. Upon completion of the addition, the reaction mixture was heated to reflux, where it stirred for about 30 minutes. The reaction mixture was then allowed to cool to ambient temperature, where it stirred for about 18 hours. After this time an aqueous solution saturated with ammonium chloride was added dropwise to quench the reaction. The mixture was then partitioned between water and diethyl ether. The diethyl ether layer was separated and washed first with a solution saturated with sodium chloride and then with water. The organic layer was dried with magnesium sulfate and filtered. The filtrate was concentrated under reduced pressure to a residual oil. The oil was subjected to column chromatography on silica gel, with 10% diethyl ether in hexane, 100% diethyl ether, and 10% methanol in diethyl ether as eluants. The product-containing fractions were combined and concentrated under reduced pressure, yielding 6.7 grams of N-(4-methoxyphenylmethyl)-4-[bis(4-trifluoromethoxyphenyl)hydroxymethyl]piperidine, mp 86°–96° C. The NMR spectrum was consistent with the proposed structure.

EXAMPLE 2

SYNTHESIS OF N-(4-PHENOXYPHENYLMETHYL)-4-[BIS(4-TRIFLUOROMETHOXYPHENYL) HYDROXYMETHYL]PIPERIDINE (COMPOUND 60)

Step A

Synthesis of ethyl N-(4-phenoxyphenylmethyl)piperidin-4-ylcarboxylate as an intermediate To a stirred solution of 5.0 grams (0.025 mole) of 4-phenoxybenzaldehyde and 4.0 grams (0.025 mole) of ethyl piperidin-4-ylcarboxylate in 25 mL of methanol was added 1.6 grams (0.025 mole) of sodium cyanoborohydride in one portion. Upon completion of addition, a methanolic solution saturated with hydrogen chloride was added dropwise until the pH of the reaction mixture was about 6.0. The reaction mixture was then stirred at ambient temperature for about 22 hours, after which the pH was again adjusted to about 5.5–6.0 with additional methanolic hydrogen chloride solution. The reaction mixture was poured into 350 mL of aqueous 0.1M potassium hydroxide solution. The mixture was extracted with three 125 mL portions of diethyl ether, and the combined extracts were washed with one portion of an aqueous solution saturated with sodium chloride. The organic layer was dried with sodium sulfate and filtered. The filtrate was concentrated under reduced pressure to a residue, which was subjected to column chromatography on silica gel, with 1:1 ethyl acetate/hexane as the eluant. The product-containing fractions were combined and concentrated, yielding 5.9 grams of ethyl N-(4-phenoxyphenylmethyl)piperidin-4-ylcarboxylate. The NMR spectrum was consistent with the proposed structure.

Step B

Synthesis of N-(4-phenoxyphenylmethyl)-4-[bis(4-trifluoromethoxyphenyl)hydroxymethyl]piperidine (Compound 60)

This compound was prepared in a manner analogous to that of Example 1, with 2.0 grams (0.006 mole) of ethyl N-(4-phenoxyphenylmethyl)piperidin-4-ylcarboxylate, 7.1 grams (0.029 mole) of 4-trifluoromethoxyphenyl bromide, and 0.7 gram (0.030 gram-atom) of magnesium turnings in diethyl ether as the reagents. This reaction differed from Example 1 in that a small amount (10 drops) of 1,2-dibromoethane was used to initiate the Grignard reaction. The yield of N-(4-phenoxyphenylmethyl)-4-[bis(4-trifluoromethoxyphenyl)hydroxymethyl]piperidine was 0.7 gram. The NMR spectrum was consistent with the proposed structure.

EXAMPLE 3

SYNTHESIS OF N-[2-(4-METHOXYPHENYL)ETHYL]-4-[BIS(4-TRIFLUOROMETHOXYPHENYL) HYDROXYMETHYL]PIPERIDINE (COMPOUND 25)

Step A

Synthesis of ethyl N-[2-(4-methoxyphenyl)ethyl]piperidin-4-ylcarboxylate as an intermediate The reaction conditions for N-alkylation taught by G. D. Maynard et al., Bioorganic & Medicinal Chemistry Letters, 3(4), pp. 753–756, 1993, were used in the following preparation. A stirred mixture of 5.0 grams (0.032 mole) of ethyl piperidin-4-ylcarboxylate, 5.4 grams (0.032 mole) of 1-(2-chloroethyl)-4-methoxybenzene and 4.4 grams (0.032 mole) of potassium carbonate in 50 mL of dried N,N-dimethylformamide was heated at 70° C. for about 16 hours. After this time the reaction mixture was cooled and partitioned between diethyl ether and water. The organic layer was separated and washed with water and then with an aqueous solution saturated with sodium chloride. The organic layer was dried with magnesium sulfate and filtered. The filtrate was concentrated under reduced pressure to a residue, which was subjected to column chromatography on silica gel, with diethyl ether/hexane mixtures as eluants. The product-containing fractions were combined and concentrated under reduced pressure, yielding 2.4 grams of ethyl N-[2-(4-methoxyphenyl)ethyl]piperidin-4-ylcarboxylate. The NMR spectrum was consistent with the proposed structure.

Step B

Synthesis of N-[2-(4-methoxyphenyl)ethyl]-4-[bis(4-trifluoromethoxyphenyl)hydroxymethyl]piperidine (Compound 25)

This compound was prepared in a manner analogous to that of Example 1, with 1.6 grams (0.005 mole) of ethyl N-[2-(4-methoxyphenyl)ethyl]piperidin-4-ylcarboxylate, 2.4 grams (0.010 mole) of 4-trifluoromethoxyphenyl bromide, and 0.3 gram (0.011 gram-atom) of magnesium turnings in about 35 mL of diethyl ether as reagents. This reaction differed from Example 1 in that once the Grignard reaction commenced, the ethyl N-[2-(4-methoxyphenyl)ethyl]piperidin-4-ylcarboxylate was added to the diethyl ether solution of 4-trifluoromethoxyphenyl bromide. The combination was then added dropwise to the reaction mixture, thereby introducing the piperidin-4-ylcarboxylate to the reaction mixture as the Grignard reagent was forming. Upon completion of addition, the reaction mixture was stirred at ambient temperature for about 18 hours. After this time an aqueous solution saturated with ammonium chloride was added dropwise to quench the reaction. The reaction mixture was then extracted with methylene chloride. The combined extracts were washed with a dilute aqueous solution of hydrochloric acid and then with an aqueous solution saturated with sodium chloride. The organic layer was dried with magnesium sulfate and filtered. The filtrate was concentrated under reduced pressure to a residue, which was subjected to column chromatography on silica gel, with hexane/diethyl ether and ethyl acetate/methanol combinations as eluants. A second column chromatography on silica gel was required, with diethyl ether as the eluant, to afford pure product. The product-containing fractions were combined and concentrated under reduced pressure, yielding 0.3 gram of N-[2-(4-methoxyphenyl)ethyl]-4-[bis(4-trifluoromethoxyphenyl)hydroxymethyl]piperidine. The NMR spectrum was consistent with the proposed structure.

EXAMPLE 4

SYNTHESIS OF N-(4-PROPOXYPHENYLMETHYL)-4-[(4-TRIFLUOROMETHOXYPHENYL)(4-CHLOROPHENYL)HYDROXYMETHYL]PIPERIDINE (COMPOUND 7)

Step A

Synthesis of 4-cyano-N-(4-propoxyphenylmethyl)piperidine as an intermediate

The method taught by R. A. Farr et al, J. Org. Chem. 1981, 46, 1212–1215, was used in the following two-step preparation. A vigorously stirred solution of 16.5 grams (0.129 mole) of 4-aminocarbonylpiperidine, 25.0 grams (0.135 mole) of 4-propoxyphenylmethyl chloride, and 19.4 grams (0.193 mole) of potassium bicarbonate in 200 mL of toluene was heated at reflux for 6.5 hours. The reaction mixture was then cooled, water was added, and the mixture was extracted with ethyl acetate. The extract was washed with two portions of an aqueous solution saturated with sodium chloride. The organic layer was dried with sodium sulfate and filtered. The filtrate was concentrated under reduced pressure to a solid residue, which was slurried in pentane and collected by filtration, yielding 28.2 grams of 4-aminocarbonyl-N-(4-propoxyphenylmethyl)piperidine, mp 142°–146° C. The NMR spectrum was consistent with the proposed structure.

A mixture of 27.0 grams (0.10 mole) of 4-aminocarbonyl-N-(4-propoxyphenylmethyl)piperidine in 200 mL of 1,2-dichloroethane was stirred at ambient temperature, and 8.0 grams (0.14 mole) of sodium chloride, followed by 9.2 grams (0.06 mole) of phosphorous oxychloride were added. The reaction mixture was then warmed to reflux, where it stirred for about 1.75 hours. The reaction mixture was cooled to ambient temperature and about 350 mL of water was added. The aqueous layer was separated, washed with two portions of diethyl ether, and then made basic with aqueous 5% sodium hydroxide. The mixture was extracted with two portions of diethyl ether. The combined extracts were washed with an aqueous solution saturated with sodium chloride. The organic layer was dried with sodium sulfate and poured through a pad of silica gel. The silica gel pad was washed with 1000 mL of diethyl ether. The combined eluants were concentrated under reduced pressure, yielding 14.5 grams of 4-cyano-N-(4-propoxyphenylmethyl)piperidine. The NMR spectrum was consistent with the proposed structure.

Step B

Synthesis of N-(4-propoxyphenylmethyl)-4-(4-trifluoromethoxyphenylcarbonyl)piperidine as an intermediate This compound was prepared in a manner analogous to that of Step B of Example 3, with 5.0 grams (0.019 mole) of 4-cyano-N-(4-propoxyphenylmethyl)piperidine, 10.7 grams (0.045 mole) of 4-trifluoromethoxyphenyl bromide, 1.1 grams (0.045 gram-atom) of magnesium turnings, and iodine (catalyst) in 155 mL of tetrahydrofuran as the reagents. The yield of N-(4-propoxyphenylmethyl)-4-(4-trifluoromethoxyphenylcarbonyl)piperidine was 3.9 grams. The NMR spectrum was consistent with the proposed structure.

Step C

Synthesis of N-(4-propoxyphenylmethyl)-4-[(4-trifluoromethoxyphenyl)(4-chlorophenyl)hydroxymethyl]piperidine (Compound 7)

A solution of 0.6 gram (0.0014 mole) of N-(4-propoxyphenylmethyl)-4-(4-trifluoromethoxyphenylcarbonyl)piperidine in 15 mL of tetrahydrofuran was stirred, and to the stirred solution was slowly added 1.8 mL of 4-chlorophenylmagnesium bromide (0.0018 mole-1M in diethyl ether). Upon completion of the addition, the reaction mixture was warmed to 65° C., where it was stirred for 3.5 hours. After this time the reaction mixture was allowed to cool to ambient temperature, where it stirred for about 18 hours. The reaction mixture was then poured into a mixture of 50 mL of ice and 75 mL of an aqueous solution saturated with ammonium chloride. The mixture was stirred until the ice melted and then extracted with ethyl acetate. The extract was dried with sodium sulfate and filtered. The filtrate was concentrated under reduced pressure to a residue, which was dissolved in boiling petroleum ether and treated with decolorizing carbon. Diatomaceous earth was stirred in, and the mixture was filtered through a pad of activated magnesium silicate. The magnesium silicate pad was washed with 30% acetone in methylene chloride. The filtrate and wash were combined and concentrated under reduced pressure, yielding 0.4 gram of N-(4-propoxyphenylmethyl)-4-[(4-trifluoromethoxyphenyl)(4-chlorophenyl)hydroxymethyl]piperidine. The NMR spectrum was consistent with the proposed structure.

EXAMPLE 5

SYNTHESIS OF N-[4-(2-PROPEN-1-YLOXY)PHENYLMETHYL]-4-[BIS(4-TRIFLUOROMETHOXYPHENYL)HYDROXYMETHYL]PIPERIDINE (COMPOUND 42)

Step A

Synthesis of ethyl N-[4-(2-propen-1-yloxy)phenylmethyl]piperidin-4-ylcarboxylate as an intermediate The reaction conditions taught by A. E. Moormann, Syn. Comm., 23(6), 789–795 (1993) were used in the following preparation. To a stirred solution of 4.8 grams (0.030 mole)

of ethyl piperidin-4-ylcarboxylate and 4.9 grams (0.030 mole) of 4-(2-propen-1-yloxy)benzaldehyde in 50 mL of ethanol was added 3.8 mL (0.030 mole) of borane-pyridine complex. Upon completion of addition, the reaction mixture was stirred at ambient temperature for about 18 hours. The reaction mixture was then taken up in water and extracted with methylene chloride. The organic layer was washed with water and dried with magnesium sulfate. The mixture was filtered and the filtrate concentrated under reduced pressure, yielding 9.0 grams of ethyl N-[4-(2-propen-1-yloxy)phenylmethyl]piperidin-4-ylcarboxylate. The NMR spectrum was consistent with the proposed structure.

Step B

Synthesis of
N-[4-(2-propen-1-yloxy)phenylmethyl]-4-[bis(4-trifluoromethoxyphenyl)hydroxymethyl]piperidine
(Compound 42)

This compound was prepared in a manner analogous to that of Step B of Example 2, with 3.8 grams (0.013 mole) of ethyl N-[4-(2-propen-1-yloxy)phenylmethyl]piperidin-4-ylcarboxylate, 15.0 grams (0.063 mole) of 4-trifluoromethoxyphenyl bromide, 1.5 grams (0.060 gram-atom) of magnesium turnings and about 10 drops of 1,2-dibromoethane in diethyl ether as the reagents. The yield of N-[4-(2-propen-1-yloxy)phenylmethyl]-4-[bis(4-trifluoromethoxyphenyl)hydroxymethyl]piperidine was about 1.3 gram. The NMR spectrum was consistent with the proposed structure.

EXAMPLE 6

SYNTHESIS OF N-(2,6-DIMETHOXYPHENYLMETHYL)-4-[BIS(4-TRIFLUOROMETHOXYPHENYL) HYDROXYMETHYL]PIPERIDINE (COMPOUND 38)

Step A

Synthesis of 2,6-dimethoxyphenylmethyl bromide as an intermediate

After a mixture of 5.7 grams (0.034 mole) of 2,6-dimethoxyphenylmethanol in 40 mL of concentrated hydrobromic acid was stirred at ambient temperature for about one hour, the reaction mixture was taken up in diethyl ether. Solid sodium chloride was added to the mixture to obtain a phase separation. The organic layer was separated and concentrated under reduced pressure, yielding about 4.7 grams of 2,6-dimethoxyphenylmethyl bromide. This compound was used immediately in the next reaction.

Step B

Synthesis of ethyl
N-(2,6-dimethoxyphenylmethyl)piperidin-4-ylcarboxylate as an intermediate A stirred solution of 4.7 grams (0.020 mole) of 2,6-dimethoxyphenylmethyl bromide, 3.2 grams (0.020 mole) of ethyl piperidin-4-ylcarboxylate, and 23.5 grams (0.200 mole) of 50% potassium fluoride on Celite® filter aid in 100 mL of acetonitrile was heated at reflux for about 18 hours, after which the reaction mixture was cooled and filtered. The filtrate was concentrated under reduced pressure to a residue, which was subjected to column chromatography on silica gel, with mixtures of ethyl acetate in hexane as eluants. The product-containing fractions were combined and concentrated under reduced pressure to a residue. The residue was analyzed using thin layer chromatography, which indicated that the residue was impure. The residue was again subjected to column chromatography on silica gel, with mixtures of ethyl acetate in hexane and methanol in ethyl acetate as eluants. The product-containing fractions were combined and concentrated under reduced pressure, yielding about one gram of ethyl N-(2,6-dimethoxyphenylmethyl)piperidin-4-ylcarboxylate. The NMR spectrum was consistent with the proposed structure.

Step C

Synthesis of
N-(2,6-dimethoxyphenylmethyl)-4-[bis(4-trifluoromethoxyphenyl)hydroxymethyl]piperidine
(Compound 38)

This compound was prepared in a manner analogous to that of Step B of Example 2, with 1.0 gram (0.003 mole) of ethyl N-(2,6-dimethoxyphenylmethyl)piperidin-4-ylcarboxylate, 3.7 grams (0.015 mole) of 4-trifluoromethoxyphenyl bromide, 0.4 gram (0.015 gram-atom) of magnesium turnings and 10 drops of 1,2-dibromoethane in 20 mL of diethyl ether as reagents, yielding about 0.9 gram of N-(2,6-dimethoxyphenylmethyl)-4-[bis(4-trifluoromethoxyphenyl)hydroxymethyl]piperidine. The NMR spectrum was consistent with the proposed structure.

EXAMPLE 7

SYNTHESIS OF N-(4-ETHOXYCARBONYLPHENYLMETHYL)-4-[BIS(4-TRIFLUOROMETHOXYPHENYL) HYDROXYMETHYL]PIPERIDINE (COMPOUND 57)

Step A

Synthesis of N-(diethylaminocarbonyl)-4-[bis(4-trifluoromethoxyphenyl)hydroxymethyl]piperidine as an intermediate This compound was prepared in a manner analogous to that of Example 1, with 25.7 grams (0.10 mole) of ethyl N-(diethylaminocarbonyl)piperidin-4-ylcarboxylate, 61.1 grams (0.25 mole) of 4-trifluoromethoxyphenyl bromide, and 5.7 grams (0.23 gram-atom) of magnesium turnings in 390 mL of tetrahydrofuran as reagents, yielding 43.8 grams of N-(diethylaminocarbonyl)-4-[bis(4-trifluoromethoxyphenyl)hydroxymethyl]piperidine, mp 165°–166° C. The NMR spectrum was consistent with the proposed structure.

Step B

Synthesis of 4-[bis(4-trifluoromethoxyphenyl)
hydroxymethyl]piperidine as an intermediate, and
N-methyl-4-[bis(4-trifluoromethoxyphenyl)
hydroxymethyl]piperidine (Compound 9)

A stirred slurry of 7.7 grams (0.203 mole) of lithium aluminum hydride in 150 mL of dry tetrahydrofuran was cooled to about 15° C., and a solution of 43.3 grams (0.081 mole) of N-(diethylaminocarbonyl)-4-[bis(4-trifluoromethoxyphenyl)hydroxymethyl]piperidine in about 250 mL of dry tetrahydrofuran was added dropwise during a 15 minute period. Upon completion of addition, the reaction mixture was stirred at about 15°–20° C. for five minutes and then warmed to reflux, where it was stirred for about 18 hours. The reaction mixture was allowed to cool to ambient temperature, where it stood for 24 hours. The reaction mixture was cooled to 0°–10° C., and 7.7 mL of water, 23 mL of aqueous 3N sodium hydroxide, and 7.7 mL of water were in turn added dropwise during a 30 minute period. The reaction mixture temperature was maintained at 0°–10° C. throughout these additions. Upon completion of the additions, the reaction mixture was stirred for about 75 minutes and filtered, yielding a sticky solid. The solid was stirred with a small amount of tetrahydrofuran and filtered. The filtrate was concentrated under reduced pressure at 50°–55° C. until the viscous residue solidified. The solid was dissolved in warm (31°–33° C.) petroleum ether, and then the solution was cooled in a dry ice/acetone bath. The resultant solid, which precipitated on the walls of the flask, was collected by first decanting away the petroleum ether and then slurrying the solid in diethyl ether. The mixture was concentrated under reduced pressure, yielding 6.8 grams of solid residue. A sample of the solid was subjected to NMR analysis. The NMR spectrum was inconclusive, and the solid was discarded. The petroleum ether decantate was then concentrated under reduced pressure, yielding about 26 grams of sticky residue. The residue was dissolved in warm chloroform and subjected to column chromatography on silica gel. Elution was started with 20% methanol in chloroform. Appropriate fractions, identified by thin layer chromatography, were combined and concentrated under reduced pressure, yielding 9.4 grams of solid, mp 123°–128° C. NMR and mass spectroscopy indicated that this solid was N-methyl-4-[bis(4-trifluoromethoxyphenyl)hydroxymethyl]piperidine (Compound 9). The eluant was changed from 20% methanol in chloroform to 30% methanol in chloroform, and the column chromatography was continued. Other fractions, also identified by thin layer chromatography, were combined and concentrated under reduced pressure, yielding 7.4 grams of solid. NMR and mass spectrophotometry indicated that this solid was the desired 4-[bis(4-trifluoromethoxyphenyl)hydroxymethyl]piperidine intermediate.

Step C

Synthesis of
N-(4-ethoxycarbonylphenylmethyl)-4-[bis(4-trifluoromethoxyphenyl)hydroxymethyl]piperidine
(Compound 57)

By the method of D. A. Walsh et al., J. Med. Chem. 1989, 32, 105–118, a stirred mixture of 0.5 gram (0.001 mole) of 4-[bis(4-trifluoromethoxyphenyl)hydroxymethyl]piperidine (prepared in Step B of this Example), 0.3 gram (0.001 mole) of ethyl 4-bromomethylbenzoate, and 0.5 gram (0.004 mole) of potassium carbonate in 15 mL of N,N-dimethylformamide was heated to 95° C., where it stirred for about 16 hours. After this time the reaction mixture was poured into 50 mL of ice-water, where it stirred for 15 minutes. The mixture was extracted with three 75 mL portions of diethyl ether. The combined extracts were washed with two 75 mL portions of an aqueous solution saturated with sodium chloride. The organic layer was dried with magnesium sulfate and filtered. The filtrate was concentrated under reduced pressure, yielding 0.1 gram of residual oil. The aqueous layer was reextracted with three 100 mL portions of ethyl acetate. The combined extracts were washed with one 100 mL portion of an aqueous solution saturated with sodium chloride. The organic layer was dried with sodium sulfate and filtered. The filtrate was concentrated under reduced pressure, yielding 0.8 gram of residual oil, which was subjected to column chromatography on silica gel, with 30% ethyl acetate in heptane as the eluant. The product-containing fractions were combined and concentrated under reduced pressure, yielding 0.3 gram of N-(4-ethoxycarbonylphenylmethyl)-4-[bis(4-trifluoromethoxyphenyl)hydroxymethyl]piperidine. The NMR spectrum was consistent with the proposed structure.

EXAMPLE 8

SYNTHESIS OF
N-(3-CHLORO-4-METHOXYPHENYLMETHYL)-4-[BIS(4-TRIFLUOROMETHOXYPHENYL)HYDROXYMETHYL]PIPERIDINE (COMPOUND 44)

Step A

Synthesis of
N-(3-chloro-4-methoxyphenylcarbonyl)-4-[bis(4-trifluoromethoxyphenyl)hydroxymethyl]piperidine
as an intermediate A stirred solution of 0.22 gram (0.0012 mole) of 3-chloro-4-methoxybenzoic acid in a small amount of tetrahydrofuran and chloroform was cooled to 0° C., and 0.12 mL (0.0014 mole) of oxalyl chloride was added dropwise. Upon completion of addition, the reaction mixture was allowed to warm to ambient temperature, where it was stirred for about 3.5 hours. After this time the reaction mixture was concentrated under reduced pressure, yielding 3-chloro-4-methoxybenzoyl chloride, which was dissolved in a small amount of tetrahydrofuran for later use.

In a separate reaction vessel, a solution of 0.5 gram (0.0012 mole) of 4-[bis(4-trifluoromethoxyphenyl)hydroxymethyl]piperidine (prepared in Step B of Example 7) and 0.09 gram (0.0012 mole) of pyridine in a small amount of tetrahydrofuran was stirred, and the solution of 3-chloro-4-methoxybenzoyl chloride in tetrahydrofuran, prepared above, was added. Upon completion of addition, the reaction mixture was stirred at ambient temperature for about 15 minutes and then filtered to remove a white solid. The filtrate was stirred for about 18 hours and then was partitioned between ethyl acetate and an aqueous solution saturated with sodium chloride. The organic layer was separated and passed through a column of silica gel. Elution was accomplished with 50% ethyl acetate in hexane. The product-containing fractions were combined and concentrated under reduced pressure, yielding 0.62 gram of N-(3-chloro-4-methoxyphenylcarbonyl)-4-[bis(4-trifluoromethoxyphenyl)hydroxymethyl]piperidine. The NMR spectrum was consistent with the proposed structure.

Step B

Synthesis of
N-(3-chloro-4-methoxyphenylmethyl)-4-[bis(4-trifluoromethoxyphenyl)hydroxymethyl]piperidine
(Compound 44)

To a stirred solution of 0.50 gram (0.0008 mole) of N-(3-chloro-4-methoxyphenylcarbonyl)-4-[bis(4-trifluoromethoxyphenyl)hydroxymethyl]piperidine in 5 mL of tetrahydrofuran was slowly added 0.42 mL (0.0040 mole) of borane-methyl sulfide complex (10M in $BH_3$). Upon completion of addition, the reaction mixture was stirred at ambient temperature for about 18 hours. The reaction mixture was then cooled in an ice-bath, and 20 mL of methanol was added slowly to quench the reaction. The reaction mixture was then concentrated under reduced pressure to a residue. Another 20 mL of methanol was stirred with the residue, and this was concentrated under reduced pressure to the residue. The process of adding 20 mL of methanol and concentrating the solution to the residue was repeated once more. The residue was partitioned between ethyl acetate and water, and the mixture was stirred for 15 minutes. The organic layer was separated, washed with an aqueous solution saturated with sodium chloride, and then dried with sodium sulfate. The mixture was filtered and concentrated under reduced pressure to a residue, which was subjected to column chromatography on silica gel, with mixtures of ethyl acetate in hexane as eluants. The product-containing fractions were combined and concentrated under reduced pressure, yielding 0.13 gram of N-(3-chloro-4-methoxyphenylmethyl)-4-[bis(4-trifluoromethoxyphenyl)hydroxymethyl]piperidine. The NMR spectrum was consistent with the proposed structure.

EXAMPLE 9

SYNTHESIS OF
N-[4-(2-PROPEN-1-YLOXY)PHENYLMETHYL]-4-[BIS(4-TRIFLUOROMETHOXYPHENYL)HYDROXYMETHYL]PIPERIDINE N-OXIDE
(COMPOUND 43)

To a stirred solution of 0.5 gram (0.0008 mole) of N-[4-(2-propen-1-yloxy)phenylmethyl]-4-[bis(4-trifluoromethoxyphenyl)hydroxymethyl]piperidine (Compound 42, prepared in Example 5) in 10 mL of chloroform was added 0.3 gram (0.0008 mole) of 50% 3-chloroperoxybenzoic acid. Upon completion of addition, the reaction mixture was stirred at ambient temperature for about 2 hours. After this time the reaction mixture was washed, first, with an aqueous solution saturated with sodium bicarbonate, and then with an aqueous solution saturated with sodium chloride. The organic layer was dried with magnesium sulfate and filtered. The filtrate was concentrated under reduced pressure to a residue, which was subjected to column chromatography on silica gel, with mixtures of ethyl acetate and hexane as eluants. The product-containing fractions were combined and concentrated under reduced pressure to a residue. The residue was concentrated further under high vacuum, yielding about 0.2 gram of N-[4-(2-propen-1-yloxy)phenylmethyl]-4-[bis(4-trifluoromethoxyphenyl)hydroxymethyl]piperidine N-oxide. The NMR spectrum was consistent with the proposed structure.

EXAMPLE 10

SYNTHESIS OF
N-(4-PROPOXYPHENYLMETHYL)-4-[BIS(4-TRIFLUOROMETHOXYPHENYL)HYDROXYMETHYL]PIPERIDINE (COMPOUND 29)

Step A

Synthesis of ethyl
N-(4-propoxyphenylmethyl)piperidin-4-ylcarboxylate
as an intermediate This compound was prepared in a manner analogous to that of Step A of Example 2, with 5.3 grams (0.032 mole) of 4-propoxybenzaldehyde, 5.0 grams (0.032 mole) of ethyl piperidin-4-ylcarboxylate, 2.0 grams (0.032 mole) of sodium cyanoborohydride, and methanolic hydrogen chloride solution in 30 mL of methanol as the reagents. The yield of ethyl N-(4-propoxyphenylmethyl)piperidin-4-ylcarboxylate was 2.6 grams. The NMR spectrum was consistent with the proposed structure.

Step B

Synthesis of N-(4-propoxyphenylmethyl)-4-[bis(4-trifluoromethoxyphenyl)hydroxymethyl]piperidine
(Compound 29)

This compound was prepared in a manner analogous to that of Example 1, with 1.5 grams (0.005 mole) of ethyl N-(4-propoxyphenylmethyl)piperidin-4-ylcarboxylate, 3.6 grams (0.015 mole) of 4-trifluoromethoxyphenyl bromide, 0.4 gram (0.015 gram-atom) of magnesium turnings, and iodine (catalyst) in 40 mL of tetrahydrofuran as the reagents. The yield of N-(4-propoxyphenylmethyl)-4-[bis(4-trifluoromethoxyphenyl)hydroxymethyl]piperidine was 1.1 grams. The NMR spectrum was consistent with the proposed structure.

EXAMPLE 11

SYNTHESIS OF
N-[4-(2-PROPYN-1-YLOXY)PHENYLMETHYL]-4-[BIS(4-TRI-FLUOROMETHOXYPHENYL)HYDROXYMETHYL]PIPERIDINE (COMPOUND 65)

Step A

Synthesis of 4-[bis(4-trifluoromethoxyphenyl)
hydroxymethyl]pyridine as an intermediate This compound was prepared in a manner analogous to that of Example 1, with 10.9 grams (0.067 mole) of ethyl pyridin-4-ylcarboxylate, 40.3 grams (0.167 mole) of 4-trifluoromethoxyphenyl bromide, and 4.1 grams (0.023 gram-atom) of magnesium turnings in about 275 mL of diethyl ether as reagents. The crude product was subjected to column chromatography on silica gel, with mixtures of 20–90% ethyl acetate in hexane. The product-containing fractions were combined and concentrated under reduced pressure to a residual solid. The solid was triturated three times with hexane, yielding 17.7 grams of 4-[bis(4-trifluoromethoxyphenyl)hydroxymethyl]pyridine. The NMR spectrum was consistent with the proposed structure.

Step B

Synthesis of 4-[bis(4-trifluoromethoxyphenyl)
hydroxymethyl]pyridine hydrochloride as an
intermediate To a stirred solution of 17.6 grams (0.041 mole) of 4-[bis(4-trifluoromethoxyphenyl)hydroxymethyl]pyridine in 200 mL of diethyl ether was added about 20 mL of an ethanolic solution saturated with hydrogen chloride. Upon completion of addition, the reaction mixture was cooled to promote precipitation of the product. When the solid precipitate did not appear, the reaction mixture was slowly concentrated during a one hour period by passing a stream of nitrogen gas over the reaction mixture. During this time the solid precipitate still did not appear. Additional diethyl ether was added, and the stream of nitrogen gas over the reaction mixture was continued. The reaction mixture was finally concentrated under reduced pressure to near dryness, at which point a solid precipitate formed. The solid was slurried in about 10 mL of fresh diethyl ether and filtered to yield 9.3 grams of 4-[bis(4-trifluoromethoxyphenyl)hydroxymethyl]pyridine hydrochloride. The NMR spectrum was consistent with the proposed structure.

Step C

Synthesis of 4-[bis(4-trifluoromethoxyphenyl) hydroxymethyl]piperidine hydrochloride as an intermediate A solution of 2.0 grams (0.004 mole) of 4-[bis(4-trifluoromethoxyphenyl)hydroxymethyl]pyridine hydrochloride and a catalytic amount of platinum oxide in 125 mL of methanol was hydrogenated at 50 psi of hydrogen in a Parr hydrogenator. The completion of hydrogenation required about two hours. After this time, the reaction mixture was filtered to remove the catalyst. The filtrate was concentrated to about 20 mL in volume, 80 mL of diethyl ether was added, and the solution was placed in a refrigerator. The resultant solid precipitate was collected by filtration, yielding about 0.4 gram of product. The filtrate was concentrated under reduced pressure, yielding an additional 1.9 grams of product. The two solid fractions were combined, yielding 2.3 grams of 4-[bis(4-trifluoromethoxyphenyl)hydroxymethyl]piperidine hydrochloride. The NMR spectrum was consistent with the proposed structure.

Step D

Synthesis of N-[4-(2-propyn-1-yloxy)phenylmethyl]-4-[bis(4-trifluoromethoxyphenyl)hydroxymethyl]piperidine (Compound 65)

A stirred mixture of 0.8 gram (0.0016 mole) of 4-[bis(4-trifluoromethoxyphenyl)hydroxymethyl]piperidine hydrochloride, 0.3 gram (0.0016 mole) of 4-(2-propyn-1-yloxy)phenylmethyl chloride and 0.5 gram (0.0079 mole) of potassium fluoride on Celite® filter aid in 50 mL of acetonitrile was heated at reflux for about 1.3 hours. After this time 0.5 mL (excess) of triethylamine was added, and the reaction mixture became homogeneous. Upon completion of addition, the reaction mixture was heated at reflux for an additional 18 hours. After this time the reaction mixture was cooled, filtered, and the filtrate concentrated under reduced pressure to a residue, which was subjected to column chromatography on silica gel, with mixtures of 10–70% diethyl ether in hexane as eluants. The product-containing fractions were combined and concentrated under reduced pressure, yielding 0.6 gram of N-[4-(2-propyn-1-yloxy)phenylmethyl]-4-[bis(4-trifluoromethoxyphenyl)hydroxymethyl]piperidine. The NMR spectrum was consistent with the proposed structure.

EXAMPLE 12

SYNTHESIS OF N-[4-(METHYLCARBONYLAMINO) PHENYLMETHYL]-4-[BIS(4-TRIFLUOROMETHOXYPHENYL) HYDROXYMETHYL]PIPERIDINE (COMPOUND 66)

Step A

Synthesis N-phenylmethyl-4-[bis(4-trifluoromethoxyphenyl) hydroxymethyl]piperidine (Compound 13) as an intermediate This compound was prepared in a manner analogous to that of Step B of Example 3, with 6.0 grams (0.024 mole) of ethyl N-phenylmethylpiperidin-4-ylcarboxylate, 1.8 grams (0.073 gram-atom) of magnesium turnings, and 17.5 grams (0.073 mole) of 4-trifluoromethoxyphenyl bromide in about 80 mL of tetrahydrofuran as reagents. The yield of N-phenylmethyl-4-[bis(4-trifluoromethoxyphenyl)hydroxymethyl]piperidine was 9.7 grams. The NMR spectrum was consistent with the proposed structure.

Step B

Synthesis N-phenylmethyl-4-[bis(4-trifluoromethoxyphenyl)hydroxymethyl]piperidine hydrochloride as an intermediate The reaction conditions taught by P. J. Gilligan et al., J. Med. Chem. 1992, 4344–4361, were used in the following two-step preparation. A stirred solution of 1.0 gram (0.002 mole) of N-phenylmethyl-4-[bis(4-trifluoromethoxyphenyl)hydroxymethyl]piperidine in 30 mL of diethyl ether was cooled to 0° C., and hydrogen chloride gas was bubbled in. An oily solid precipitate formed. Upon completion of precipitation, the reaction mixture was taken up in 25 mL of hexane and stored in a refrigerator for about 18 hours. After this time the supernatant liquid was decanted from the precipitate. The precipitate was then stirred with about 20 mL of diethyl ether, and the mixture was concentrated under reduced pressure to a residue. The solid residue was stirred with about 20 mL of hexane, which was then decanted from the solid. The solid was dried under reduced pressure, yielding 0.8 gram of N-phenylmethyl-4-[bis(4-trifluoromethoxyphenyl)hydroxymethyl]piperidine hydrochloride. The NMR spectrum was consistent with the proposed structure.

Step C

Synthesis 4-[bis(4-trifluoromethoxyphenyl) hydroxymethyl]piperidine as an intermediate Under a nitrogen atmosphere, 0.8 gram of 10% palladium on charcoal (catalyst) was placed in the reaction vessel. To this were cautiously added 25 mL of nitrogen-purged methanol, a solution of 0.8 gram (0.001 mole) of N-phenylmethyl-4-[bis(4-trifluoromethoxyphenyl)hydroxymethyl]piperidine hydrochloride in 10 mL of methanol, and then 0.9 gram (0.010 mole) of ammonium formate. Upon completion of addition, the reaction mixture was heated at reflux for about 45 minutes. The reaction mixture was then cooled to ambient temperature and diluted with 1:1-methylene chloride/methanol. The mixture was filtered through a pad of diatomaceous earth/fiberglass, and the filtrate was concentrated at about 30° C. under reduced pressure to a residue. The residue was taken up in about 70 mL of ice/water and made basic with aqueous 5% sodium hydroxide solution. The mixture was extracted with methylene chloride, and the extract was washed with an aqueous solution saturated with sodium chloride. The organic layer was then dried with sodium sulfate. The mixture was filtered, and the filtrate was concentrated under reduced pressure to a residue. The residue was stirred with petroleum ether, and 0.5 gram of solid 4-[bis(4-trifluoromethoxyphenyl)hydroxymethyl]piperidine was collected by filtration. The NMR spectrum was consistent with the proposed structure.

Step D

Synthesis of N-[4-(methylcarbonylamino)phenylmethyl]-4-[bis(4-trifluoromethoxyphenyl) hydroxymethyl]piperidine (Compound 66)

To a stirred solution of 0.4 gram (0.0008 mole) of 4-[bis(4-trifluoromethoxyphenyl)hydroxymethyl]piperidine in 10 mL of dimethyl sulfoxide was added a mixture of 0.2 gram (0.0008 mole) of 4-(methylcarbonylamino)phenylmethyl chloride and 0.6 mL (0.003 mole) of N,N-diisopropylethylamine. Upon completion of addition, the reaction mixture was stirred at ambient temperature for about 18 hours. After this time the reaction mixture was partitioned between an aqueous solution saturated with sodium bicarbonate and ethyl acetate. The organic layer was separated and washed with an aqueous solution saturated with sodium chloride. The organic layer was then concentrated under reduced pressure to a residue, which was subjected to column chromatography on silica gel, with methylene chloride and mixtures of 10–50% acetone in methylene chloride as eluants. The product-containing fractions were combined and concentrated under reduced pressure, yielding about 0.3 gram of N-[4-(methylcarbonylamino)phenylmethyl]-4-[bis(4-trifluoromethoxyphenyl)hydroxymethyl]piperidine. The NMR spectrum was consistent with the proposed structure.

EXAMPLE 13

SYNTHESIS OF N-(4-PROPOXYPHENYLMETHYL)-4-[BIS(4-TRIFLUOROMETHOXYPHENYL) METHYL]PIPERIDINE (COMPOUND 104)

Step A

Synthesis of N-(4-propoxyphenylmethyl)-4-[bis(4-trifluoromethoxyphenyl)mercaptomethyl]piperidine as an intermediate Under a nitrogen atmosphere, a solution of 2.3 grams (0.004 mole) of N-(4-propoxyphenylmethyl)-4-[bis(4-trifluoromethoxyphenyl)hydroxymethyl]piperidine (prepared in Example 10) in about 13.4 mL of 1,2-dimethoxyethane was stirred, and 1.3 grams (0.003 mole) of 2,4-bis(4-methoxyphenyl)-1,3-dithia-2,4-diphosphetane-2,4-disulfide (Lawesson's Reagent) was added. The reaction mixture was then warmed to about 80°–85° C., and an additional 0.3 gram (0.0007 mole) of Lawesson's Reagent was added. The reaction mixture was stirred for 10 minutes, and another 0.3 gram (0.0007 mole) of Lawesson's Reagent was added. After the reaction mixture was stirred for another 10 minutes, a third 0.3 gram (0.0007 mole) amount of Lawesson's Reagent was added. The 1,2-dimethoxyethane solvent was removed by azeotroping it with methylene chloride. The resultant methylene chloride solution was concentrated under reduced pressure to a residue, which was added to the crude product of a previous run (0.001 mole) of this reaction. The combined products were subjected to column chromatography on silica gel, with a 2:1:1 mixture of toluene, methylene chloride, and acetone, respectively, as eluants. The product-containing fractions were combined and concentrated under reduced pressure, yielding about 3.8 grams of impure product. The product was again subjected to column chromatography on silica gel, with methylene chloride and 1–2% mixtures of acetone in methylene chloride as the eluants. The product-containing fractions were combined and concentrated under reduced pressure, yielding 1.2 grams of N-(4-propoxyphenylmethyl)-4-[bis(4-trifluoromethoxyphenyl)mercaptomethyl]piperidine. The NMR spectrum was consistent with the proposed structure.

Step B

Synthesis of N-(4-propoxyphenylmethyl)-4-[bis(4-trifluoromethoxyphenyl)methyl]piperidine as an intermediate (Compound 104)

To a stirred mixture of 15.4 grams (excess) Raney® nickel (50% slurry in water), 7.7 mL of 1,3-cyclohexadiene, and 13.1 mL of concentrated ammonium hydroxide in 105 mL of methanol was added a solution of 0.8 gram (0.0013 mole) of N-(4-propoxyphenylmethyl)-4-[bis(4-trifluoromethoxyphenyl)mercaptomethyl]piperidine in 50 mL of ethanol. Upon completion of addition, the reaction mixture was warmed to reflux, where it was stirred for about 30 minutes. The reaction mixture was then cooled and combined with two small (0.00017 mole each) earlier runs of this reaction. The combination was filtered through a pad of diatomaceous earth. The pad of diatomaceous earth was then washed with ethanol, and the wash and filtrate were combined. The wash/filtrate combination was concentrated under reduced pressure to a residue, which was diluted with ethyl acetate and washed with an aqueous solution saturated with sodium chloride. The organic layer was dried with sodium sulfate and filtered. The filtrate was concentrated under reduced pressure to a residue, which was subjected to column chromatography on silica gel, with methylene chloride and 2–4% acetone in methylene chloride as the eluants. The product-containing fractions were combined and concentrated under reduced pressure, yielding 0.3 gram of N-(4-propoxyphenylmethyl)-4-[bis(4-trifluoromethoxyphenyl)methyl]piperidine. The NMR spectrum was consistent with the proposed structure.

EXAMPLE 14

SYNTHESIS OF N-(4-METHOXYPHENYLMETHYL)-4-[BIS(4-ETHYLPHENYL)METHYL]PIPERIDINE (COMPOUND 103)

To a stirred solution of 1.0 gram (0.002 mole) of N-(4-methoxyphenylmethyl)-4-[bis(4-ethylphenyl)hydroxymethyl]piperidine (prepared in the manner of Example 1) in 10 mL of methylene chloride was slowly added 1.1 mL (0.007 mole) of triethylsilane, followed by 1.0 mL (0.013 mole) of trifluoroacetic acid. The reaction mixture was then stirred at ambient temperature during a five hour period. After this time the reaction mixture was neutralized with solid sodium carbonate. The mixture was then partitioned between 100 mL of methylene chloride and 50 mL of water. The organic layer was separated and washed with two 50 mL portions of an aqueous solution saturated with sodium chloride. The organic layer was then dried with sodium sulfate and filtered. The filtrate was concentrated under reduced pressure to a residue, which was purified by subjecting it to preparative thin layer chromatography, with 25% acetone in methylene chloride as the eluant, yielding about 0.5 gram of N-(4-methoxyphenylmethyl)-4-[bis(4-ethylphenyl)methyl]piperidine. The NMR spectrum was consistent with the proposed structure.

EXAMPLE 15

SYNTHESIS OF N-(4-PROPOXYPHENYLMETHYL)-4-[BIS(4-TRIFLUOROMETHOXYPHENYL) FLUOROMETHYL]PIPERIDINE (COMPOUND 105)

A stirred solution of 0.6 gram (0.001 mole) of N-(4-propoxyphenylmethyl)-4-[bis(4-trifluoromethoxyphenyl)hydroxymethyl]piperidine (prepared in Example 10) in 15 mL of methylene chloride was cooled to −78° C., and 0.15 mL (0.001 mole) of diethylaminosulphur trifluoride (DAST) was added via a syringe. Upon completion of addition, the reaction mixture was allowed to warm to ambient temperature as it stirred for about 18 hours. After this time, the reaction mixture was poured into ice-water. The mixture was then extracted with two 50 mL portions of methylene chloride. The combined extracts were dried with sodium sulfate and filtered. The filtrate was concentrated under reduced pressure to a residue, which was subjected to column chromatography on silica gel, with mixtures of 5–15% acetone in methylene chloride as the eluants. The product-containing fractions were combined and concentrated under reduced pressure, yielding about 0.1 gram of N-(4-propoxyphenylmethyl)-4-[bis(4-trifluoromethoxyphenyl)fluoromethyl]piperidine. The NMR spectrum was consistent with the proposed structure.

EXAMPLE 16

SYNTHESIS OF N-(4-PROPOXYPHENYLMETHYL)-4-[BIS(4-TRIFLUOROMETHYLPHENYL) HYDROXYMETHYL]PIPERIDINE (COMPOUND 112)

Step A

Synthesis of 4-propoxyphenylmethyl chloride as an intermediate

A mixture of 53.8 grams (0.33 mole) of 4-propoxybenzaldehyde, 200 mL of ethanol, and 200 mL of tetrahydrofuran was stirred, and 3.3 grams (0.09 mole) of sodium borohydride was added portionwise during a 30 minute period. The reaction caused the reaction mixture temperature to rise to about 45° C. Upon completion of the addition, the reaction mixture was stirred for one hour and then poured into 500 mL of water containing 50 grams of ammonium chloride. The mixture was extracted with two 500 mL portions of diethyl ether, and the combined extracts were washed with one 500 mL portion of an aqueous solution saturated with sodium chloride. The organic layer was dried with magnesium sulfate and filtered. The filtrate was concentrated under reduced pressure, yielding 53.6 grams of white solid. The solid was dissolved in 75 mL of methylene chloride and 0.75 mL of pyridine was added. The solution was added dropwise to a cold (10° C.), stirred solution of 28 mL (0.38 mole) of thionyl chloride in 350 mL of methylene chloride. The complete addition required one hour, during which time the reaction mixture was maintained at 10° C. Upon completion of the addition, the reaction mixture was stirred for one hour and poured into a solution of 350 mL of water containing 100 mL of an aqueous solution saturated with ammonium chloride. The organic layer was washed with two 250 mL portions of an aqueous solution saturated with sodium bicarbonate, and dried with magnesium chloride. The mixture was filtered and the filtrate was concentrated under reduced pressure, yielding 56.4 grams of material. The material was distilled under reduced pressure, yielding 52.5 grams of 4-propoxyphenylmethyl chloride, bp 92° C./0.3 mm Hg.

Step B

Synthesis of ethyl N-(4-propoxyphenylmethyl)piperidin-4-ylcarboxylate as an intermediate To a stirred solution of 47.5 grams (0.30 mole) of ethyl piperidin-4-ylcarboxylate in 70 mL (0.40 mole) of N,N-diisopropylethylamine was added dropwise a solution of 52.5 grams (0.29 mole) of 4-propoxyphenylmethyl chloride in 50 mL of dimethyl sulfoxide. The reaction caused the reaction mixture temperature to rise to about 35° C. Upon completion of the addition the reaction mixture was stirred for 30 minutes, warmed to 40° C., and then allowed to cool to ambient temperature. After this time the reaction mixture was poured into 500 mL of aqueous 10% ammonium chloride. The mixture was extracted with three 250 mL portions of diethyl ether, and the combined extracts were washed with two 250 mL portions of an aqueous solution saturated with ammonium chloride, one 250 mL portion of water, and one 250 mL portion of an aqueous solution saturated with sodium chloride. The organic layer was dried with magnesium sulfate and filtered. The filtrate was concentrated under reduced pressure, yielding 80.0 grams of ethyl N-(4-propoxyphenylmethyl)piperidin-4-ylcarboxylate. The NMR spectrum was consistent with the proposed structure.

Step C

Synthesis of N-(4-propoxyphenylmethyl)-4-[bis (trifluoromethylphenyl)hydroxymethyl]piperidine (Compound 112)

This compound was prepared in a manner analogous to that of Step B of Example 3, with 1.5 grams (0.005 mole) of ethyl N-(4-propoxyphenylmethyl)piperidin-4-ylcarboxylate, 3.4 grams (0.015 mole) of 4-trifluoromethylphenyl bromide, and 0.4 gram (0.015 gram-atom) of magnesium turnings in 15 mL of tetrahydrofuran as reagents. The crude product was subjected to column chromatography on silica gel, with 1:1 ethyl acetate:heptane as the eluant. The product-containing fractions were combined and concentrated under reduced pressure, yielding 1.4 grams of N-(4-propoxyphenylmethyl)-4-[bis(trifluoromethylphenyl)hydroxymethyl]piperidine. The NMR spectrum was consistent with the proposed structure.

EXAMPLE 17

SYNTHESIS OF N-[4-(CYCLOPROPYLMETHOXY) PHENYLMETHYL]-4-[BIS(4-TRIFLUOROMETHYLPHENYL) HYDROXYMETHYL]PIPERIDINE (COMPOUND 115)

Step A

Synthesis of 4-[bis(4-trifluoromethylphenyl) hydroxymethyl]piperidine as an intermediate A mixture of 10.0 grams (0.019 mole) of N-phenylmethyl-4-[bis(4-trifluoromethylphenyl)hydroxymethyl]piperidine hydrochloride (prepared as in Steps A and B of Example 12) and 3.0 grams of 5% palladium (catalyst) on charcoal in about 200 mL of 1:1 methanol:ethanol was shaken in a Parr hydrogenator for five to six hours at about 85° C., until the theoretical amount of hydrogen gas was taken up. The mixture was cooled to ambient temperature where it stood for about 18 hours. The mixture was filtered and concentrated under reduced pressure to a residue, which was stirred with ethyl acetate and an aqueous solution saturated with sodium bicarbonate until the residue dissolved. The organic layer was separated and passed through phase-separation paper to remove aqueous material. The organic layer was concentrated under reduced pressure, yielding about 7.0 grams of 4-[bis(4-trifluoromethylphenyl) hydroxymethyl]piperidine. The NMR spectrum was consistent with the proposed structure.

Step B

Synthesis of N-[4-(cyclopropylmethoxy)phenylmethyl]-4-[bis(4-trifluoromethylphenyl)hydroxymethyl]piperidine (Compound 115)

This compound was prepared in a manner analogous to that of Step D of Example 12, with 0.4 gram (0.002 mole) of 4-(cyclopropylmethoxy)phenylmethyl chloride (prepared as in Step A of Example 16), 0.9 gram (0.002 mole) of 4-[bis(4-trifluoromethylphenyl)hydroxymethyl]piperidine, and 1.1 grams (0.008 mole) of N,N-diisopropylethylamine in about 30 mL of dimethyl sulfoxide as reagents. The crude reaction product was subjected to column chromatography on silica gel with 1:1 heptane:methylene chloride, pure methylene chloride, 11:10 heptane:methylene chloride, and 1:10 acetone:methylene chloride used succesively as eluants. The product-containing fractions were combined and concentrated under reduced pressure, yielding 0.8 gram of N-[4-(cyclopropylmethoxy)phenylmethyl]-4-[bis(4-trifluoromethylphenyl)hydroxymethyl]piperidine. The NMR spectrum was consistent with the proposed structure.

EXAMPLE 18

SYNTHESIS OF N-[4-(2-ETHYLBENZOXAZOL-5-YL)METHYL]-4-[BIS(4-TRIFLUOROMETHOXYPHENYL)HYDROXYMETHYL]PIPERIDINE (COMPOUND 155)

Step A

Synthesis of ethyl 3-nitro-4-hydroxybenzoate as an intermediate

To a stirred solution of 20.0 grams (0.12 mole) of ethyl 4-hydroxybenzoate in 200 mL of acetic acid was added a solution of 7.5 mL (excess) of 70% nitric acid in 30 mL of acetic acid. After the reaction mixture stirred for about one hour, it gradually turned orange and warmed to about 40° C. The reaction mixture was stirred for an additional eighteen hours and then was poured into 800 mL of ice-water. The mixture was stirred until the ice melted, and filtered to collect a solid, which was dissolved in ethyl acetate and dried with magnesium sulfate. The mixture was filtered, and the filtrate was concentrated under reduced pressure, yielding 22.0 grams of ethyl 3-nitro-4-hydroxybenzoate, mp 70°–71° C. The NMR spectrum was consistent with the proposed structure.

Step B

Synthesis of ethyl(2-ethylbenzoxazol-5-yl)carboxylate as an intermediate

A mixture of 10.4 grams (0.05 mole) of ethyl 3-nitro-4-hydroxybenzoate, 0.3 gram of platinum oxide (catalyst) in 200 mL of ethyl acetate was shaken in a Parr hydrogenator until the theoretical amount of hydrogen gas was taken up. The mixture was filtered to remove the catalyst, and the filtrate was concentrated under reduced pressure, yielding 9.6 grams of ethyl 3-amino-4-hydroxybenzoate as a solid. The NMR spectrum was consistent with the proposed structure. This 3-amino derivative, 9.0 grams (0.05 mole), was dissolved in 150 mL of ethanol and 9.7 grams (0.06 mole) of triethyl orthopropionate was added. The reaction mixture was heated at reflux for three hours, then cooled to ambient temperature and concentrated under reduced pressure to a residue. The residue was subjected to column chromatography on silica gel, with 1:4 ethyl acetate:heptane as the eluant. The product-containing fractions were combined and concentrated under reduced pressure, yielding 8.7 grams of ethyl(2-ethylbenzoxazol-5-yl)carboxylate, mp 35°–37° C. The NMR spectrum was consistent with the proposed structure.

Step C

Synthesis of (2-ethylbenzoxazol-5-yl)methanol as an intermediate

A stirred solution of 8.0 grams (0.037 mole) of ethyl(2-ethylbenzoxazol-5-yl)carboxylate in 100 mL of anhydrous tetrahydrofuran was cooled to 0° C., and 20 mL (0.02 mole) of a 1.0 molar solution of lithium aluminum hydride in tetrahydrofuran was added portionwise from a syringe. Upon completion of the addition the reaction mixture was stirred at 0° C. for 15 minutes, then was allowed to warm to ambient temperature, where it stirred for about 18 hours. The reaction mixture was poured into a mixture of 250 mL of an aqueous solution saturated with ammonium chloride and ice. The mixture was then extracted with two 250 mL portions of diethyl ether. The combined extracts were washed with an aqueous solution saturated with sodium chloride, dried with magnesium sulfate, and filtered. The filtrate was concentrated under reduced pressure to a residue, which was subjected to column chromatography on silica gel, with ethyl acetate as the eluant. The product-containing fractions were combined and concentrated under reduced pressure, yielding 4.1 grams of (2-ethylbenzoxazol-5-yl)methanol. The NMR spectrum was consistent with the proposed structure.

Step D

Synthesis of ethyl N-(2-ethylbenzoxazol-5-ylmethyl)piperidin-4-ylcarboxylate as an intermediate To a stirred solution of 3.4 grams (0.019 mole) of (2-ethylbenzoxazol-5-yl)methanol in 25 mL of toluene was added 1.6 grams (0.006 mole) of phosphorous tribromide from a syringe. A precipitate formed immediately, and additional toluene was added to the reaction mixture to aid stirring. The reaction caused the reaction mixture temperature to rise to about 35° C. Upon completion of the addition, the reaction mixture stirred for an additional 20 minutes. The reaction mixture was then concentrated under reduced pressure to a residual solid. The solid was dissolved in 30 mL of dimethyl sulfoxide and, with stirring, 3.7 grams (0.029 mole) of N,N-diisopropylethylamine and 3.1 grams (0.019 mole) of ethyl piperidin-4-ylcarboxylate were added simultaneously from syringes. The resultant reaction caused the reaction mixture temperature to rise to about 40° C. The reaction mixture was allowed to cool to ambient temperature as it stirred for about 18 hours. The reaction mixture was poured into water and extracted with ethyl acetate and then with diethyl ether. The combined extracts were washed with an aqueous solution saturated with sodium bicarbonate, and then with an aqueous solution saturated with sodium chloride. The organic layer was concentrated under reduced pressure to a residual oil, which was subjected to column chromatography on silica gel, with ethyl acetate as the eluant. The product-containing fractions were combined and concentrated under reduced pressure, yielding 2.1 grams of ethyl N-(2-ethylbenzoxazol-5-ylmethyl)piperidin-4-ylcarboxylate. The NMR spectrum was consistent with the proposed structure.

Step E

Synthesis of N-[4-(2-ethylbenzoxazol-5-yl)methyl]-4-[bis(4-trifluoromethoxyphenyl)hydroxymethyl]piperidine (Compound 155)

This compound was prepared in a manner analogous to that of Step B of Example 3, with 1.9 grams (0.006 mole) of ethyl N-(2-ethylbenzoxazol-5-ylmethyl)piperidin-4-ylcarboxylate, 3.6 grams (0.015 mole) of 4-trifluoromethoxyphenyl bromide, and 0.4 gram (0.015 gram-atom) of magnesium turnings in 35 mL of tetrahydrofuran as reagents. The crude reaction product was subjected to column chromatography on silica gel, with methylene chloride and then ethyl acetate as eluants. The product-containing fractions were combined and concentrated under reduced pressure, yielding 2.1 grams of N-[4-(2-ethylbenzoxazol-5-yl)methyl]-4-[bis(4-trifluoromethoxyphenyl)hydroxymethyl]piperidine. The NMR spectrum was consistent with the proposed structure.

EXAMPLE 19

SYNTHESIS OF N-[4-(2-METHYL-2H-TETRAZOL-5-YL)PHENYLMETHYL]-4-[BIS(4-TRIFLUOROMETHYLPHENYL)HYDROXYMETHYL]PIPERIDINE (COMPOUND 209)

Step A

Synthesis of 4-(2-methyl-2H-tetrazol-5-yl)benzaldehyde as an intermediate

A stirred solution of 2.2 grams (0.009 mole) 4-(2-methyl-2H-tetrazol-5-yl)phenyl bromide (prepared by the method of G. D. Diana et al., J. Med. Chem. 1993, 36, 3240–3250) in 70 mL of dry tetrahydrofuran was cooled to −70° C., and 7.4 mL (0.018 mole) of n-butyllithium (2.5M in hexanes) was added dropwise from a syringe. The resulting reaction caused the reaction mixture temperature to rise to about −50° C. The reaction mixture was again cooled to −70° C., and stirring was continued for about 30 minutes. After this time 0.8 mL (0.010 mole) of N,N-dimethylformamide was added during a 90 second period. The reaction mixture was then stirred for 30 minutes at ice-water bath temperature, after which time it was allowed to warm to ambient temperature. The reaction mixture was poured into 200 mL of an aqueous solution saturated with ammonium chloride. The mixture was stirred for about 90 minutes and then extracted with three 150 mL portions of ethyl acetate. The combined extracts were washed with one 400 mL portion of an aqueous solution saturated with sodium chloride. The organic layer was dried with sodium sulfate and filtered. The filtrate was concentrated under reduced pressure to a residual oil, which was subjected to column chromatography on silica gel, with 3:7 ethyl acetate:heptane as the eluant. The product-containing fractions were combined and concentrated under reduced pressure, yielding 0.5 gram of 4-(2-methyl-2H-tetrazol-5-yl)benzaldehyde. The NMR spectrum was consistent with the proposed structure.

Step B

Synthesis of 4-(2-methyl-2H-tetrazol-5-yl)phenylmethanol as an intermediate

This compound was prepared in a manner analogous to that of Step A of Example 16, with 0.5 gram (0.003 mole) of 4-(2-methyl-2H-tetrazol-5-yl)benzaldehyde and 0.1 gram (0.003 mole) of sodium borohydride in 17 mL of ethanol. The yield of 4-(2-methyl-2H-tetrazol-5-yl)phenylmethanol was about 0.4 gram. The NMR spectrum was consistent with the proposed structure.

Step C

Synthesis of 4-(2-methyl-2H-tetrazol-5-yl)phenylmethyl bromide as an intermediate This compound was prepared in a manner analogous to that of Step D of Example 18, with 0.4 gram (0.002 mole) of 4-(2-methyl-2H-tetrazol-5-yl)phenylmethanol and 0.07 mL (0.0007 mole) of phosphorous tribromide in 7 mL of tetrahydrofuran as the reagents. The yield of 4-(2-methyl-2H-tetrazol-5-yl)phenylmethyl bromide was 0.7 gram, which was used in the next reaction without further characterization.

Step D

Synthesis of N-[4-(2-methyl-2H-tetrazol-5-yl)phenylmethyl]-4-[bis(4-trifluoromethylphenyl)hydroxymethyl]piperidine (Compound 209)

This compound was prepared in a manner analogous to that of Step D of Example 12, with 0.3 gram (0.001 mole) of 4-(2-methyl-2H-tetrazol-5-yl)phenylmethyl bromide, 0.5 gram (0.001 mole) of 4-[bis(4-trifluoromethoxyphenyl)hydroxymethyl]piperidine (prepared as in Step C of Example 12), and 0.6 gram (0.004 mole) of N,N-diisopropylethylamine in about 5 mL of dimethyl sulfoxide as reagents. The crude reaction product was subjected to column chromatography on silica gel, with 3:7 acetone:methylene chloride as the eluant. The product-containing fractions were combined and concentrated under reduced pressure, yielding about 0.2 gram of N-[4-(2-methyl-2H-tetrazol-5-yl)phenylmethyl]-4-[bis(4-trifluoromethylphenyl)hydroxymethyl]piperidine. The NMR spectrum was consistent with the proposed structure.

EXAMPLE 20

SYNTHESIS OF N-[4-(4,5-DIHYDRO-1-METHYL-5-OXO-1H-1,2,4-TRIAZOL-4-YL)PHENYLMETHYL]-4-[BIS(4-TRIFLUOROMETHYLPHENYL)HYDROXYMETHYL]PIPERIDINE (COMPOUND 212)

Step A

Synthesis of 4,5-dihydro-1-methyl-5-oxo-4-(4-methylphenyl)-1H-1,2,4-triazole as an intermediate To a stirred solution of 3.5 grams (0.08 mole) of methylhydrazine in 50 mL of tetrahydrofuran, cooled to 0° C., was added dropwise 10.0 grams (0.08 mole) of 4-methylphenyl isocyanate. Upon completion of the addition the reaction mixture was stirred at 0° C. for 30 minutes, then allowed to warm to ambient temperature, where it stirred for one hour. After this time the reaction mixture was concentrated under reduced pressure to a residual solid. The solid was dissolved in 100 mL of dioxane and 11.1 grams (0.08 mole) of triethyl orthoformate and three drops of concentrated sulfuric acid were added. The reaction mixture was heated at reflux for about three hours, during which time about 75 mL of a water-dioxane azeotrope was collected by distillation, after which the reaction mixture was stirred at ambient temperature for about 60 hours. The reaction mixture was then concentrated under reduced pressure to a residual solid. The solid was dissolved in about 150 mL of ethyl acetate, and washed with one 50 mL portion of an aqueous solution saturated with sodium bicarbonate and one 50 mL portion of an aqueous solution saturated with sodium chloride. The organic layer was dried with magnesium sulfate and filtered. The filtrate was concentrated under reduced pressure to a residual solid, which was subjected to column chromatography on silica gel, with 3:7 ethyl acetate-:heptane as the eluant. The product-containing fractions were combined and concentrated under reduced pressure, yielding 5.6 grams of an uncyclized intermediate of the intended product. This intermediate was then stirred with 10 mL of Eaton's Reagent (a 7.5% wt/wt solution of phosphorous pentoxide in methanesulfonic acid) for about 18 hours. The mixture was then poured into ice-water and the resultant precipitate collected by filtration, yielding 3.3 grams of 4,5-dihydro-1-methyl-5-oxo-4-(4-methylphenyl)-1H-1,2,4-triazole. The NMR spectrum was consistent with the proposed structure.
Step B Synthesis of
4,5-dihydro-1-methyl-5-oxo-4-(4-bromomethylphenyl)-1H-1,2,4-triazole as an intermediate To a stirred solution of 2.6 grams (0.013 mole) of 4,5-dihydro-1-methyl-5-oxo-4-(4-methylphenyl)-1H-1,2,4-triazole in 150 mL of carbon tetrachloride were added 0.3 gram (catalyst) of benzoyl peroxide and 2.5 grams (0.014 mole) of N-bromosuccinimide. The reaction mixture was heated at reflux for three hours, after which it was cooled and concentrated under reduced pressure, yielding 2.6 grams of 4,5-dihydro-1-methyl-5-oxo-4-(4-bromomethylphenyl)-1H-1,2,4-triazole, which was used in the next reaction without further characterization.
Step C Synthesis of
N-[4-(4,5-dihydro-1-methyl-5-oxo-1H-1,2,4-triazol-4-yl)phenylmethyl]-4-[bis(4-trifluoromethylphenyl) hydroxymethyl]piperidine (Compound 212)

This compound was prepared in a manner analogous to that of Step D of Example 12, with 2.0 grams (0.007 mole) of 4,5-dihydro-1-methyl-5-oxo-4-(4-bromomethylphenyl)-1H-1,2,4-triazole, 2.0 grams (0.005 mole) of 4-[bis(4-trifluoromethoxyphenyl)hydroxymethyl]piperidine (prepared as in Step C of Example 12), and 3.2 grams (0.025 mole) of N,N-diisopropylethylamine in about 15 mL of dimethyl sulfoxide as reagents. The crude reaction product was subjected to column chromatography on silica gel, with 2:8 heptane:ethyl acetate, and then pure ethyl acetate as eluants. The product-containing fractions were combined and concentrated under reduced pressure, yielding 1.6 grams of N-[4-(4,5-dihydro-1-methyl-5-oxo-1H-1,2,4-triazol-4-yl)phenylmethyl]-4-[bis(4-trifluoromethylphenyl)hydroxymethyl]piperidine. The NMR spectrum was consistent with the proposed structure.

EXAMPLE 21

SYNTHESIS OF
N-(THIEN-2-YLMETHYL)-4-[BIS(4-TRIFLUOROMETHOXYPHENYL) HYDROXYMETHYL]PIPERIDINE (COMPOUND 228)

Step A

Synthesis of ethyl
N-(thien-2-ylmethyl)piperidin-4-ylcarboxylate as an intermediate This compound was prepared in a manner analogous to that of Step B of Example 16, with 2.0 grams (0.015 mole) of thien-2-ylmethyl chloride, 2.6 mL (0.017 mole) of ethyl piperidin-4-ylcarboxylate, and 10.5 mL (0.060 mole) of N,N-diisopropylethylamine in about 15 mL of dimethyl sulfoxide as reagents. The yield of ethyl N-(thien-2-ylmethyl)piperidin-4-ylcarboxylate was about 3.4 grams. The NMR spectrum was consistent with the proposed structure.
Step B Synthesis of N-(thien-2-ylmethyl)-4-[bis(4-trifluoromethoxyphenyl)hydroxymethyl]piperidine (Compound 228)

This compound was prepared in a manner analogous to that of Step B of Example 3, with 2.0 grams (0.008 mole) of ethyl N-(thien-2-ylmethyl)piperidin-4-ylcarboxylate, 3.5 mL (0.024 mole) of 4-trifluoromethoxyphenyl bromide, and 0.6 gram (0.025 gram-atom) of magnesium turnings in about 69 mL of tetrahydrofuran as reagents. The crude reaction product was subjected to column chromatography on silica gel, with pure methylene chloride, 9:1 methylene chloride-:acetone, pure acetone, and then 8:2 methylene chloride:acetone as eluants. The product-containing fractions were combined and concentrated under reduced pressure, yielding about 0.2 gram of N-(thien-2-ylmethyl)-4-[bis(4-trifluoromethoxyphenyl)hydroxymethyl]piperidine. The NMR spectrum was consistent with the proposed structure.

EXAMPLE 22

SYNTHESIS OF
N-(4-FLUOROINDOL-3-YLMETHYL)-4-[BIS(4-TRIFLUOROMETHOXYPHENYL) HYDROXYMETHYL]PIPERIDINE (COMPOUND 231)

Step A

Synthesis of ethyl
N-(4-fluoroindol-3-ylmethyl)piperidin-4-ylcarboxylate as an intermediate A stirred solution of 1.8 grams (0.011 mole) of ethyl piperidin-4-ylcarboxylate in 10 mL of dioxane was cooled to 0° C., and 10 mL of acetic acid, followed by 0.9 mL of aqueous 37% formaldehyde were added. To this was then slowly added a solution of 1.5 grams (0.011 mole) of 4-fluoroindole in 10 mL of dioxane. Upon completion of the addition, the reaction mixture was allowed to warm to ambient temperature where it stirred for about five hours. After this time the reaction mixture was again cooled to 0° C., and neutralized with an aqueous solution saturated with sodium bicarbonate. The mixture was extracted with two 100 mL portions of diethyl ether. The combined extracts were washed with an aqueous solution saturated with sodium chloride, dried with sodium sulfate, and filtered. The filtrate was then passed through a pad of silica gel. The eluate was concentrated under reduced pressure, yielding 1.2 grams of ethyl N-(4-fluoroindol-3-ylmethyl)piperidin-4-yl-carboxylate, mp 96°–105° C. The NMR spectrum was consistent with the proposed structure.

Step B

Synthesis of N-(4-fluoroindol-3-ylmethyl)-4-[bis(4-trifluoromethoxyphenyl)hydroxymethyl]piperidine (Compound 231)

This compound was prepared in a manner analogous to that of Step B of Example 3, with 0.5 gram (0.0016 mole) of ethyl N-(4-fluoroindol-3-ylmethyl)piperidin-4-ylcarboxylate, 2.0 grams (0.0082 mole) of 4-trifluoromethoxyphenyl bromide, and 0.2 gram (0.0086 gram-atom) of magnesium turnings in about 10 mL of diethyl ether as reagents. The crude reaction product was taken up in hexane. The hexane-insoluble material was collected by filtration and purified by preparative thin layer chromatography with 1:3 ethyl acetate:hexane as an eluant, yielding about 0.09 gram of N-(4-fluoroindol-3-ylmethyl)-4-[bis(4-trifluoromethoxyphenyl)hydroxymethyl]piperidine, mp 76°–88° C. The NMR spectrum was consistent with the proposed structure.

EXAMPLE 23

SYNTHESIS OF N-[4-(METHOXYCARBONYLAMINO) PHENYLMETHYL]-4-[BIS(4-TRIFLUOROMETHOXYPHENYL) HYDROXYMETHYL]PIPERIDINE (COMPOUND 192)

Step A

Synthesis of N-(4-aminophenylmethyl)-4-[bis(4-trifluoromethoxyphenyl)hydroxymethyl]piperidine (Compound 181) as an intermediate A mixture of 2.5 grams (0.004 mole) of N-(4-nitrophenylmethyl)-4-[bis(4-trifluoromethoxyphenyl)hydroxymethyl]piperidine (Compound 179-prepared as described in Example 17) and 0.25 gram of platinum oxide catalyst in 40 mL of ethanol was shaken in a Parr hydrogenator until the theoretical amount of hydrogen gas was taken up. After this time the mixture was removed from the Parr hydrogenator and stirred with diatomaceous earth and methylene chloride. The mixture was filtered through a fiberglass filter paper. The filtrate was concentrated under reduced pressure, yielding 2.5 grams of N-(4-aminophenylmethyl)-4-[bis(4-trifluoromethoxyphenyl)hydroxymethyl]piperidine. The NMR spectrum was consistent with the proposed structure.

Step B

Synthesis of N-[4-(methoxycarbonylamino)phenylmethyl]-4-[bis(4-trifluoromethoxyphenyl) hydroxymethyl]piperidine (Compound 192)

A stirred solution of 0.8 gram (0.0014 mole) of N-(4-aminophenylmethyl)-4-[bis(4-trifluoromethoxyphenyl)hydroxymethyl]piperidine in 15 mL of tetrahydrofuran was cooled to 0° C., and 0.11 mL of methyl chloroformate was added dropwise from a syringe. Upon completion of the addition, 0.12 mL of pyridine was added in one portion. The reaction mixture was allowed to warm to ambient temperature where it stirred for about 18 hours. After this time the reaction mixture was poured into a mixture of ethyl acetate and an aqueous solution saturated with sodium chloride. After a period of stirring, the organic layer was separated and dried with sodium sulfate. The mixture was filtered, and the filtrate was concentrated under reduced pressure to a residual solid. The solid was subjected to column chromatography on silica gel, with pure methylene chloride, and 1:9, 1:4, 1:3, and 3:7 mixtures of acetone:methylene chloride as eluants. The product-containing fractions were combined and concentrated under reduced pressure, yielding 0.45 gram of N-[4-(methoxycarbonylamino)phenylmethyl]-4-[bis(4-trifluoromethoxyphenyl)hydroxymethyl]piperidine. The NMR spectrum was consistent with the proposed structure.

EXAMPLE 24

SYNTHESIS OF N-[4-(METHOXYCARBONYLAMINO) PHENYLMETHYL]-4-[BIS(4-TRIFLUOROMETHOXYPHENYL) HYDROXYMETHYL]PIPERIDINE, N-OXIDE (COMPOUND 322)

This compound was prepared in a manner analogous to that of Example 9, with 0.36 gram (0.0006 mole) of N-[4-(methoxycarbonylamino)phenylmethyl]-4-[bis(4-trifluoromethoxyphenyl)hydroxymethyl]piperidine (prepared in Example 23) and 0.22 gram (0.0006 mole) of 50–60% 3-chloroperoxybenzoic acid in 5 mL of chloroform as reagents. The crude reaction product was purified by preparative thin layer chromatography using 15% methanol in chloroform, yielding 0.29 gram of N-[4-(methoxycarbonylamino)phenylmethyl]-4-[bis(4-trifluoromethoxyphenyl)hydroxymethyl]piperidine, N-oxide, mp 178°–182° C. The NMR spectrum was consistent with the proposed structure.

EXAMPLE 25

SYNTHESIS OF N-[4-(DIETHYLPHOSPHONO) PHENYLMETHYL]-4-[BIS(4-TRIFLUOROMETHYLPHENYL) HYDROXYMETHYL]PIPERIDINE (COMPOUND 333)

Step A

Synthesis of 4-(diethylphosphono)phenylmethyl acetate as an intermediate

A mixture of 9.7 mL (0.057 mole) of triethylamine and 2.4 grams (0.002 mole) of tetrakis(triphenylphosphine) palladium(0) was stirred, and 7.3 mL (0.057 mole) of diethyl phosphite was added. To this was added 13.2 grams (0.057 mole) of 4-bromophenylmethyl acetate. The reaction mixture was warmed to about 100° C., where it stirred for 30 minutes. The reaction mixture was cooled, and 200 mL of ethyl acetate was added. The resultant solid was collected by filtration, and washed with 50 mL of ethyl acetate. The combined wash and filtrate were concentrated under reduced pressure to a residual oil, which was subjected to column chromatography on silica gel, with 3:7 heptane:ethyl acetate as eluant. The product-containing fractions were combined and concentrated under reduced pressure, yielding 11.1 grams of 4-(diethylphosphono)phenylmethyl acetate. The NMR spectrum was consistent with the proposed structure.

Step B

Synthesis of 4-(diethylphosphono)phenylmethanol as an intermediate

To a stirred solution of 3.0 grams (0.01 mole) of 4-(diethylphosphono)phenylmethyl acetate in 10 mL of tetrahydrofuran was added a solution of 0.4 gram (0.01 mole) of sodium hydroxide in 1 mL of water. Upon completion of the addition, the reaction mixture was stirred at ambient temperature for one hour. After this time 5 mL of ethanol was added, and the reaction mixture was warmed to reflux, where it stirred for one hour. The reaction mixture was poured into a stirred mixture of water and ethyl acetate. The organic layer was separated and dried with magnesium sulfate. The mixture was filtered and the filtrate was concentrated under reduced pressure, yielding 2.1 grams of 4-(diethylphosphono)phenylmethanol. The NMR spectrum was consistent with the proposed structure.

Step C

Synthesis of N-[4-(diethylphosphono)phenylmethyl]-4-[bis(4-trifluoromethylphenyl)hydroxymethyl]piperidine (Compound 333)

To a stirred solution of 1.3 grams (0.004 mole) of 4-(diethylphosphono)phenylmethanol and two drops of pyridine in 10 mL of methylene chloride was added 0.39 mL (0.005 mole) of thionyl chloride. Upon completion of the addition, the reaction mixture was stirred for 30 minutes, then washed with 10 mL of water and 10 mL of an aqueous solution saturated with sodium chloride. The organic layer was dried with magnesium sulfate and filtered. The filtrate was concentrated under reduced pressure, yielding the intermediate 4-(diethylphosphono)phenylmethyl chloride. The chloride was not further characterized. A solution of 2.7 grams (0.005 mole) of 4-[bis(4-trifluoromethylphenyl)hydroxymethyl]piperidine (prepared as in Step A of Example 17) in 10 mL of dimethyl sulfoxide was stirred, and 2.5 mL (excess) of diisopropylethylamine was added. To this was then added a solution of the methyl chloride, prepared above, in one mL of dimethyl sulfoxide. Upon completion of the addition, the reaction mixture was stirred at ambient temperature for one hour, then poured into water, and the mixture was extracted with one 150 mL portion of methylene chloride. The extract was washed with one 50 mL portion of an aqueous solution saturated with ammonium chloride and one 50 mL portion of water. The extract was concentrated under reduced pressure to a residue, which was subjected to column chromatography on silica gel, with pure ethyl acetate as the eluant. The product-containing fractions were combined and concentrated under reduced pressure, yielding 1.6 grams of N-[4-(diethylphosphono)phenylmethyl]-4-[bis(4-trifluoromethylphenyl)hydroxymethyl]piperidine. The NMR spectrum was consistent with the proposed structure.

EXAMPLE 26

AN ALTERNATE SYNTHESIS OF 4-[BIS(4-TRIFLUOROMETHOXYPHENYL)HYDROXYMETHYL]PIPERIDINE FOR USE AS AN INTERMEDIATE

Step A

Synthesis of ethyl N-(trimethylsilyl)piperidin-4-ylcarboxylate as an intermediate Under a nitrogen atmosphere, a stirred solution of 100.0 grams (0.64 mole) of ethyl piperidin-4-ylcarboxylate and 94 mL (0.67 mole) of triethylamine in 1400 mL of diethyl ether was cooled to 15° C., and a solution of 86 mL (0.68 mole) of chlorotrimethylsilane in 100 mL of diethyl ether was added dropwise during a 30 minute period. Upon completion of the addition, the thick reaction mixture was stirred vigorously for one hour while warming to ambient temperature. The reaction mixture was then filtered, and the collected solid was washed with diethyl ether. The combined wash and filtrate were concentrated under reduced pressure to a residual oil. The oil was distilled under reduced pressure, yielding 115.0 grams (79% yield) of ethyl N-(trimethylsilyl)piperidin-4-ylcarboxylate, bp 75° C./0.1 mm Hg. The NMR spectrum was consistent with the proposed structure.

Step B

Synthesis of 4-[bis(trifluoromethoxyphenyl)hydroxymethyl]piperidine as an intermediate A stirred mixture of 5.0 grams (0.021 mole) of 4-trifluoromethoxyphenyl bromide, 13.8 grams (0.570 gram-atom) of magnesium turnings, and a crystal of iodine in 25 mL of anhydrous tetrahydrofuran was warmed to 50°–60° C. Once the Grignard reaction commenced, 500 ml of anhydrous tetrahydrofuran was added, and the reaction mixture temperature was adjusted to 45° C. To this was added a solution of 53.0 grams (0.230 mole) of ethyl N-(trimethylsilyl)piperidin-4-ylcarboxylate and 128.8 grams (0.534 mole) of 4-trifluoromethoxyphenyl bromide in 475 mL of anhydrous tetrahydrofuran at a rate to maintain the reaction mixture temperature at 45°–55° C. Upon completion of the addition, the reaction mixture heated at reflux for about two hours, after which the reaction mixture was poured into a stirred mixture of 550 mL of an aqueous solution saturated with ammonium chloride and 200 grams of ice. The mixture was then extracted with 650 mL of ethyl acetate. The organic layer was shaken with one 250 mL portion of an aqueous solution saturated with sodium bicarbonate, one 250 mL portion of aqueous 10% sodium hydroxide solution, and with two 200 mL portions of an aqueous solution saturated with sodium chloride. The organic layer was dried with sodium sulfate and filtered. The filtrate was concentrated under reduced pressure, yielding 110 grams of residual oil. The oil was triturated with 500 mL of petroleum ether, and 67.0 grams of solid 4-[bis(trifluoromethoxyphenyl)hydroxymethyl]piperidine was collected by filtration. The filtrate was cooled, and an additional 15.5 grams of solid 4-[bis(trifluoromethoxyphenyl)hydroxymethyl]piperidine was collected by filtration. The total yield was 82%. The NMR spectrum was consistent with the proposed structure.

Representative compounds prepared by the methods exemplified above are listed in Table 1. Characterizing properties are given in Table 2.

Biological Data

Candidate insecticides were incorporated into an artificial diet for evaluation of insecticidal activity against the tobacco budworm (*Heliothis virescens* [Fabricius]) in the following manner. Stock solutions of test chemical in dimethyl sulfoxide, ranging from 50 micromolar to 0.005 micromolar, were prepared for each rate of application. One hundred microliters of each of the stock solutions was manually stirred into 50 mL of a molten (65°–70° C.) wheat germ-based artificial diet. The 50 mL of molten diet containing the test chemical was poured evenly into twenty wells in the outer two rows on each side of a twenty-five well, five row plastic tray. (Each well in the tray was about 1 cm in depth, with an opening of 3 cm by 4 cm at the lip.) Molten diet containing only dimethyl sulfoxide at the levels used in the test chemical-treated diet was poured into the five wells in the third (center) row of the tray. Each tray therefore contained one test chemical at a single rate of application, together with an untreated control. The rates of application, expressed as the negative log of the molar concentration, and the corresponding concentrations of the stock solution prepared for each rate are shown below:

| Stock Solution | Rate of Application |
| --- | --- |
| 50 micromolar | 4 |
| 5 | 5 |
| 0.5 | 6 |
| 0.05 | 7 |
| 0.005 | 8 |

Single second instar tobacco budworm larvae, selected at a stage of growth at which they uniformly weigh about 5 mg each, were placed in each well. Upon completion of infestation, a sheet of clear plastic was heat-sealed over the top of the tray by use of a common household flat iron. The trays were held at 25° C. at 60% relative humidity for five days in a growth chamber. Lighting was set at 14 hours of light and 10 hours of darkness. After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Also, where possible, the negative log of the concentration of the test chemical that provided 50% mortality ($pLC_{50}$) was determined.

Candidate insecticides with high $pI_{50}$ values from the diet test were tested for insecticidal activity in foliar evaluations against tobacco budworm, beet armyworm (*Spodoptera exigua* [Hubner]), and cabbage looper (*Trichoplusia ni* [Hubner]).

In these tests against tobacco budworm and beet armyworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing one chick pea plant, for each rate of application of test chemical were sprayed. The treated plants were transferred to a hood, where they were kept until the spray had dried.

The four chick pea plants for each replicate treated with test chemical as described above were removed from their pots by cutting the stems just above the soil line. The excised leaves and stems from the four plants in each replicate were placed in individual 8-ounce paper cups, each containing a moistened filter paper. Five second-instar (6 days old) tobacco budworms or beet armyworms (7–8 days old) were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead, moribund, and live insects were counted. Using the insect counts, the efficacy of the test chemical was expressed in percent control. Percent control is derived from the total number of dead insects (TD) plus the total number of moribund insects (TM) as compared to the total number of insects (TI) in the test:

$$\% \text{ Control} = \frac{TD + TM}{TI} \times 100$$

The condition of the test plants was also observed for phytotoxicity and for reduction of feeding damage as compared to an untreated control.

Foliar tests with cabbage looper were conducted in the same manner as described above, the difference being that pinto bean plants (*Phaseolus vulgaris*) were used in place of chick pea plants.

The compounds of the present invention were active in the diet test against the tobacco budworm. Compounds 22, 24, 27, 28, 29, 34, 39, 42, 43, 46, 47, 48, 52, 55, 57, 65, 68, 78, 79, 80, 88, 89, 90, 92, 94, 96, 97, 98, and 102 all exhibited $pI_{50}$ values of 6.0 or greater. Table 3 gives the insecticidal activity data for compounds tested in the diet test.

The compounds of the present invention also showed good to excellent insecticidal activity in the foliar test against tobacco budworm, beet armyworm, and cabbage looper. It can be seen from Table 4 that many compounds provided 80% control or greater of one or more of the test insect species at an application rate of 100 ppm in the foliar test.

For insecticidal application, the active compounds are formulated into insecticidal compositions by admixture in insecticidally effective amount with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present insecticidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These insecticidal compositions may be applied either as water-diluted sprays, or dusts, or granules to the areas in which insect control is desired. These formulations may contain as little as 0.1%, 0.2% or 0.5% to as much as 95% or more by weight of active ingredient.

Dusts are free flowing admixtures of the active ingredients with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders are in the form of finely divided particles which disperse readily in water or other dispersant. The wettable powder is ultimately applied to the locus where insect control is desired either as a dry dust or as an emulsion in water or other liquid. Typical carriers for wettable powders include Fuller's earth, kaolin clays, silicas, and other highly absorbent, readily wet, inorganic diluents. Wettable powders normally are prepared to contain about 5–80% of active ingredient, depending on the absorbency of the carrier, and usually also contain a small amount of a wetting, dispersing, or emulsifying agent to facilitate dispersion. For example, a useful wettable powder formulation contains 80.8 parts of the insecticidal compound, 17.9 parts of Palmetto clay, and 1.0 part of sodium lignosulfonate and 0.3 part of sulfonated aliphatic polyester as wetting agents.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvent. For insecticidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agents, when used, normally comprise from 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for insecticidal application of TABLE 1-continued

| | | | |
|---|---|---|---|
| 2 | n-OC$_3$H$_7$ | n-C$_6$H$_{13}$ | 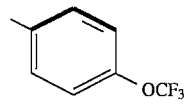 |
| 3 | n-OC$_3$H$_7$ | cyclopropyl | 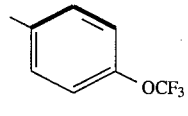 |
| 4 | n-OC$_3$H$_7$ | —CH=CH$_2$ | 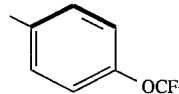 |
| 5 | n-OC$_3$H$_7$ | phenyl | 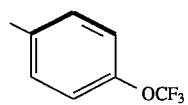 |
| 6 | —OCHF$_2$ | 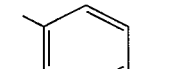 | 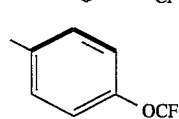 |
| 7 | n-OC$_3$H$_7$ | 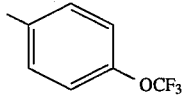 | 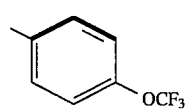 |
| 8 | n-OC$_3$H$_7$ | —CH$_2$—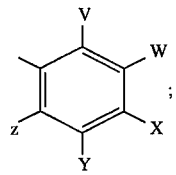 | 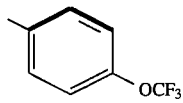 |

Where n is 1, and R$^1$ and R$^2$ are

| Cmpd. No. | R |
|---|---|
| 9 | H |
| 10 | cyclopropyl |
| 11 | cyclohexyl |
| 12 | pyridin-4-yl |

Where R is and R$^1$ and R$^2$ are

| Cmpd. No. | n | V | W | X | Y | Z |
|---|---|---|---|---|---|---|
| 13 | 1 | H | H | H | H | H |
| 14 | 1 | Cl | H | H | H | H |
| 15 | 1 | H | H | Cl | H | H |
| 16 | 1 | H | H | F | H | H |
| 17 | 1 | H | H | —CH$_3$ | H | H |
| 18 | 1 | H | H | —CH(CH$_3$)$_2$ | H | H |
| 19 | 1 | H | H | —C(CH$_3$)$_3$ | H | H |
| 20 | 1 | H | —CF$_3$ | H | H | H |
| 21 | 1 | H | H | OH | H | H |
| 22 | 1 | —OCH$_3$ | H | H | H | H |
| 23 | 1 | H | —OCH$_3$ | H | H | H |
| 24 | 1 | H | H | —OCH$_3$ | H | H |
| 25 | 2 | H | H | —OCH$_3$ | H | H |
| 26 | 3 | H | H | —OCH$_3$ | H | H |

TABLE 1-continued

| Cmpd. No. | n | | | | | |
|---|---|---|---|---|---|---|
| 27 | 1 | H | —OC$_2$H$_5$ | H | H | H |
| 28 | 1 | H | H | —OC$_2$H$_5$ | H | H |
| 29 | 1 | H | H | n-OC$_3$H$_7$ | H | H |
| 30 | 1 | H | H | —OCH(CH$_3$)$_2$ | H | H |
| 31 | 1 | H | H | —OCH$_2$CH$_2$CH(CH$_3$)$_2$ | H | H |
| 32 | 1 | H | H | —OCHF$_2$ | H | H |
| 33 | 1 | H | H | —OCF$_3$ | H | H |
| 34 | 1 | H | —CH$_3$ | —OCH$_3$ | H | H |
| 35 | 1 | —OCH$_3$ | —OCH$_3$ | H | H | H |
| 36 | 1 | —OCH$_3$ | H | —OCH$_3$ | H | H |
| 37 | 1 | —OCH$_3$ | H | H | —OCH$_3$ | H |
| 38 | 1 | —OCH$_3$ | H | H | H | —OCH$_3$ |
| 39 | 1 | H | —OCH$_3$ | —OCH$_3$ | H | H |
| 40 | 1 | —OCH$_3$ | H | —OCH$_3$ | H | —OCH$_3$ |
| 41 | 1 | H | —OCH$_3$ | —OCH$_3$ | —OCH$_3$ | H |
| 42 | 1 | H | H | —OCH$_2$CH=CH$_2$ | H | H |
| 43 | 1 | H | H | —OCH$_2$CH=CH$_2$ an N-oxide | H | H |
| 44 | 1 | H | Cl | —OCH$_3$ | H | H |
| 45 | 1 | Cl | H | —OC$_2$H$_5$ | H | H |
| 46 | 1 | H | F | —OCH$_3$ | H | H |
| 47 | 1 | H | F | —OC$_2$H$_5$ | H | H |
| 48 | 1 | H | F | n-OC$_3$H$_7$ | H | H |
| 49 | 1 | H | H | —OSi(CH$_3$)$_2$C(CH$_3$)$_3$ | H | H |
| 50 | 1 | H | H | —SCH$_3$ | H | H |
| 51 | 1 | H | H | —SC$_2$F$_5$ | H | H |
| 52 | 1 | H | H | —CH$_2$OC$_2$H$_5$ | H | H |
| 53 | 1 | H | H | —CN | H | H |
| 54 | 1 | H | H | —NO$_2$ | H | H |
| 55 | 1 | H | H | —N(CH$_3$)$_2$ | H | H |
| 56 | 1 | H | H | —C(=O)C$_2$H$_5$ | H | H |
| 57 | 1 | H | H | —CO$_2$C$_2$H$_5$ | H | H |
| 58 | 1 | H | H | phenyl | H | H |
| 59 | 1 | H | phenoxy | H | H | H |
| 60 | 1 | H | H | phenoxy | H | H |
| 61 | 1 | H | H | phenoxymethyl | H | H |
| 62 | 1 | H | phenyl-methoxy | H | H | H |
| 63 | 1 | H | H | phenylmethoxy | H | H |
| 64 | 1 | H | H | —OCH$_2$-C$_6$H$_4$-F | H | H |
| 65 | 1 | H | H | —OCH$_2$C≡CH | H | H |
| 66 | 1 | H | H | —NH(C=O)CH$_3$ | H | H |
| 67 | 1 | H | —OCH$_2$CH$_2$O— | | H | H |
| 68 | 1 | H | —CH$_2$C(CH$_3$)$_2$O— | | H | H |
| 69 | 1 | H | —OC(CH$_3$)$_2$O— | | H | H |

Where n is 1, and R is

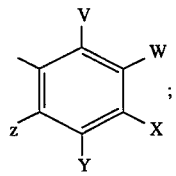

and V, W, Y, and Z are hydrogen

| Cmpd. No. | X | R$^1$ | R$^2$ |
|---|---|---|---|
| 70 | n-OC$_3$H$_7$ | 4-Cl-C$_6$H$_4$- | 4-Cl-C$_6$H$_4$- |
| 71 | n-OC$_3$H$_7$ | 3-OCF$_3$-C$_6$H$_4$- | 3-OCF$_3$-C$_6$H$_4$- |

TABLE 1-continued

| 72 | n-OC₃H₇ | 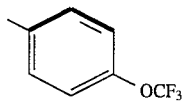 | (p-OCF₃ phenyl) |

Where n is 1, and R¹ and R² are (p-OCF₃ phenyl)

| Cmpd. No. | R |
|---|---|
| 73 | —CH₂—C(Cl)=C(Cl)₂ |
| 74 | (3-methylthiophene) |
| 75 | (5-methyl-2-propoxypyridine) |
| 76 | (2-methylpyrimidine) |
| 77 | (6-methoxy-tetrahydronaphthalene) |

Where R is  and R¹ and R² are 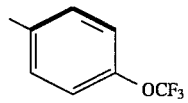

| Cmpd. No. | n | V | W | X | Y | Z |
|---|---|---|---|---|---|---|
| 78 | 1 | H | H | n-OC₄H₉ | H | H |
| 79 | 1 | H | H | —OCH₂CH(CH₃)₂ | H | H |
| 80 | 1 | H | H | —OCH₂—(cyclopropyl) | H | H |
| 81 | 1 | H | H | n-OC₅H₁₁ | H | H |
| 82 | 1 | Cl | H | n-OC₃H₇ | H | H |
| 83 | 1 | —C₂H₅ | H | n-OC₃H₇ | H | H |
| 84 | 1 | —CF₃ | H | n-OC₃H₇ | H | H |
| 85 | 1 | H | —CH₃ | n-OC₃H₇ | H | H |
| 86 | 1 | H | —C₂H₅ | n-OC₃H₇ | H | H |
| 87 | 1 | H | H | —O(CH₂)₃N(CH₃)₂ | H | |
| 88 | 1 | H | H | —OCH₂C(Cl)=CH₂ | H | |
| 89 | 1 | H | H | —OCH₂CH=CHCl cis Isomer | H | H |
| 90 | 1 | H | H | —OCH₂CH=CHCl trans Isomer | H | H |
| 91 | 1 | H | H | —OCH₂CH=CCl₂ | H | H |
| 92 | 1 | H | H | —OCH₂C(CH₃)=CH₂ | H | H |
| 93 | 1 | H | H | —OCH₂CH=C(CH₃)₂ | H | H |
| 94 | 1 | H | H | —OCH₂CH=C(CH₃)₂ an N-oxide | H | H |
| 95 | 1 | H | H | —O(CH₂)₃CH=CH₂ | H | H |
| 96 | 1 | H | H | —OCH₂C≡N | H | H |

TABLE 1-continued

| | | | | | | |
|---|---|---|---|---|---|---|
| 97 | 1 | H | H | —OCH$_2$C≡CH | H | H |
| | | | | an N-oxide | | |
| 98 | 1 | H | H | —OCH$_2$C≡CCH$_3$ | H | H |
| 99 | 1 | H | H | —SO$_2$C$_2$F$_5$ | H | H |
| 100 | 1 | H | H | —NH$_2$ | H | H |
| 101 | 1 | H | H | —NHC$_3$H$_7$ | H | H |
| 102 | 1 | H | H | —NH(C=O)C$_2$H$_5$ | H | H |

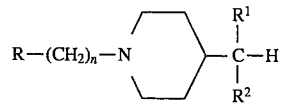

Where n is 1, and R is

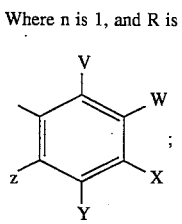

and V, W, Y, and Z are hydrogen

| Cmpd. No. | X | R$^1$ | R$^2$ |
|---|---|---|---|
| 103 | —OCH$_3$ | 4-C$_2$H$_5$-C$_6$H$_4$— | 4-C$_2$H$_5$-C$_6$H$_4$— |
| 104 | n-OC$_3$H$_7$ | 4-OCF$_3$-C$_6$H$_4$— | 4-OCF$_3$-C$_6$H$_4$— |

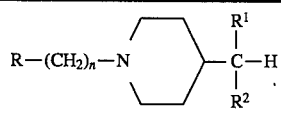

Where n is 1, and R is

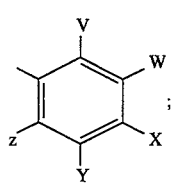

and V, W, Y, and Z are hydrogen

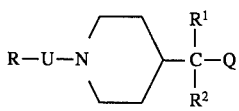

Where U is —(CH$_2$)$_n$—, and n is 1;

Q is —OH;

R is

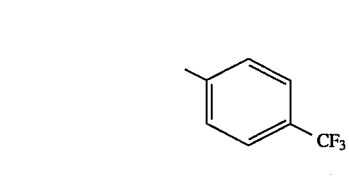

and R$^1$ and R$^2$ are 4-CF$_3$-C$_6$H$_4$—

TABLE 1-continued where V, W, Y, and Z are hydrogen

| Cmpd. No. | X | Cmpd. No. | X |
|---|---|---|---|
| 106 | H | 107 | Cl |
| 108 | F | 109 | —CH(CH$_3$)$_2$ |
| 110 | —CH$_2$CH=CH$_2$ | 111 | —OCH$_3$ |
| 112 | —OC$_3$H$_7$ | 113 | —OCH(CH$_3$)$_2$ |
| 114 | —OCH(CH$_3$)C$_2$H$_5$ | 115 | 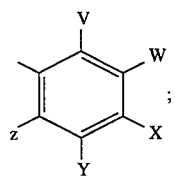 |
| 116 | —OCH$_2$C≡CH | 117 | —OCHF$_2$ |
| 118 | —OCF$_3$ | 119 | —NO$_2$ |
| 120 | —CO$_2$CH$_3$ | 121 | —CO$_2$CH(CH$_3$)$_2$ |
| 122 | —NHCO$_2$CH$_3$ | 123 | —NHCO$_2$CH(CH$_3$)$_2$ |
| 124 | 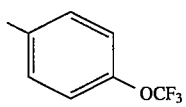 | | |

Where U is —(CH$_2$)$_n$—, and n is 1;

Q is —OH;

R is

![structure]

where Y and Z are hydrogen

R$^1$ and R$^2$ are

![structure with OCF$_3$]

| Cmpd. No. | V | W | X |
|---|---|---|---|
| 125 | H | H | —CH$_2$OH |
| 126 | H | H | —C$_4$H$_9$ |
| 127 | H | H | —C$_5$H$_{11}$ |
| 128 | H | H | —CH=CH$_2$ |
| 129 | H | H | —CH$_2$CH=CH$_2$ |
| 130 | H | H | —OCH(CH$_3$)$_2$ |
| 131 | H | H | —OC$_4$H$_9$ |
| 132 | H | H | —OCH(CH$_3$)C$_2$H$_5$ |
| 133 | H | H | —OC(CH$_3$)$_3$ |
| 134 | H | H | —OCH(C$_2$H$_5$)$_2$ |
| 135 | H | H | —OCH(C$_3$H$_7$)$_2$ |
| 136 | H | H | (O-cyclohexyl) |
| 137 | H | H | —OCH$_2$OCH$_3$ |
| 138 | H | H | —OCH$_2$OC$_2$H$_4$OCH$_3$ |
| 139 | H | H | —OC$_2$H$_4$Cl |
| 140 | H | H | —OCH$_2$CH=CHCH$_3$ |
| 141 | H | H | (OCH$_2$-methylcyclopropyl) |
| 142 | H | H | (OCH$_2$-methylcyclopropyl) |

TABLE 1-continued
| | | | |
|---|---|---|---|
| 143 | H | H | 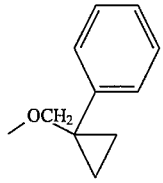 |
| 144 | H | H |  |
| 145 | H | H | 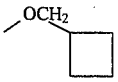 |
| 146 | H | H | 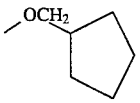 |
| 147 | H | H | 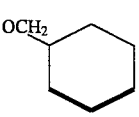 |
| 148 | H | H | —OCH(CH$_3$)C≡N |
| 149 | H | H | —SO$_2$CH$_3$ |
| 150 | H | H | —OSO$_2$C$_2$H$_5$ |
| 151 | H | H | 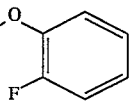 |
| 152 | H | H | 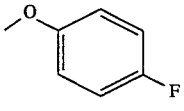 |
| 153 | H | —CH=CHCH=CH— | |
| 154 | H | —CH$_2$CH$_2$O— | |
| 155 | H | —N=C(C$_2$H$_5$)O— | |
| 156 | H | H | —(C=O)H |
| 157 | H | H | —CO$_2$H |
| 158 | H | H | —CO$_2$CH$_3$ |
| 159 | H | H | —CO$_2$CH(CH$_3$)$_2$ |
| 160 | H | H | —CO$_2$C$_4$H$_9$ |
| 161 | H | H | 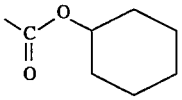 |
| 162 | H | H | —CO$_2$CH$_2$CF$_3$ |
| 163 | H | H | —CO$_2$CH$_2$OCH$_3$ |
| 164 | H | H | —(C=O)SC$_2$H$_5$ |
| 165 | H | H | 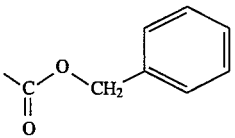 |
| 166 | H | H | —(C=O)NHC$_2$H$_5$ |
| 167 | H | H | —(C=O)N(CH$_3$)$_2$ |
| 168 | H | H | —(C=O)NHOCH$_3$ |
| 169 | H | H | —(C=O)N(CH$_3$)(OCH$_3$) |
| 170 | H | H | —(C=O)NHCH$_2$C≡CH |
| 171 | H | H | —(C=O)NHN(CH$_3$)$_2$ |
| 172 | H | H | —O(C=O)C$_2$H$_5$ |

TABLE 1-continued

| | | | |
|---|---|---|---|
| 173 | H | H | —OCH$_2$(C═O)CH$_3$ |
| 174 | H | H | —OCH(C$_2$H$_5$)(C═O)OC$_2$H$_5$ |
| 175 | H | H | —O(C═O)NHCH$_3$ |
| 176 | H | H | —O(C═O)NHC$_2$H$_5$ |
| 177 | H | H | —O(C═O)N(CH$_3$)$_2$ |
| 178 | H | —NO$_2$ | H |
| 179 | H | H | —NO$_2$ |
| 180 | H | —NH$_2$ | H |
| 181 | H | H | —NH$_2$ |
| 182 | H | H | —NHCH$_3$ |
| 183 | H | H | —NHC$_4$H$_9$ |
| 184 | H | H | —NHCH$_2$C≡CH |
| 185 | H | H | —NHSO$_2$CH$_3$ |
| 186 | H | H | —NHSO$_2$C$_2$H$_5$ |
| 187 | H | H | ![structure: CH$_2$-phenyl with NH] |
| 188 | H | H | —N(CH$_3$)(C$_3$H$_7$) |
| 189 | H | H | —NH(C═O)H |
| 190 | H | H | —NH(C═O)C$_3$H$_7$ |
| 191 | H | H | ![structure: NH-C(═O)-phenyl] |
| 192 | H | H | —NHCO$_2$CH$_3$ |
| 193 | H | H | —NHCO$_2$C$_2$H$_5$ |
| 194 | H | H | —NHCO$_2$C$_4$H$_9$ |
| 195 | H | H | —NHCO$_2$CH(CH$_3$)$_2$ |
| 196 | H | H | —NHCO$_2$C$_2$H$_4$OCH$_3$ |
| 197 | H | H | NHCO$_2$CH$_2$CF$_3$ |
| 198 | H | H | ![structure: NH-C(═O)-O-cyclopentyl] |
| 199 | H | H | ![structure: NH-C(═O)-O-cyclohexyl] |
| 200 | H | H | ![structure: NH-C(═O)-O-phenyl] |
| 201 | H | H | —N(CH$_3$)CO$_2$CH$_3$ |
| 202 | H | H | —N(C$_3$H$_7$)CO$_2$CH$_3$ |
| 203 | H | H | —NH(C═O)NHC$_2$H$_5$ |
| 204 | H | H | ![structure: N-methyl pyrrole] |
| 205 | H | H | ![structure: 3,5-dimethyl pyrazole] |

TABLE 1-continued
| | | | |
|---|---|---|---|
| 206 | H | H | 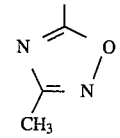 |
| 207 | H | H | 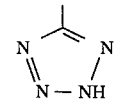 |
| 208 | H | H | 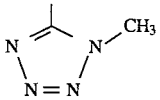 |
| 209 | H | H | 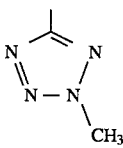 |
| 210 | H | H | 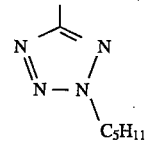 |
| 211 | H | H | 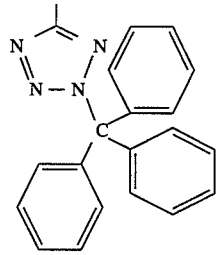 |
| 212 | H | H | 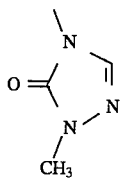 |
| 213 | F | H | F |
| 214 | F | H | —OC$_3$H$_7$ |
| 215 | —OCH$_3$ | H | —OC$_3$H$_7$ |
| 216 | —SCH$_3$ | H | —OC$_3$H$_7$ |
| 217 | —S(O)CH$_3$ | H | —OC$_3$H$_7$ |
| 218 | —C≡N | H | —OC$_3$H$_7$ |
| 219 | —NO$_2$ | H | —OC$_3$H$_7$ |
| 220 | H | —NO$_2$ | —OC$_3$H$_7$ |
| 221 | H | —NH$_2$ | —OC$_3$H$_7$ |
| 222 | —N(CH$_3$)$_2$ | H | —OC$_3$H$_7$ |
| 223 | —OH | H | —OC$_3$H$_7$ |
| 224 | —OSi(CH$_3$)$_2$C(CH$_3$)$_3$ | H | —OC$_3$H$_7$ |
| 225 | 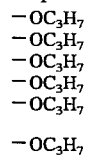 | H | —OC$_3$H$_7$ |

TABLE 1-continued

| Where U is —(CH₂)ₙ—, and n is 1; Q is —OH; | and | R¹ and R² are 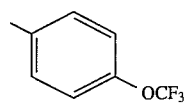 |
|---|---|---|

| Cmpd. No. | R | Cmpd. No. | R |
|---|---|---|---|
| 226 | furan-2-yl (O at position 2) | 227 | furan-3-yl |
| 228 | thiophen-2-yl (S) | 229 | N-methylpyrrol-2-yl |
| 230 | 3-methyl-1-propyl-pyrrol-4-yl | 231 | 4-fluoroindol-3-yl |
| 232 | pyridin-2-yl | 233 | 5-propoxypyridin-2-yl |
| 234 | pyridin-3-yl | 235 | 2-propoxypyrimidin-5-yl |

| Where Q is —OH; | R is 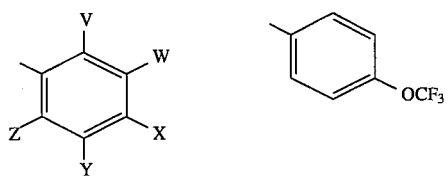 where V, W, Y and Z are hydrogen; and | R¹ and R² are |
|---|---|---|

| Cmpd. No. | U | X |
|---|---|---|
| 236 | isobutyl (CH₃ branch) | —OC₂H₅ |
| 237 | 1-methylcyclopropyl-ethyl | H |
| 238 | 4-isopropylphenyl-OCH₃ | —OCH₃ |

TABLE 1-continued
| 239 | 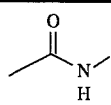 | H |
Note: the carbonyl is adjacent to the piperidine ring.
Where Q is —OH; and $R^1$ and $R^2$ are
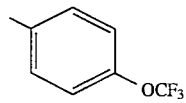
| Cmpd. No. | U | R |
|---|---|---|
| 240 |  | 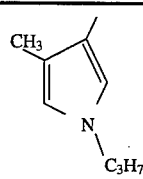 |
Where Q is —OH; U is —$(CH_2)_n$—, where n is 1; and R is
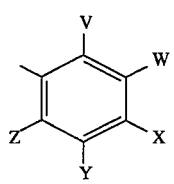
where V, W, Y and Z are hydrogen
| Cmpd. No. | X | $R^1$ | $R^2$ |
|---|---|---|---|
| 241 | —$OC_3H_7$ | 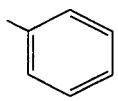 | 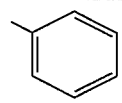 |
| 242 | H | 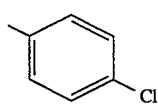 | 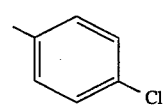 |
| 243 | —$OC_3H_7$ | 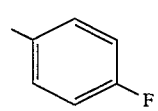 | 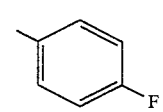 |
| 244 | —$OC_3H_7$ | 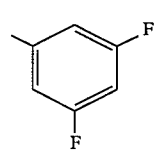 | 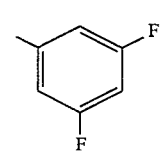 |
| 245 | —$OC_3H_7$ | 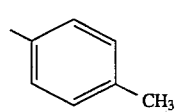 | 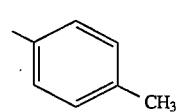 |
| 246 | —$OC_3H_7$ | 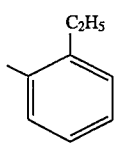 | 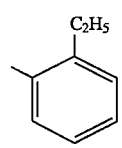 |

TABLE 1-continued

| | | | |
|---|---|---|---|
| 247 | —OCH₃ | 4-C₂H₅-C₆H₄ | 4-C₂H₅-C₆H₄ |
| 248 | —OC₃H₇ | 4-CH(CH₃)₂-C₆H₄ | 4-CH(CH₃)₂-C₆H₄ |
| 249 | —OC₃H₇ | 4-CH₂OCH₃-C₆H₄ | 4-CH₂OCH₃-C₆H₄ |
| 250 | —OC₃H₇ | 2-CF₃-C₆H₄ | 2-CF₃-C₆H₄ |
| 251 | —OC₃H₇ | 3-CF₃-C₆H₄ | 3-CF₃-C₆H₄ |
| 252 | —OC₃H₇ | 4-CF₃-C₆H₄ | 4-CF₃-C₆H₄ |
| 253 | —OC₃H₇ | 4-C₃F₇-C₆H₄ | 4-C₃F₇-C₆H₄ |
| 254 | —OC₃H₇ | 3,5-(CF₃)₂-C₆H₃ | 3,5-(CF₃)₂-C₆H₃ |
| 255 | —OC₃H₇ | 4-OH-C₆H₄ | 4-OH-C₆H₄ |
| 256 | —OC₃H₇ | 4-OCH₃-C₆H₄ | 4-OCH₃-C₆H₄ |
| 257 | —OC₃H₇ | 4-SCH₃-C₆H₄ | 4-SCH₃-C₆H₄ |
| 258 | —OC₃H₇ | 4-CH₃-C₆H₄ | 4-OCF₃-C₆H₄ |
| 259 | —OC₃H₇ | 4-OCH₃-C₆H₄ | 4-OCF₃-C₆H₄ |
| 260 | —OC₃H₇ | 4-CF₃-C₆H₄ | 4-OCF₃-C₆H₄ |

TABLE 1-continued

| # | R | Ar1 | Ar2 |
|---|---|---|---|
| 261 | 1,3-dioxolan-2-yl (CH with two O in 5-ring) | 2-OCF₃-phenyl (via CH₃) | 4-OCF₃-phenyl (via CH₃) |
| 262 | —OC₃H₇ | 2-Cl-4-methyl-phenyl with OCH₃ | 4-OCF₃-phenyl |
| 263 | —OC₃H₇ | 2-F-4-methyl-phenyl with OCH₃ | 4-OCF₃-phenyl |
| 264 | —OC₃H₇ | 2-C₂H₅-4-methyl-phenyl with OCH₃ | 4-OCF₃-phenyl |
| 265 | —OC₃H₇ | 2,4-di-OCH₃-phenyl(methyl) | 4-OCF₃-phenyl |
| 266 | —OC₃H₇ | 2-CF₃-4-OCH₃-phenyl(methyl) | 4-OCF₃-phenyl |
| 267 | —OC₃H₇ | 4-N(CH₃)₂-phenyl(methyl) | 4-N(CH₃)₂-phenyl(methyl) |
| 268 | —OC₃H₇ | 4-OSO₂CH₃-phenyl(methyl) | 4-OSO₂CH₃-phenyl(methyl) |
| 269 | —OC₃H₇ | 4-OSO₂CF₃-phenyl(methyl) | 4-OSO₂CF₃-phenyl(methyl) |
| 270 | —OC₃H₇ | 4-SO₂N(CH₃)-phenyl(methyl) | 4-SO₂N(CH₃)-phenyl(methyl) |
| 271 | —OC₃H₇ | 4-C(O)NH-C(CH₃)₂-CH₂OH-phenyl(methyl) | 4-C(O)NH-C(CH₃)₂-CH₂OH-phenyl(methyl) |
| 272 | —OC₃H₇ | 4-[C(=N-C(CH₃)₂-CH₂-O-)]-phenyl(methyl) | 4-C(O)NH-C(CH₃)₂-CH₂OH-phenyl(methyl) |

TABLE 1-continued
| | | | |
|---|---|---|---|
| 273 | —OC₃H₇ | | |
| 274 | —OC₃H₇ | | |
| 275 | —OC₃H₇ | | |
| Where U is —(CH₂)ₙ—, and n is 1; | R is | and | R¹ and R² are |
|---|---|---|---|
| |  where V, W, Y, and Z are hydrogen; and X is —OC₃H₇ | | |
| Cmpd. No. | Q | Cmpd. No. | Q |
|---|---|---|---|
| 276 | H | 277 | —SH |
The following compounds are N-Oxides:
| Where U is —(CH₂)ₙ—, and n is 1; | R is | and | R¹ and R² are |
|---|---|---|---|
| Q is —OH; | 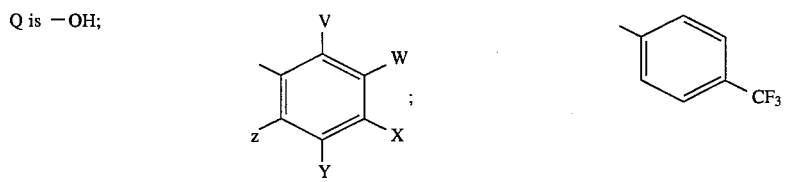 where V, W, Y, and Z are hydrogen | | |
| Cmpd. No. | X | Cmpd. No. | X |
|---|---|---|---|
| 278 | Cl | 279 | F |
| 280 | —OCH₃ | 281 | —OC₃H₇ |
| 282 | —OCH(CH₃)C₂H₅ | 283 | —OCH(CH₃)₂ |
| 284 | —OCH₂-cyclopropyl | 285 | —OCH₂C≡CH |
| 286 | —OCHF₂ | 287 | —OCF₃ |
| 288 | —NHCO₂CH₃ | | |

TABLE 1-continued

| Where U is $-(CH_2)_n-$, and n is 1; Q is $-OH$; | R is (phenyl ring with V, W, X, Y, Z substituents) where Y and Z are hydrogen | and | $R^1$ and $R^2$ are (phenyl with $-OCF_3$) |
|---|---|---|---|

| Cmpd. No. | V | W | X |
|---|---|---|---|
| 289 | H | H | Cl |
| 290 | H | H | F |
| 291 | H | H | $-CH_3$ |
| 292 | H | H | $-OCH_2OC_2H_5$ |
| 293 | $-OCH_3$ | H | H |
| 294 | H | H | $-OCH_3$ |
| 295 | H | H | $-OC_3H_7$ |
| 296 | H | H | $-OCH(CH_3)_2$ |
| 297 | H | H | $-OCH(CH_3)C_2H_5$ |
| 298 | H | H | $-OCH_2$-cyclopropyl |
| 299 | H | H | $-OCH_2$-C(CH_3)-cyclopropyl |
| 300 | H | H | $-OCH_2$-(2-methylcyclopropyl) |
| 301 | H | H | $-OCH_2$-(1-phenylcyclopropyl) |
| 302 | H | H | $-OCH_2$-(2-phenylcyclopropyl) |
| 303 | H | H | $-OCH_2$-cyclobutyl |
| 304 | H | H | $-OCHF_2$ |
| 305 | H | H | $-OCF_3$ |
| 306 | H | H | $-O$-cyclohexyl |
| 307 | H | H | $-OCH_2OCH_3$ |
| 308 | H | H | $-OCH(C_2H_5)CH_2OCH_3$ |
| 309 | H | H | $-OCH_2OC_2H_4OCH_3$ |
| 310 | H | H | $-OC_3H_6CH=CH_2$ |
| 311 | H | H | $-OCH_2C\equiv CCH_3$ |
| 312 | H | H | $-OCH(C_2H_5)CO_2C_2H_5$ |
| 313 | H | H | $-OCH_2CH_2O-$ |
| 314 | H | H | $-N=C(C_2H_5)O-$ |

TABLE 1-continued

| Cmpd. No. | | | |
|---|---|---|---|
| 315 | H | H | (phenyl) |
| 316 | H | H | (triazinone structure with N-CH$_3$) |
| 317 | H | H | $-CO_2C_2H_5$ |
| 318 | H | H | $-CO_2C_4H_9$ |
| 319 | H | H | $-(C=O)NHCH_2C\equiv CH$ |
| 320 | H | H | $-(C=O)N(CH_3)_2$ |
| 321 | H | H | $-NH-C(=O)-$phenyl |
| 322 | H | H | $-NHCO_2CH_3$ |
| 323 | H | H | $-N(CH_3)CO_2CH_3$ |
| 324 | H | H | $-NH-C(=O)-O-$cyclohexyl |

Where Q is $-OH$; U is $-(CH_2)_n-$, where n is 1; and R is

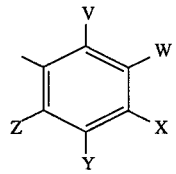

where V, W, Y and Z are hydrogen

| Cmpd. No. | X | R$^1$ | R$^2$ |
|---|---|---|---|
| 325 | $-OC_3H_7$ | 2-ethylphenyl ($C_2H_5$) | 2-ethylphenyl ($C_2H_5$) |
| 326 | $-OC_3H_7$ | 4-($CF_3$)phenyl | 4-($OCF_3$)phenyl |

| Where Q is $-OH$; | R is | R$^1$ and R$^2$ are |
|---|---|---|
| | 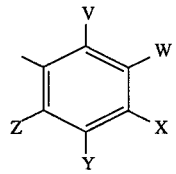 where V, W, Y and Z are hydrogen; and | 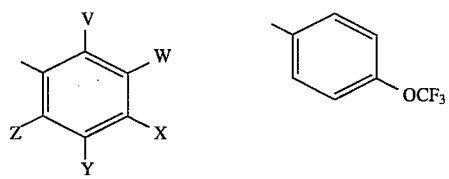 |

TABLE 1-continued

| Cmpd. No. | U | X |
|---|---|---|
| 327 |  | —OC$_2$H$_5$ |
| 328 |   Note: the cyclopropane ring is adjacent to the phenyl ring. | H |
| 329 | 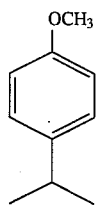 | —OCH$_3$ |

The following compounds are Hydrochloride Salts:

Where Q is —OH; U is —(CH$_2$)$_n$—, where n is 1; and R is

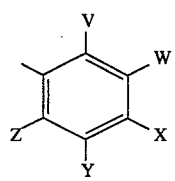

where V, W, Y and Z are hydrogen

| Cmpd. No. | X | R$^1$ | R$^2$ |
|---|---|---|---|
| 330 | H | 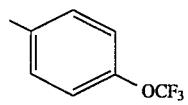 | 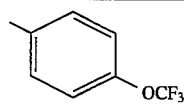 |
| 331 | —OC$_3$H$_7$ | 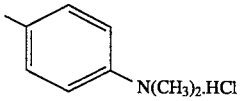 | 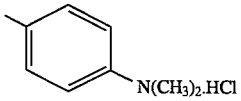 |
| 332 | —OC$_3$H$_7$ | 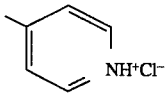 | 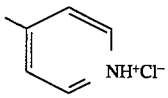 |

The following compound is not a Hydrochloride Salt:

Where U is —(CH$_2$)$_n$—, and n is 1;

Q is —OH;

R is

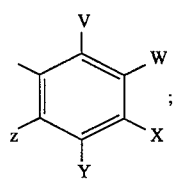

and

R$^1$ and R$^2$ are

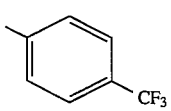

where Y and Z are hydrogen

TABLE 1-continued

| Cmpd. No. | V | W | X |
|---|---|---|---|
| 333 | H | H | $-P(=O)(O-C_2H_5)(O-C_2H_5)$ |

TABLE 2

Characterizing Data

| # | Data | # | Data | # | Data | # | Data |
|---|---|---|---|---|---|---|---|
| 1 | 90–93° C. | 44 | THICK COLORLESS OIL | 106 | GLASSY SOLID | 151 | FOAMY SOLID |
| 2 | OIL | 45 | OIL | 107 | GUMMY OIL | 152 | GUMMY SOLID |
| 3 | OIL | 46 | OIL | 108 | GUMMY OIL | 153 | OIL |
| 4 | OIL | 47 | OIL | 109 | GUMMY SOLID | 154 | FOAMY SOLID |
| 5 | — | 48 | OIL | 110 | GUMMY SOLID | 155 | OIL |
| 6 | OIL | 49 | 53–57° C. | 111 | OIL | 156 | 116.0–118.0 C. |
| 7 | OIL | 50 | 53–55° C. | 112 | FOAM | 157 | 139–142 C. |
| 8 | OIL | 51 | OIL | 113 | GUMMY OIL | 158 | FOAMY SOLID |
| 9 | 123–128° C. | 52 | VISCOUS OIL | 114 | PALE OIL | 159 | OIL |
| 10 | PASTE | 53 | 109–110° C. | 115 | GUMMY SOLID | 160 | FOAM |
| 11 | OIL | 54 | 96–98° C. | 116 | PALE OIL | 161 | 71.0–73.0 C. |
| 12 | 55–59° C. | 55 | 55–62° C. | 117 | CLEAR AMBER OIL | 162 | 60–63 C. |
| 13 | GUMMY OIL | 56 | NON CRYSTALLINE SOLID | 118 | PALE GUMMY SOLID | 163 | OIL |
| 14 | OIL | 57 | OIL | 119 | 133–136 C. | 164 | 58–60 C. |
| 15 | OIL | 58 | 65–70° C. | 120 | 105–108 C. | 165 | GUM |
| 16 | SOLID | 59 | LIQUID | 121 | FOAMY SOLID | 166 | FOAM |
| 17 | OIL | 60 | OIL | 122 | WHITE GLASSY SOLID | 167 | GUM |
| 18 | OIL | 61 | OIL | 123 | 115–118 C. | 168 | GUM |
| 19 | 75–80° C. | 62 | GUMMY SOLID | 124 | GUMMY SOLID | 169 | GUM |
| 20 | OIL | 63 | GUMMY SOLID | 125 | 110–114 C. | 170 | 71–72 C. |
| 21 | SEMI-SOLID | 64 | SEMI-SOLID | 126 | OIL | 171 | FOAM |
| 22 | 50° C. | 65 | LIQUID | 127 | OIL | 172 | OIL |
| 23 | WAXY SOLID | 66 | OIL | 128 | VISCOUS OIL | 173 | OIL |
| 24 | 86–96° C. | 67 | OIL | 129 | VISCOUS OIL | 174 | FOAM |
| 25 | GEL | 68 | OIL | 130 | 56–58 C. | 175 | 90–96 C. |
| 26 | VISCOUS OIL | 69 | OIL | 131 | AMBER OIL | 176 | OIL |
| 27 | OIL | 70 | FOAM | 177 | OIL | 220 | 60–62 C. |
| 28 | OIL | 71 | OIL | 178 | OIL | 221 | 75–77 C. |
| 29 | OIL | 72 | OIL | 179 | OIL | 222 | VISCOUS OIL |
| 30 | — | 73 | FOAM | 180 | BLACKISH SEMI-SOLID | 223 | SOLID FOAM |
| 31 | OIL | 74 | VISCOUS OIL | 181 | 85–92 C. | 224 | SOLID FOAM |
| 32 | OIL | 75 | GUM | 182 | OIL | 225 | GUMMY FOAM |
| 33 | LIQUID | 76 | 61–64 C. | 183 | OIL | 226 | VISCOUS OIL |
| 34 | STICKY OIL | 77 | GUMMY SOLID | 184 | THICK OIL | 227 | VISCOUS OIL |
| 35 | SEMI-SOLID | 78 | OIL | 185 | 123–125 C. | 228 | VISCOUS OIL |
| 36 | LIQUID | 79 | 55–56 C. | 186 | 148–151 C. | 229 | VISCOUS OIL |
| 37 | OIL | 80 | LIQUID | 187 | OIL | 230 | GUM |
| 38 | SEMI-SOLID | 81 | COLORLESS VISCOUS OIL | 188 | GLASSY SOLID | 231 | 76–88 C. |
| 39 | OIL | 82 | SEMI-SOLID | 189 | GLASSY SOLID | 232 | 54–55 C. |
| 40 | WAXY SOLID | 83 | VISCOUS OIL | 190 | 64–70 C. | 233 | OIL |
| 41 | OIL | 84 | VISCOUS OIL | 191 | 85–93 C. | 234 | 108–110 C. |
| 42 | LIQUID | 85 | VISCOUS OIL | 192 | GLASSY SOLID | 235 | GUM |
| 43 | SOLID | 86 | VISCOUS OIL | 193 | 88–92 C. | 236 | GUMMY SOLID |
| 87 | GUMMY SOLID | 132 | OIL | 194 | 165–169 C. | 237 | OIL |
| 88 | OIL | 133 | FOAMY SOLID | 195 | 76–85 C. | 238 | 84–87 C. |
| 89 | OIL | 134 | OIL | 196 | 150–152 C. | 239 | FOAM |
| 90 | OIL | 135 | OIL | 197 | WHITE SOLID | 240 | 155–157 C. |
| 91 | OIL | 136 | SOLID | 198 | WHITE SOLID | 241 | OIL |
| 92 | SEMI-SOLID | 137 | OIL | 199 | WHITE SOLID | 242 | FOAM |
| 93 | OIL | 138 | SEMI-SOLID | 200 | WHITE GLASSY SOLID | 243 | OIL |
| 94 | 160–163 C. | 139 | OIL | 201 | OIL | 244 | FOAM |
| 95 | OIL | 140 | SOLID | 202 | OIL | 245 | VISCOUS OIL |
| 96 | SEMI-SOLID | 141 | OIL | 203 | 67–78 C. | 246 | SYRUP |
| 97 | SOLID | 142 | OIL | 204 | OIL | 247 | 104–108 C. |
| 98 | PASTE | 143 | OIL | 205 | FOAM | 248 | OIL |
| 99 | 78–81 C. | 144 | OIL | 206 | FOAM | 249 | LIQUID |
| 100 | 68.0–71.0 C. | 145 | 55–57 C. | 207 | 240 DEC | 250 | SOLID FOAM |
| 101 | OIL | 146 | OIL | 208 | FOAM | 251 | SEMI SOLID |
| 102 | 96–101 C. | 147 | OIL | 209 | OIL | 252 | SOLID FOAM |
| 103 | OIL | 148 | OIL | 210 | OIL | 253 | LIQUID |
| 104 | OIL | 149 | 160–161 C. | | | | |
| 105 | OIL | 150 | 117–119 C. | | | | |

TABLE 2-continued

Characterizing Data

| | | | |
|---|---|---|---|
| 211 | FOAM | 254 | SOLID FOAM |
| 212 | FOAM | 255 | 126.0–127.0 C. |
| 213 | FOAMY SOLID | 256 | 49–51 C. |
| 214 | GUMMY SOLID | 257 | FOAM |
| 215 | 86–88 C. | 258 | THICK OIL |
| 216 | 80–82 C. | 259 | OIL |
| 217 | 56–58 C. | 260 | GLASSY SOLID |
| 218 | SOLID FOAM | 261 | GUMMY FOAMY SOLID |
| 219 | FOAM | 262 | OIL |
| 263 | OIL | 299 | 189–191 C. |
| 264 | SEMI SOLID | 300 | 187–188 C. |
| 265 | SEMI-SOLID | 301 | 171–172 C. |
| 266 | SOLID FOAM | 302 | 99–101 C. |
| 267 | 91 DEC | 303 | 184–185 C. |
| 268 | 157–158 C. | 304 | 182–184 C. |
| 269 | THICK OIL | 305 | 188–189 C. |
| 270 | SEMI-SOLID | 306 | 125–128 C. |
| 271 | FOAM | 307 | 181–182 C. |
| 272 | FOAM | 308 | 182.0–184.0 C. |
| 273 | FOAM | 309 | SOLID |
| 274 | OIL | 310 | 184–185 C. |
| 275 | 82–84 C. | 311 | 181–185 C. |
| 276 | 76–80 C. | 312 | 96–98 C. |
| 277 | GUMMY OIL | 313 | 192–194 DEC |
| 278 | 219.5–220 C. | 314 | 164–166 DEC |
| 279 | 211–211.5 C. | 315 | 103–107 C. |
| 280 | 216–217 C. | 316 | FOAM |
| 281 | 198–200 DEC | 317 | 163–165 C. |
| 282 | 209–210 C. | 318 | FOAM |
| 283 | 208–209.5 C. | 319 | 162–165 C. |
| 284 | 109.0 –110.0 C. | 320 | 156–160 C. |
| 285 | 207.5–208.5 C. | 321 | GUMMY SOLID |
| 286 | 202–203 C. | 322 | 178–182 C. |
| 287 | 207–208.5 C. | 323 | 179–181 C. |
| 288 | 194–197 C. | 324 | WHITE SOLID |
| 289 | 166 C. DEC | 325 | 189–190 C. |
| 290 | 187–188 C. | 326 | 202–205 C. |
| 291 | 141–146 C. | 327 | 102–105 C. |
| 292 | 186–187 C. | 328 | 214–215 C. |
| 293 | 190–195 C. | 329 | 75–78 C. |
| 294 | 179–180 C. | 330 | 142–144 C. |
| 295 | 210–211 C. | 331 | 170 DEC |
| 296 | 181–182 C. | 332 | 193.0–195.0 C. |
| 297 | 188.0–192.0 C. | 333 | WHITE FOAM |
| 298 | 197–199 C. | | |

TABLE 3

Insecticidal Activity When Incorporated into the Diet of Tobacco Budworm

| Cmpd. No. | Rate of Application[1] | Percent Growth Inhibition[2,3] | $pI_{50}$[4] | Percent Mortality[5] | $pLC_{50}$[6] |
|---|---|---|---|---|---|
| 1 | 4 | 22 | <4.0 | 0 | — |
| 2 | 4 | 99 | 5.4 | 30 | <4.0 |
| 3 | 4 | 53 | 4.1 | 0 | — |
| 4 | 4 | 51 | 4.0 | 0 | — |
| 5 | 4 | 51 | 4.0 | 0 | — |
| 6 | 4 | 95 | 5.1 | 5 | <3.5 |
| 7 | 4 | 100 | 5.9 | 100 | 4.6 |
| 8 | 4 | 56 | 4.0 | 0 | — |
| 9 | 3.5 | 16 | — | 0 | — |
| 10 | 4 | 69 | 4.3 | 0 | — |
| 11 | 4 | 76 | 4.6 | 0 | — |
| 12 | 4 | 20 | — | 0 | — |
| 13 | 4 | 100 | 5.6 | 60 | 4.2 |
| 14 | 4 | 97 | 5.1 | 0 | <3.5 |
| 15 | 4 | 100 | 5.6 | 90 | 4.5 |
| 16 | 4 | 99 | 5.6 | 85 | 4.5 |
| 17 | 4 | 100 | 5.7 | 90 | 4.5 |
| 18 | 4 | 90 | 4.7 | 0 | — |
| 19 | 4 | 87 | 4.5 | 0 | — |
| 20 | 4 | 69 | 4.0 | 0 | — |
| 21 | 4 | 100 | 5.6 | 75 | 4.2 |
| 22 | 4 | 100[a] | 6.0 | 70[a] | 4.3[a] |
| 23 | 4 | 99 | 5.6 | 30 | <4.0 |
| 24 | 4 | 100[a] | 6.1[a] | 100[a] | 4.6[a] |
| 25 | 4 | 98 | 5.6 | 25 | <4.0 |
| 26 | 4 | 98 | 5.1 | 15 | — |
| 27 | 5 | 100 | 6.2 | 80 | 3.4 |
| 28 | 4 | 100[b] | 6.5[b] | 100[b] | 5.4[a] |
| 29 | 4 | 100 | 6.5 | 100 | 5.8 |
| 31 | 4 | 100 | 5.7 | 100 | 5.0 |
| 32 | 4 | 100 | 5.6 | 100 | 4.5 |
| 33 | 4 | 99 | 5.4 | 65 | 4.2 |
| 34 | 4 | 100 | 6.0 | 90 | 4.5 |
| 35 | 4 | 99 | 5.2 | 55 | 4.2 |
| 36 | 4 | 100 | 5.5 | 95 | 4.5 |
| 37 | 4 | 98 | 5.3 | 35 | 4.0 |
| 38 | 4 | 99 | 5.0 | 45 | 4.1 |
| 39 | 4 | 100 | 6.2 | 100 | 4.6 |
| 40 | 4 | 98 | 5.4 | 30 | <4.6 |
| 41 | 4 | 97 | 5.1 | 0 | <4.6 |
| 42 | 4 | 100 | 6.5 | 100 | 5.5 |
| 43 | 4 | 100 | 6.4 | 100 | 5.5 |
| 44 | 4 | 100 | 5.6 | 65 | 4.3 |
| 45 | 4 | 100 | 5.6 | 100 | 4.9 |
| 46 | 4 | 100 | 6.2 | 100 | 4.9 |
| 47 | 4 | 100 | 6.4 | 100 | 5.5 |
| 48 | 4 | 100 | 6.4 | 100 | 5.6 |
| 49 | 4 | 77 | 4.6 | 0 | — |
| 50 | 4 | 98 | 5.0 | 40 | <4.0 |
| 51 | 3.5 | −10 | — | 0 | — |
| 52 | 4 | 100[b] | 6.2 | 100[b] | 4.6[b] |
| 53 | 4 | 97 | 5.7 | 25 | <4.0 |
| 54 | 4 | 81 | 4.7 | 0 | — |
| 55 | 4 | 100[b] | 6.0[b] | 100[b] | 4.5[b] |
| 56 | 4 | 95 | 5.1 | 5 | — |
| 57 | 4 | 100[b] | 6.2[b] | 100[b] | 5.3[b] |
| 58 | 4 | 100 | 5.6 | 100 | 4.8 |
| 59 | 4 | 82 | 4.5 | 0 | <3.5 |
| 60 | 4 | 100 | 5.8 | 100 | 5.4[b] |
| 61 | 4 | 84 | 5.2 | 0 | — |
| 62 | 4 | 0 | 3.6 | 0 | — |
| 63 | 4 | 100 | 5.9 | 90 | 4.5 |
| 64 | 4 | 100 | 5.4 | 60 | 4.3 |
| 65 | 4 | 100[b] | 6.1[b]0 | 100[b] | 4.9[b] |
| 66 | 4 | 95 | 4.7 | 0 | — |
| 67 | 4 | 100 | 5.5 | 70 | 4.3 |
| 68 | 4 | 100 | 6.0 | 55 | 4.1 |
| 69 | 4 | 100 | 5.5 | 55 | 4.1 |
| 70 | 4 | 99 | 5.7 | 35 | — |
| 71 | 4 | 91 | 4.7 | 5 | — |
| 72 | 4 | 56 | 4.1 | 0 | — |
| 73 | 4 | 8 | — | 0 | — |
| 74 | 4 | 99 | 5.4 | 60 | 4.2 |
| 75 | 4 | 100 | 5.6 | 100 | 4.9 |
| 76 | 4 | 3 | — | 0 | — |
| 77 | 4 | 20 | — | 0 | — |
| 78 | 4 | 100[a] | 7.0[a] | 100[a] | 5.8[a] |
| 79 | 4 | 100 | 6.0 | 100 | 5.5 |
| 80 | 4 | 100 | 6.2 | 100 | 5.5 |
| 81 | 4 | 100 | 5.5 | 100 | 5.2 |
| 82 | 4 | 100 | 5.2 | 100 | 4.6 |
| 83 | 4 | 99 | 5.1 | 70 | 4.3 |
| 84 | 4 | 40 | <4.0 | 0 | — |
| 85 | 4 | 100 | 5.6 | 100 | 5.5 |
| 86 | 4 | 100 | 5.4 | 100 | 4.6 |
| 87 | 4 | 34 | 3.9 | 0 | — |
| 88 | 4 | 100 | 6.1 | 100 | 5.1 |
| 89 | 4 | 100 | >6.0 | 100 | 5.5 |
| 90 | 4 | 100[a] | 6.1[a] | 100[a] | 5.1[a] |
| 91 | 4 | 100 | 5.4 | 0 | 4.2 |
| 92 | 4 | 100 | 6.2 | 100 | 4.9 |
| 93 | 4 | 100 | 5.6 | 100 | 4.6 |

TABLE 3-continued

Insecticidal Activity When Incorporated into the Diet of Tobacco Budworm

| Cmpd. No. | Rate of Application[1] | Percent Growth Inhibition[2,3] | pI$_{50}$[4] | Percent Mortality[5] | pLC$_{50}$[6] |
|---|---|---|---|---|---|
| 94 | 4 | 100 | 6.3 | 100 | 5.6 |
| 95 | 4 | 100 | 5.6 | 100 | 5.0 |
| 96 | 4 | 100 | 6.2 | 100 | 4.6 |
| 97 | 4 | 100 | 6.3 | 100 | 4.6 |
| 98 | 4 | 100 | 6.1 | 100 | 4.8 |
| 99 | 4 | 0 | — | 0 | — |
| 100 | 4 | 98 | 5.4 | 20 | <3.5 |
| 101 | 4 | 99 | 5.5 | 0 | 4.2 |
| 102 | 4 | 100[a] | 6.0[a] | 100[a] | 4.8[a] |
| 103 | 4 | 75 | 4.3 | 0 | — |
| 104 | 4 | 100 | 5.8 | 100 | 5.5 |
| 105 | 4 | 100 | 5.5 | 100 | 5.0 |
| 106 | 4 | 98 | 5.4 | 20 | 3.6 |
| 107 | 4 | 98 | 5.4 | 25 | 3.8 |
| 108 | 4 | 97 | 5.4 | 0 | — |
| 109 | 4 | 67 | 4.5 | 0 | — |
| 110 | 4 | 97[b] | 5.7[b] | 15[b] | 3.8[b] |
| 111 | 4 | 99 | 5.8 | 50 | 4.2 |
| 112 | 4 | 100 | >6.0 | 100 | 5.5 |
| 113 | 4 | 100 | — | 100 | 5.5[b] |
| 114 | 4 | 100[b] | 7.0 | 98[b] | 5.1[b] |
| 115 | 4 | 100 | — | 100 | 5.6[b] |
| 116 | 4 | 100[b] | — | 88[b] | 4.5[b] |
| 117 | 4 | 100[b] | 6.2 | 100[b] | 5.0[b] |
| 118 | 4 | 97 | 5.1 | 15 | 3.7 |
| 119 | 4 | 63 | 4.2 | 0 | — |
| 120 | 4 | 99 | 6.1 | 85 | 4.7 |
| 121 | 4 | 100 | 6.5 | 100 | 6.0 |
| 122 | 4 | 100 | 6.2 | 100 | 5.5 |
| 123 | 4 | 100 | 6.8[b] | 100 | 6.4[b] |
| 124 | 4 | 100 | 5.7 | 100 | 5.4 |
| 125 | 4 | 98 | 5.0 | 0 | 3.7 |
| 126 | 4 | 100 | 5.4 | 85 | 4.4 |
| 127 | 4 | 95[b] | 4.7[b] | 18[b] | <3.5[b] |
| 128 | 4 | 98 | 5.4 | 70 | 4.3 |
| 129 | 4 | 100 | 5.5 | 60 | 4.2 |
| 130 | 4 | 100 | 6.7 | 100 | 5.7 |
| 131 | 4 | 91 | 4.5 | 0 | — |
| 132 | 4 | 100 | 6.5[b] | 100 | 5.8[b] |
| 133 | 4 | 100 | 5.9 | 100 | 4.6 |
| 134 | 4 | 100 | 6.4 | 100 | 4.6 |
| 135 | 4 | 14 | — | 0 | — |
| 136 | 4 | 100[b] | 5.6[b] | 100[b] | 5.0[b] |
| 137 | 4 | 100 | 6.3 | 100 | 4.9 |
| 138 | 4 | 100 | 6.2 | 100 | 5.1 |
| 139 | 4 | 100 | 6.5 | 100 | 5.6 |
| 140 | 4 | 100 | 6.2 | 100 | 5.1 |
| 141 | 4 | 100 | 6.1 | 100 | 5.6 |
| 142 | 4 | 100 | 6.7 | 100 | 5.4 |
| 143 | 4 | 82 | 4.6 | 0 | — |
| 144 | 4 | −8 | — | 0 | — |
| 145 | 4 | 100 | 5.6 | 100 | 5.5 |
| 146 | 4 | 99 | 5.1 | 85 | 4.5 |
| 147 | 4 | 7 | 3.8 | 0 | — |
| 148 | 4 | 100 | 6.2 | 100 | 5.0 |
| 149 | 4 | 80 | 4.4 | 0 | — |
| 150 | 4 | 100 | 6.6 | 100 | 5.6 |
| 151 | 4 | 100 | 5.6 | 100 | 5.5 |
| 152 | 4 | 100 | 5.5 | 100 | 5.1 |
| 153 | 4 | 97 | 5.4 | 15 | 3.8 |
| 154 | 4 | 97 | 5.2 | 10 | — |
| 155 | 4 | 100 | 5.8 | 100 | 4.9 |
| 156 | 4 | 96 | 5.0 | 0 | <3.5 |
| 157 | 4 | 1 | — | 0 | — |
| 158 | 4 | 100 | 6.2 | 100 | 5.1 |
| 159 | 4 | 100 | 6.4 | 100 | 5.8 |
| 160 | 4 | 82[b] | 4.5[b] | 18[b] | 3.7 |
| 161 | 4 | 15 | — | 0 | — |
| 162 | 4 | 98 | 5.1 | 65 | 4.2 |
| 163 | 4 | 100 | 6.1 | 100 | 5.0 |
| 164 | 4 | 99[b] | 5.5[b] | 58[b] | 4.9 |
| 165 | 4 | 80 | 4.4 | 0 | — |
| 166 | 4 | 100 | 5.6 | 75 | 4.3 |
| 167 | 4 | 92 | 5.1 | 0 | — |
| 168 | 4 | 99[b] | 5.5[b] | 20[b] | — |
| 169 | 4 | 100 | 5.9 | 45 | <4.0 |
| 170 | 4 | 99 | 5.6 | 60 | 4.2 |
| 171 | 4 | 96 | 5.1 | 0 | — |
| 172 | 4 | 99 | 5.5 | 35 | <4.0 |
| 173 | 4 | 100 | 5.9 | 100 | 5.0 |
| 174 | 4 | 100 | 5.4 | 65 | 4.2 |
| 175 | 4 | 100 | 6.5 | 100 | 5.6 |
| 176 | 4 | 100 | 6.5 | 100 | 5.5 |
| 177 | 4 | 100 | 6.6 | 100 | 5.6 |
| 178 | 4 | 97 | 5.6 | 35 | <4.0 |
| 180 | 4 | 95 | 4.6 | 15 | — |
| 181 | 4 | 88 | 4.7 | 5 | — |
| 182 | 4 | 100 | 5.5 | 60 | 4.2 |
| 183 | 4 | 100 | 5.5 | 100 | 4.9 |
| 184 | 4 | 100 | 5.5 | 55 | 4.1 |
| 185 | 4 | 62 | 4.2 | 0 | — |
| 186 | 4 | 90 | 4.9 | 5 | — |
| 187 | 4 | 100 | 5.5 | 100 | 4.5 |
| 188 | 4 | 100 | 5.6 | 0 | — |
| 189 | 4 | 96 | 5.1 | 20 | — |
| 190 | 4 | 100 | 5.7 | 90 | 4.5 |
| 191 | 4 | 100 | 5.7 | 100 | 5.1 |
| 192 | 4 | 100 | 6.8[b] | 100 | 5.5[b] |
| 193 | 4 | 100 | 6.5 | 100 | 6.0 |
| 194 | 4 | 100 | 6.4 | 100 | 5.5 |
| 195 | 4 | 100 | 6.6[b] | 100 | 6.1 |
| 196 | 4 | 100 | 6.2 | 100 | 4.9 |
| 197 | 4 | 100 | 6.5 | 100 | 5.9 |
| 198 | 4 | 100[b] | 5.7[b] | 100[b] | 5.3[b] |
| 199 | 4 | 85[b] | 4.9[b] | 8[b] | >3.5 |
| 200 | 4 | 94 | 5.0 | 5 | — |
| 201 | 4 | 100 | 6.1 | 100 | 5.2 |
| 202 | 4 | 100 | 6.1 | 100 | 5.5 |
| 203 | 4 | 96[b] | 4.9[b] | 5[b] | — |
| 204 | 4 | 100[b] | 5.5[b] | 100[b] | 5.5[b] |
| 205 | 4 | 100 | 5.5 | 100 | 4.6 |
| 206 | 4 | 100 | 6.0 | 100 | 5.1 |
| 207 | 4 | 92[b] | 5.0[b] | 0[b] | — |
| 208 | 4 | 79[a] | 4.5[a] | 0[a] | — |
| 209 | 4 | 100 | 6.6 | 100 | 5.6 |
| 210 | 4 | 49[b] | 4.0[b] | 0[b] | — |
| 211 | 3.5 | 2 | — | 0 | — |
| 212 | 4 | 98 | 5.4 | 35 | <4.0 |
| 213 | 4 | 100 | 5.5 | 95 | 4.8 |
| 214 | 4 | 100 | 5.6 | 100 | 5.4 |
| 215 | 4 | 100 | 6.1 | 100 | 5.5 |
| 216 | 4 | 99 | 5.1 | 45 | 4.1 |
| 217 | 4 | 17 | — | 0 | — |
| 218 | 4 | 79 | 4.4 | 5 | <3.5 |
| 219 | 4 | 98 | 4.5 | 15 | 3.6 |
| 220 | 4 | 100 | 5.5 | 80 | 4.9 |
| 221 | 4 | 100 | 5.5 | 80 | 4.4 |
| 222 | 4 | 100 | 5.5 | 100 | 4.6 |
| 223 | 4 | 100 | 5.6 | 95 | 4.5 |
| 224 | 4 | 100 | 5.7 | 100 | 4.8 |
| 225 | 4 | 1 | — | 0 | — |
| 226 | 4 | 92 | 4.9 | 5 | — |
| 227 | 4 | 95 | 4.5 | 0 | — |
| 228 | 4 | 95 | 4.9 | 5 | — |
| 229 | 4 | 94 | 5.0 | 0 | — |
| 230 | 4 | 63 | 4.2 | 5 | — |
| 231 | 4 | 100 | 5.5 | 100 | 4.6 |
| 232 | 4 | 88 | 4.8 | 0 | — |
| 233 | 4 | 99 | 5.7 | 40 | <4.0 |
| 234 | 4 | 44 | 3.9 | 0 | — |
| 235 | 4 | 97 | 5.0 | 0 | — |
| 236 | 4 | 99 | 5.5 | 50 | 4.2 |
| 237 | 4 | 14 | 3.5 | 0 | — |
| 238 | 4 | 7 | — | 0 | — |

TABLE 3-continued

Insecticidal Activity When Incorporated into the Diet of Tobacco Budworm

| Cmpd. No. | Rate of Application[1] | Percent Growth Inhibition[2,3] | $pI_{50}$[4] | Percent Mortality[5] | $pLC_{50}$[6] |
|---|---|---|---|---|---|
| 239 | 3.5 | 1 | — | 0 | — |
| 240 | 4 | 18 | 3.6 | 0 | — |
| 241 | 4 | 5 | <3.5 | 0 | — |
| 242 | 4 | 82 | 4.5 | 0 | — |
| 243 | 4 | 66[b] | 4.2[b] | 0 | — |
| 244 | 4 | 18 | 3.6 | 0 | — |
| 245 | 4 | 93 | 5.0 | 0 | — |
| 246 | 4 | 12 | <3.5 | 0 | — |
| 247 | 4 | 77 | 4.4 | 0 | — |
| 248 | 4 | 100 | 4.9 | 60 | 4.2 |
| 249 | 4 | 66 | 4.3 | 0 | — |
| 250 | 4 | 9 | 3.6 | 0 | — |
| 251 | 4 | 77 | 4.6 | 0 | — |
| 252 | 4 | 60 | 4.2 | 0 | — |
| 253 | 3.5 | 13 | — | 0 | — |
| 254 | 3.5 | 5 | — | 0 | — |
| 255 | 4 | 5 | — | 0 | — |
| 256 | 4 | 54 | 4.2 | 0 | — |
| 257 | 4 | 95 | 5.0 | 0 | — |
| 258 | 4 | 99 | 5.7 | 50 | 4.2 |
| 259 | 4 | 100 | 5.8 | 100 | 4.5 |
| 260 | 4 | 100 | 6.5 | 100 | 5.6 |
| 261 | 4 | 100 | 6.5 | 100 | 4.9 |
| 262 | 4 | 98 | 5.4 | 25 | 3.8 |
| 263 | 4 | 100 | 5.6 | 65 | 4.2 |
| 264 | 4 | 93 | 4.6 | 0 | — |
| 265 | 4 | 86 | 4.5 | 0 | — |
| 266 | 4 | 97 | 5.1 | 5 | <3.5 |
| 267 | 4 | 11 | 3.6 | 0 | — |
| 268 | 4 | −3 | <3.5 | 0 | — |
| 269 | 4 | 100[b] | 5.6[b] | 95[b] | 4.7[b] |
| 270 | 4 | 10 | — | 0 | — |
| 271 | 3.5 | 11 | — | 0 | — |
| 272 | 3.5 | 111 | — | 0 | — |
| 273 | 3.5 | 13 | — | 0 | — |
| 274 | 4 | −13 | — | 0 | — |
| 275 | 4 | −3 | — | 0 | — |
| 276 | 4 | 100 | 5.9 | 100 | 5.5 |
| 277 | 4 | 99 | 4.6 | 55 | 4.3 |
| 278 | 4 | 99 | 5.9 | 55 | 4.2 |
| 279 | 4 | 98 | 5.3 | 10 | 3.7 |
| 280 | 4 | 99 | 5.7 | 65 | 4.3 |
| 281 | 4 | 100 | 6.5 | 100 | 5.9 |
| 282 | 4 | 100 | 6.2 | 100 | 5.1 |
| 283 | 4 | 100 | 6.4 | 100 | 5.5 |
| 284 | 4 | 100 | 6.6 | 100 | 5.5 |
| 285 | 4 | 100 | 6.0 | 100 | 4.5 |
| 286 | 4 | 100 | 6.4 | 100 | 5.1 |
| 287 | 4 | 100 | 5.2 | 80 | 4.4 |
| 288 | 4 | 100 | 6.2 | 100 | 5.5 |
| 289 | 4 | 100 | 5.5 | 100 | 4.9 |
| 290 | 4 | 100 | 5.5 | 80 | 4.4 |
| 291 | 4 | 100 | 5.5 | 90 | 4.4 |
| 292 | 4 | 100 | 5.9 | 100 | 4.5 |
| 293 | 4 | 100 | 5.6 | 80 | 4.4 |
| 294 | 4 | 100 | 6.0 | 100 | 4.6 |
| 295 | 4 | 100 | 6.6 | 100 | 6.1 |
| 296 | 4 | 100[b] | 6.5[b] | 100[b] | 5.3[b] |
| 297 | 4 | 100 | 6.8 | 100 | 5.6 |
| 298 | 4 | 100 | 6.5 | 100 | 6.0 |
| 299 | 4 | 100 | 6.0 | 100 | 5.8 |
| 300 | 4 | 100 | 6.8 | 100 | 5.5 |
| 301 | 4 | 100 | 4.8 | 80 | 4.4 |
| 302 | 4 | 91 | 4.5 | 0 | — |
| 303 | 4 | 100 | 6.2 | 100 | 5.5 |
| 304 | 4 | 99 | 5.2 | 75 | 4.4 |
| 305 | 4 | 100 | 5.2 | 100 | 4.5 |
| 306 | 4 | 100 | 5.5 | 100 | 4.9 |
| 307 | 4 | 100 | 6.5 | 100 | 4.7 |
| 308 | 4 | 100 | 6.3 | 100 | 4.5 |
| 309 | 4 | 100 | 6.2 | 100 | 4.9 |
| 310 | 4 | 100 | 5.6 | 100 | 5.5 |
| 311 | 4 | 100[b] | 5.4[b] | 100[b] | 4.8[b] |
| 312 | 4 | 99 | 5.1 | 65 | 4.2 |
| 313 | 4 | 100 | 5.5 | 95 | 4.5 |
| 314 | 4 | 100 | 5.5 | 100 | 4.9 |
| 315 | 4 | 100 | 5.6 | 100 | 5.6 |
| 316 | 4 | 98 | 5.4 | 30 | <4.0 |
| 317 | 4 | 98 | 5.1 | 65 | 4.3 |
| 318 | 4 | 100 | 5.1 | 100 | 4.5 |
| 319 | 4 | 100 | 5.5 | 40 | <4.0 |
| 320 | 4 | 94 | 5.2 | 0 | — |
| 321 | 4 | 96 | 4.6 | 30 | <4.0 |
| 322 | 5 | 100 | 6.3 | 100 | 5.9 |
| 323 | 4 | 100 | 6.0 | 100 | 5.1 |
| 324 | 4 | 90 | 4.5 | 0 | — |
| 325 | 3.5 | 11 | — | 0 | — |
| 326 | 4 | 100 | 6.3 | 100 | 4.8 |
| 327 | 4 | 83 | 4.4 | 0 | <3.5 |
| 328 | 4 | 13 | 3.7 | 0 | — |
| 329 | 3.5 | −4 | — | 0 | — |
| 330 | 4 | 100 | 5.7 | 90 | 4.5 |
| 331 | 4 | 38 | 3.8 | 0 | — |
| 332 | 4 | 12 | 3.5 | 0 | — |
| 333 | 4 | 96 | 5.1 | 15 | <3.5 |

Footnotes
[1]The rate of application is expressed as the negative log of the molar concentration of the test compound in the diet.
[2]Percent growth inhibition is derived from the total weight on the insects (IW) at each rate of application in the test relative to the total weight of insects in an untreated control,
% Gr. Inh. = [IW (control) − IW (test) / IW (control)] × 100
[3]A minus % growth inhibition indicates that the insects weighed more at the termination in the test than those in the untreated control.
[4]$pI_{50}$ is the negative log of the concentration of the test chemical that provides 50% growth inhibition in the test insects.
[5]Percent mortality is derived from the number of dead insects (TD) relative to the total number of insects (TI) used in the test,
% Mortality = $\frac{TD}{TI}$ × 100
[6]$pLC_{50}$ is the negative log of the concentration of the test chemical that provides 50% mortality of the test insects.
[a]Average of 3 tests.
[b]Average of 2 tests.

TABLE 4

Insecticidal Activity When Applied as Foliar Sprays

| Cmpd No. | Rate of Application (ppm) | Percent Control[1] | | |
|---|---|---|---|---|
| | | TBW[2] | CL[3] | BAW[4] |
| 2 | 100 | 10 | 79 | 0 |
| 7 | 100 | 15 | 100 | 60 |
| 13 | 100 | 5 | 100 | 0 |
| 15 | 100 | 20 | 100 | 35 |
| 16 | 100 | 15 | 37 | 5 |
| 17 | 100 | 6 | 96* | 39 |
| 20 | 100 | 0 | 60 | 0 |
| 21 | 100 | 0 | 95 | 25 |
| 22 | 100 | 20 | 97* | 53 |
| 23 | 100 | 0 | 97* | 0 |
| 24 | 100 | 80 | 100 | 55 |
| 27 | 100 | 45 | 100 | 65 |
| 28 | 100 | 95* | 100* | 90* |
| 29 | 100 | 100* | 97* | 100* |
| 31 | 100 | 95 | 21 | 81 |
| 32 | 100 | 97* | 100* | 85* |

TABLE 4-continued

Insecticidal Activity When Applied as Foliar Sprays

| Cmpd No. | Rate of Application (ppm) | Percent Control[1] TBW[2] | CL[3] | BAW[4] |
|---|---|---|---|---|
| 33 | 100 | 21 | 60 | 15 |
| 34 | 100 | 35 | 100 | 63 |
| 36 | 100 | 33 | 100 | 75 |
| 38 | 100 | 11 | 5 | 0 |
| 39 | 100 | 100 | 100 | 42 |
| 40 | 100 | 5 | 25 | 5 |
| 41 | 100 | 5 | — | 0 |
| 42 | 100 | 95* | 100* | 93* |
| 43 | 100 | 92* | 100* | 95* |
| 44 | 100 | 20 | 100 | 45 |
| 45 | 100 | 90 | 85 | 95 |
| 46 | 100 | 73* | 100* | 95* |
| 47 | 100 | 97* | 87* | 97* |
| 48 | 100 | 100* | 65* | 95* |
| 51 | 100 | 0 | 15 | 0 |
| 52 | 100 | 11 | 100 | 60 |
| 53 | 100 | 28 | — | 5 |
| 54 | 100 | 65 | 0 | 63 |
| 55 | 100 | 25 | 100 | 5 |
| 57 | 100 | 100 | 90 | 100 |
| 58 | 100 | 95 | 10 | 90 |
| 59 | 100 | 0 | 0 | 10 |
| 60 | 100 | 95 | 35 | 100 |
| 64 | 100 | 11 | 25 | 0 |
| 67 | 100 | 100 | 90 | 95 |
| 68 | 100 | 15 | 0 | 0 |
| 69 | 100 | 12 | 67 | 10 |
| 78 | 100 | 100 | 100 | 65 |
| 79 | 100 | 100 | 100 | 100 |
| 80 | 100 | 100 | 100 | 100 |
| 85 | 100 | 85 | 80 | 78 |
| 88 | 100 | 72* | 90* | 35 |
| 89 | 100 | 95 | 95 | 85 |
| 90 | 100 | 85 | 100 | 80 |
| 94 | 100 | 90 | 95 | — |
| 104 | 100 | 95* | 90* | 98* |
| 110 | 100 | 0 | 20 | 0 |
| 112 | 100 | 98* | 100* | 100* |
| 113 | 100 | 100 | 80 | 35 |
| 114 | 100 | 80 | 95 | 25 |
| 115 | 100 | 100 | 100 | 100 |
| 117 | 100 | 95 | 100 | 45 |
| 120 | 100 | 49* | 90* | 90* |
| 121 | 100 | 100 | 11 | 100 |
| 122 | 100 | 100 | 80 | 100 |
| 123 | 100 | 100* | 100* | 100* |
| 124 | 100 | 100 | 60 | 100 |
| 128 | 100 | 11 | — | — |
| 129 | 100 | 58 | — | — |
| 130 | 100 | 100 | 85 | 100 |
| 132 | 100 | 100 | 50 | 16 |
| 137 | 100 | 56 | 90 | 63 |
| 138 | 100 | 74 | 100 | 0 |
| 139 | 100 | 100 | 100 | 100 |
| 140 | 100 | 65 | 100 | 53 |
| 141 | 100 | 100 | 58 | 90 |
| 142 | 100 | 100 | 95 | 65 |
| 145 | 100 | 100 | 90 | 100* |
| 150 | 100 | 100 | 100 | 74 |
| 151 | 100 | 100 | 90 | 95 |
| 153 | 100 | 30 | — | — |
| 158 | 100 | 65 | 95 | 95 |
| 159 | 100 | 95 | 84 | 100 |
| 160 | 100 | 5 | — | — |
| 163 | 100 | 20 | 31* | 30 |
| 173 | 100 | 80 | 95 | 95 |
| 175 | 100 | 98* | 100* | 100* |
| 176 | 100 | 93* | 100* | 95 |
| 177 | 100 | 100 | 100 | 100 |
| 184 | 100 | 40 | — | — |
| 192 | 100 | 100* | 100 | 100* |
| 193 | 100 | 95 | 100 | 100 |
| 194 | 100 | 100 | 95 | 95 |
| 195 | 100 | 95 | 95 | 95 |
| 197 | 100 | 95 | 100 | 100 |
| 202 | 100 | 95 | 95 | 95 |
| 204 | 100 | 89 | 70 | 30 |
| 209 | 100 | 100 | 100 | 100 |
| 214 | 100 | 95 | 100 | 100 |
| 215 | 100 | 100 | 100 | 100 |
| 231 | 100 | 45 | 40 | 10 |
| 259 | 100 | 40 | 100 | 10 |
| 260 | 100 | 100 | 100 | 100 |
| 276 | 100 | 100 | 100 | 85 |
| 281 | 100 | 95 | 90 | 95 |
| 283 | 1100 | 100 | 100 | 100 |
| 284 | 100 | 100* | 100* | 100* |
| 288 | 100 | 100 | 100 | 90 |
| 294 | 100 | 61 | 95 | 45 |
| 295 | 100 | 100 | 85* | 100* |
| 296 | 100 | 95 | 90 | 80 |
| 297 | 100 | 100 | 100 | 100 |
| 298 | 100 | 100 | 95* | 100 |
| 299 | 100 | 100 | 95 | 75 |
| 300 | 100 | 85 | 100 | 65 |
| 303 | 100 | 100 | 100 | 100 |
| 310 | 100 | 95 | 60 | 15 |
| 315 | 100 | 100 | 100 | 100 |
| 322 | 100 | 100* | 100* | 100* |

[1]Percent control is derived from the total number of dead insects (TD) plus the total number of moribund insects (TM) as compared to the total number of insects (TI) in the test:

$$\% \text{ Control} = \frac{TD + TM}{TI} \times 100$$

[2]TBW is tobacco budworm (*Heliothis virescens* [Fabricius])
[3]CL is cabbage looper (*Trichoplusia ni* [Hubner].
[4]BAW is beet armyworm (*Spodoptera exigua* [Hubner].
*indicates an average of more than one test.

We claim:

1. A compound of the formula:

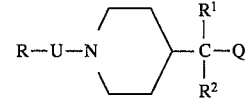

in which

U is selected from —$(CH_2)_n$— and ethylidene;

Q is selected from hydrogen, hydroxy, sulfhydryl, and fluorine;

R is

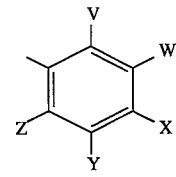

in which

V is selected from hydrogen, halogen, alkyl, haloalkyl, alkoxy, alkylthio, alkylsulfinyl, alkylsilyloxy, dialkylamino, cyano, nitro, hydroxy, and phenyl;

W is selected from hydrogen, halogen, alkyl, haloalkyl, alkoxy, nitro, amino, phenoxy, and phenylalkoxy;

X is selected from hydrogen, hydroxy, halogen, alkyl, alkoxyalkyl, alkoxy, cycloalkylalkoxy, haloalkoxy, alkenyloxy, haloalkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkoxycarbonylamino, alkylcarbonyl, alkoxycarbonyl, alkylaminocarbonyl, aminocarbonyloxy, phenyl, phenylalkoxy, phenoxy, and phenoxyalkyl;

Y and Z are independently selected from hydrogen and alkoxy;

$R^1$ and $R^2$ are independently selected from phenyl substituted with haloalkyl, haloalkoxy, alkoxyalkyl, dialkylaminosulfonyl, hydroxyalkylaminocarbonyl, alkylsulfonyloxy, and haloalkylsulfonyloxy, with the proviso that haloalkyl is not trifluoromethyl; and n is 1, 2, or 3;

with the proviso that each aliphatic moiety contains not more than 6 carbon atoms, halogen means chlorine or fluorine, phenyl, or cycloallkyl moiety is optionally substituted with one or more halogen or alkyl or alkoxy of 1 to 3 carbon atoms, and each alkyl substituent on an amino nitrogen contains 1 to 3 carbon atoms;

and the corresponding N-oxides and agriculturally acceptable salts.

2. A compound of claim 1 in which

U is —$(CH_2)_n$—;

Q is selected from hydrogen and hydroxy;

V is selected from hydrogen and halogen;

Y and Z are each hydrogen;

W is selected from hydrogen, halogen, and alkoxy; and

X is selected from hydrogen, hydroxy, halogen, alkyl, haloalkyl, alkenyl, alkynyl, alkoxy, cycloalkylalkoxy, alkenyloxy, alkynyloxy, haloalkoxy, alkylthio, haloalkylthio, monoalkylamino, dialkylamino, alkoxyalkyl, alkoxyalkoxy, alkylcarbonyl, alkoxycarbonyl, alkylaminocarbonyl, alkylcarbonylamino, aminocarbonyloxy, alkoxycarbonylamino, cyano, phenyl, phenoxy, phenoxyalkoxy, and optionally substituted phenylalkoxy;

$R^1$ and $R^2$ are independently selected from phenyl substituted with haloalkyl and haloalkoxy with the proviso that it is not $CF_3$, each in the 4-position; and n is 1;

with the proviso that each aliphatic moiety contains 1 to 4 carbon atoms; each cycloalkyl moiety contains 3 to 6 carbon atoms; halogen means chlorine or fluorine, each alkyl or alkoxy substituent on nitrogen contains 1 or 2 carbon atoms, and each phenyl or cycloalkyl moiety is optionally substituted with one or more halogen or alkyl or alkoxy of 1 to 3 carbon atoms;

and the corresponding N-oxides and agriculturally acceptable salts.

3. A compound of claim 2 in which

Q is hydroxy;

V is selected from hydrogen, fluorine, and methoxy;

W is selected from hydrogen, fluorine, methyl, methoxy and ethoxy; and

X is selected from hydrogen, halogen, methyl, methoxy, ethoxy, n-propoxy, i-propoxy, n-butoxy, 1-methylpropoxy, 2-methylpropoxy, cyclopropylmethoxy, 2-chloro-2-propenoxy, 3-chloro-2-propenoxy, 2-methyl-2-propenoxy, 3-methyl-2-butenoxy, 1-methylcyclopropylmethoxy, 2-methylcyclopropylmethoxy, cyclobutylmethoxy, cyclohexoxy, perfluoroethoxy, allyloxy, propargyloxy, 2-butynoxy, difluoromethoxy, perfluoroethylthio, cyanomethoxy, (methyl)cyanomethoxy, 2-methoxyethoxymethoxy, cyano, phenyl, phenoxy, 2-fluorophenoxy, 4-fluorophenoxy, phenylmethoxy, ethylcarbonyl, ethoxymethyl, methoxycarbonyl, ethoxycarbonyl, i-propoxycarbonyl, methoxymethoxycarbonyl, methylcarbonylmethoxy, dimethylamino, methylcarbonylamino, ethylcarbonylamino, methoxycarbonylamino, ethoxycarbonylamino, i-propoxycarbonylamino, butoxycarbonylamino, (N-methyl)methoxycarbonylamino, 2,2,2-trifluoroethoxycarbonylamino, (N-propyl)methoxycarbonylamino, cyclopentoxycarbonylamino, phenoxycarbonylamino, dimethylaminocarbonyloxy, methylaminocarbonyloxy, ethylaminocarbonyloxy, and ethoxysulfonyl.

4. A compound of claim 3 in which W is selected from hydrogen, fluorine, and methoxy.

5. A compound of claim 4 in which W is hydrogen and $R^1$ and $R^2$ are each p-trifluoromethoxyphenyl.

6. The compound of claim 5 in which V is methoxy and X is n-propoxy.

7. A compound of claim 5 in which V is hydrogen, and X is ethoxy, 2-chloroethoxy, n-propoxy, cyclopropylmethoxy, ethoxycarbonyl, i-propoxycarbonyl, methylaminocarbonyloxy, methoxycarbonylamino, or i-propoxycarbonylamino.

8. The compound of claim 7 that is N-(4-ethoxyphenylmethyl)-4-[bis(4-trifluoromethoxyphenyl)hydroxymethyl]piperidine.

9. The compound of claim 7 that is N-(4-n-propoxyphenylmethyl)-4-[bis(4-trifluoromethoxyphenyl)hydroxymethyl]piperidine.

10. The compound of claim 7 that is N-(4-ethoxycarbonylphenylmethyl)-4-[bis(4-trifluoromethoxyphenyl)hydroxymethyl]piperidine.

11. The compound of claim 7 that is N-(4-cyclopropylmethoxyphenylmethyl)-4-[bis(4-trifluoromethoxyphenyl)hydroxymethyl]piperidine.

12. The compound of claim 7 that is N-(4-n-propoxyphenylmethyl)-4-[bis(4-trifluoromethoxyphenyl)hydroxymethyl]piperidine N-oxide.

13. The compound of claim 7 that is N-(4-cyclopropylmethoxyphenylmethyl)-4-[bis(4-trifluoromethoxyphenyl)hydroxymethyl]piperidine N-oxide.

14. The compound of claim 7 that is N-(4-i-propoxyphenylmethyl)-4-[bis(4-trifluoromethoxyphenyl)hydroxymethyl]piperidine.

15. The compound of claim 7 that is N-[4-(2-chloroethoxy)phenylmethyl]-4-[bis(4-trifluoromethoxyphenyl)hydroxymethyl]piperidine.

16. The compound of claim 7 that is N-(4-i-propoxycarbonylphenylmethyl)-4-[bis(4-trifluoromethoxyphenyl)hydroxymethyl]piperidine.

17. The compound of claim 7 that is N-(4-methylaminocarbonyloxyphenylmethyl)-4-[bis(4-trifluoromethoxyphenyl)hydroxymethyl]piperidine.

18. The compound of claim 7 that is N-(4-methoxycarbonylaminophenylmethyl)-4-[bis(4-trifluoromethoxyphenyl)hydroxymethyl]piperidine.

19. The compound of claim 7 that is N-(4-i-propoxycarbonylaminophenylmethyl)-4-[bis(4-trifluoromethoxyphenyl)hydroxymethyl]piperidine.

20. The compound of claim 7 that is N-(4-methoxycarbonylaminophenylmethyl)-4-[bis(4-trifluoromethoxyphenyl)hydroxymethyl]piperidine N-oxide.

21. A composition containing an insecticidally effective amount of a compound of claim 1 in admixture with a least one agriculturally acceptable extender or adjuvant.

22. A method of controlling insects which comprises applying to the locus where control is desired an insecticidally effective amount of a compound of the formula:

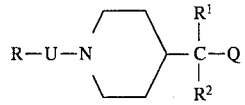

in which

U is selected from —(CH$_2$)$_n$— and ethylidene;

Q is selected from hydrogen, hydroxy, sulfhydryl, and fluorine;

R is

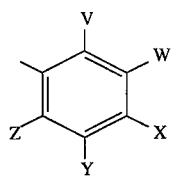

in which

V is selected from hydrogen, halogen, alkyl, haloalkyl, alkoxy, alkylthio, alkylsulfinyl, alkylsilyloxy, dialkylamino, cyano, nitro, hydroxy, and phenyl;

W is selected from hydrogen, halogen, alkyl, haloalkyl, alkoxy, nitro, amino, phenoxy, and phenylalkoxy;

X is selected from hydrogen, hydroxy, halogen, alkyl, alkoxyalkyl, alkoxy, cycloalkylalkoxy, haloalkoxy, alkenyloxy, haloalkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkoxycarbonylamino, alkylcarbonyl, alkoxycarbonyl, alkylaminocarbonyl, aminocarbonyloxy, phenyl, phenylalkoxy, phenoxy, and phenoxyalkyl;

Y and Z are independently selected from hydrogen and alkoxy;

R$^1$ and R$^2$ are independently selected from phenyl substituted with halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and n is 1, 2, or 3;

with the proviso that each aliphatic moiety contains not more than 6 carbon atoms, halogen means chlorine or fluorine, each phenyl or cycloalkyl moiety is optionally substituted with one or more halogen or alkyl or alkoxy of 1 to 3 carbon atoms, and each alkyl substituent on an amino nitrogen contains 1 to 3 carbon atoms;

and the corresponding N-oxides and agriculturally acceptable salts.

23. A method of claim 22 in which U is —(CH$_2$)$_n$—; Q is selected from hydrogen and hydroxy; V is selected from hydrogen and halogen; Y and Z are each hydrogen; W is selected from hydrogen, halogen, and alkoxy;

X is selected from hydrogen, hydroxy, halogen, alkyl, haloalkyl, alkenyl, alkynyl, alkoxy, cycloalkylalkoxy, alkenyloxy, alkynyloxy, haloalkoxy, alkylthio, haloalkylthio, monoalkylamino, dialkylamino, alkoxyalkyl, alkoxyalkoxy, alkylcarbonyl, alkoxycarbonyl, alkylaminocarbonyl, alkylcarbonylamino, aminocarbonyloxy, alkoxycarbonylamino, cyano, phenyl, phenoxy, phenoxyalkyl, and optionally substituted phenylalkoxy, and a five-membered heterocycle;

R$^1$ and R$^2$ are independently selected from phenyl substituted with halogen, haloalkyl, or haloalkoxy; and n is 1 with the proviso that one of R$^1$ and R$^2$ is phenyl substituted in the para position, each aliphatic moiety contains 1 to 4 carbon atoms, each cycloalkyl moiety contains 3 or 4 carbon atoms; halogen means chlorine or fluorine, each alkyl or alkoxy substituent on nitrogen contains 1 or 2 carbon atoms, each heterocycle contains from 1 to 4 nitrogen atoms, or 1 or 2 oxygen atoms, or 1 or 2 nitrogen atoms and an oxygen atom, and each phenyl, heterocycle, or cycloalkyl moiety is optionally substituted with one or more halogen or alkyl or alkoxy of 1 to 3 carbon atoms;

and the corresponding N-oxides and agriculturally acceptable salts.

24. A method of claim 23 in which Q is hydroxy: V is selected from hydrogen, fluorine, and methoxy; W is selected from hydrogen, fluorine, methyl, methoxy and ethoxy;

X is selected from hydrogen, halogen, methyl, methoxy, ethoxy, n-propoxy, i-propoxy, n-butoxy, 1-methylpropoxy, 2-methylpropoxy, cyclopropylmethoxy, 2-chloro-2-propenoxy, 3-chloro-2-propenoxy, 2-methyl-2-propenoxy, 3-methyl-2-butenoxy, 1-methylcyclopropylmethoxy, 2-methylcyclopropylmethoxy, cyclobutylmethoxy, cyclohexoxy, perfluoroethoxy, allyloxy, propargyloxy, 2-butynoxy, difluoromethoxy, perfluoroethylthio, cyanomethoxy, (methyl)cyanomethoxy, 2-methoxyethoxymethoxy, cyano, phenyl, phenoxy, 2-fluorophenoxy, 4-fluorophenoxy, phenylmethoxy, ethylcarbonyl, ethoxymethyl, methoxycarbonyl, ethoxycarbonyl, i-propoxycarbonyl, methoxymethoxycarbonyl, methylcarbonylmethoxy, dimethylamino, methylcarbonylamino, ethylcarbonylamino, methoxycarbonylamino, ethoxycarbonylamino, i-propoxycarbonylamino, butoxycarbonylamino, (N-methyl)methoxycarbonylamino, 2,2,2-trifluoroethoxycarbonylamino, (N-propyl)methoxycarbonylamino, cyclopentoxycarbonylamino, phenoxycarbonylamino, dimethylaminocarbonyloxy, methylaminocarbonyloxy, ethylaminocarbonyloxy, ethoxysulfonyl; and R$^1$ and R$^2$ are independently selected from p-trifluoromethoxyphenyl and p-trifluoromethylphenyl.

25. A method of claim 24 in which W is selected from hydrogen, fluorine, and methoxy.

26. A method of claim 25 in which W is hydrogen and R$^1$ and R$^2$ are each p-trifluoromethylphenyl.

27. A method of claim 26 in which V is hydrogen and X is ethoxy, 2-chloroethoxy, n-propoxy, cyclopropylmethoxy, ethoxycarbonyl, i-propoxycarbonyl, methylaminocarbonyloxy, methoxycarbonylamino, or i-propoxycarbonylamino.

28. A method of claim 27 in which the compound is N-(4-n-propoxyphenylmethyl)-4-[bis(4-trifluoromethylphenyl)hydroxymethyl]piperidine.

29. A method of claim 27 in which the compound is N-(4-n-propoxyphenylmethyl)-4-[bis(4-trifluoromethylphenl)hydroxymethyl]piperidine N-oxide.

30. A method of claim 27 in which the compound is N-(4-cyclopropylmethoxyphenylmethyl)-4-[bis(4-trifluoromethylphenyl)hydroxymethyl]piperidine N-oxide.

31. A method of claim 27 in which the compound is N-(4-methoxycarbonylaminophenylmethyl)-4-[bis(4-trifluoromethylphenyl)hydroxymethyl]piperidine N-oxide.

* * * * *